(12) United States Patent
Sullivan et al.

(10) Patent No.: US 10,603,480 B2
(45) Date of Patent: Mar. 31, 2020

(54) METHOD AND DEVICE FOR INSERTION OF TUBING INTO IRRIGATION AND INFUSION FLUID PUMPS

(71) Applicant: STELLARTECH RESEARCH CORPORATION, Milpitas, CA (US)

(72) Inventors: Sean Y. Sullivan, Santa Clara, CA (US); Patrick K. Howe, Hollister, CA (US); Stanley Levy, Saratoga, CA (US)

(73) Assignee: STELLARTECH RESEARCH CORPORATION, Milpitas, CA (US)

( * ) Notice: Subject to any disclaimer, the term of this patent is extended or adjusted under 35 U.S.C. 154(b) by 626 days.

(21) Appl. No.: 14/693,831

(22) Filed: Apr. 22, 2015

(65) Prior Publication Data

US 2015/0224254 A1    Aug. 13, 2015

Related U.S. Application Data

(63) Continuation-in-part of application No. 14/280,643, filed on May 18, 2014, now abandoned, which is a
(Continued)

(51) Int. Cl.
*F04B 43/12*    (2006.01)
*A61M 39/12*   (2006.01)
(Continued)

(52) U.S. Cl.
CPC .......... *A61M 39/12* (2013.01); *A61M 3/0254* (2013.01); *A61M 5/1418* (2013.01); *A61M 5/14228* (2013.01); *A61M 5/16831* (2013.01); *A61M 39/28* (2013.01); *F04B 43/12*
(2013.01); *A61M 3/022* (2014.02); *A61M 3/0216* (2014.02); *A61M 2205/14* (2013.01);
(Continued)

(58) Field of Classification Search
CPC ................ F04B 43/0072; F04B 423/12; F04B 43/1238; F04B 43/1253
See application file for complete search history.

(56) References Cited

U.S. PATENT DOCUMENTS 3,963,023 A * 6/1976 Hankinson .......... F04B 43/1253
                                                       417/477.11
4,382,753 A      5/1983 Archibald
(Continued)

FOREIGN PATENT DOCUMENTS

JP    WO 2014077308 A1 *  5/2014  .............. F04B 43/08

*Primary Examiner* — Patrick Hamo
(74) *Attorney, Agent, or Firm* — Bowen Liu; David Lewis

(57) ABSTRACT

In one embodiment, a door is used to provide uniform pressure to insert tubing into slots of a pump having walls that are narrower than the outer diameter of the tubing. In another embodiment, connectors are attached to receptacles on the pump, where the connectors insert and/or hold the tubing in slots of the pump. The connectors push the tubing into the slots while closing thereby covering the slots, which helps assure that the tubing is properly inserted into the slots. Optionally, the tubing may be partially affixed to the connectors so that detaching the connectors from the pump receptacles may remove the tubing from the slots. In one embodiment, as long as the connectors are connected to the pump receptacles properly, the tubing is properly inserted and/or retained in the slots.

25 Claims, 45 Drawing Sheets

Related U.S. Application Data continuation of application No. 13/359,455, filed on Jan. 26, 2012, now abandoned.

(60) Provisional application No. 61/436,589, filed on Jan. 26, 2011.

(51) Int. Cl.

| | | |
|---|---|---|
| *A61M 3/02* | (2006.01) | |
| *A61M 5/142* | (2006.01) | |
| *A61M 5/14* | (2006.01) | |
| *A61M 5/168* | (2006.01) | |
| *A61M 39/28* | (2006.01) | |

(52) U.S. Cl.
CPC ............ *A61M 2205/3331* (2013.01); *A61M 2205/3379* (2013.01); *A61M 2207/00* (2013.01); *Y10T 29/49826* (2015.01)

(56) References Cited

U.S. PATENT DOCUMENTS

| | | | | |
|---|---|---|---|---|
| 6,059,544 | A * | 5/2000 | Jung | A61M 1/0058 |
| | | | | 417/477.2 |
| 7,273,359 | B2 * | 9/2007 | Blight | A61M 3/0258 |
| | | | | 417/44.2 |
| 7,727,176 | B2 * | 6/2010 | Tonelli | A61M 1/16 |
| | | | | 137/861 |
| 7,798,996 | B1 * | 9/2010 | Haddad | A61M 5/16831 |
| | | | | 417/477.2 |
| 7,934,912 | B2 * | 5/2011 | Voltenburg, Jr. | ........................... |
| | | | | A61M 5/14232 |
| | | | | 417/477.11 |
| 8,029,253 | B2 | 10/2011 | Rotem et al. | |
| 8,308,457 | B2 * | 11/2012 | Rotem | A61M 5/14228 |
| | | | | 417/479 |
| 8,353,683 | B2 * | 1/2013 | Miyazaki | F04B 19/006 |
| | | | | 417/360 |
| 8,459,968 | B2 | 6/2013 | Juretich et al. | |
| 8,784,359 | B2 * | 7/2014 | Plahey | A61M 1/28 |
| | | | | 417/395 |
| 9,388,803 | B2 * | 7/2016 | Schaefer | F04B 43/08 |
| 9,468,716 | B2 * | 10/2016 | Hariharesan | A61M 5/14232 |
| 2007/0269324 | A1 * | 11/2007 | Goldor | A61M 5/14228 |
| | | | | 417/474 |
| 2009/0087326 | A1 | 4/2009 | Voltenburg, Jr. et al. | |
| 2009/0087327 | A1 | 4/2009 | Voltenburg, Jr. et al. | |
| 2011/0300010 | A1 * | 12/2011 | Jarnagin | A61B 17/3207 |
| | | | | 417/477.2 |
| 2011/0313358 | A1 * | 12/2011 | Hariharesan | A61M 5/14228 |
| | | | | 604/151 |
| 2012/0082576 | A1 * | 4/2012 | Beck | F04B 43/0081 |
| | | | | 417/474 |
| 2015/0204321 | A1 * | 7/2015 | Schnekenburger | ........................... |
| | | | | F04B 43/1276 |
| | | | | 417/477.2 |
| 2015/0285404 | A1 * | 10/2015 | Koyama | F04B 43/12 |
| | | | | 248/74.2 |

* cited by examiner

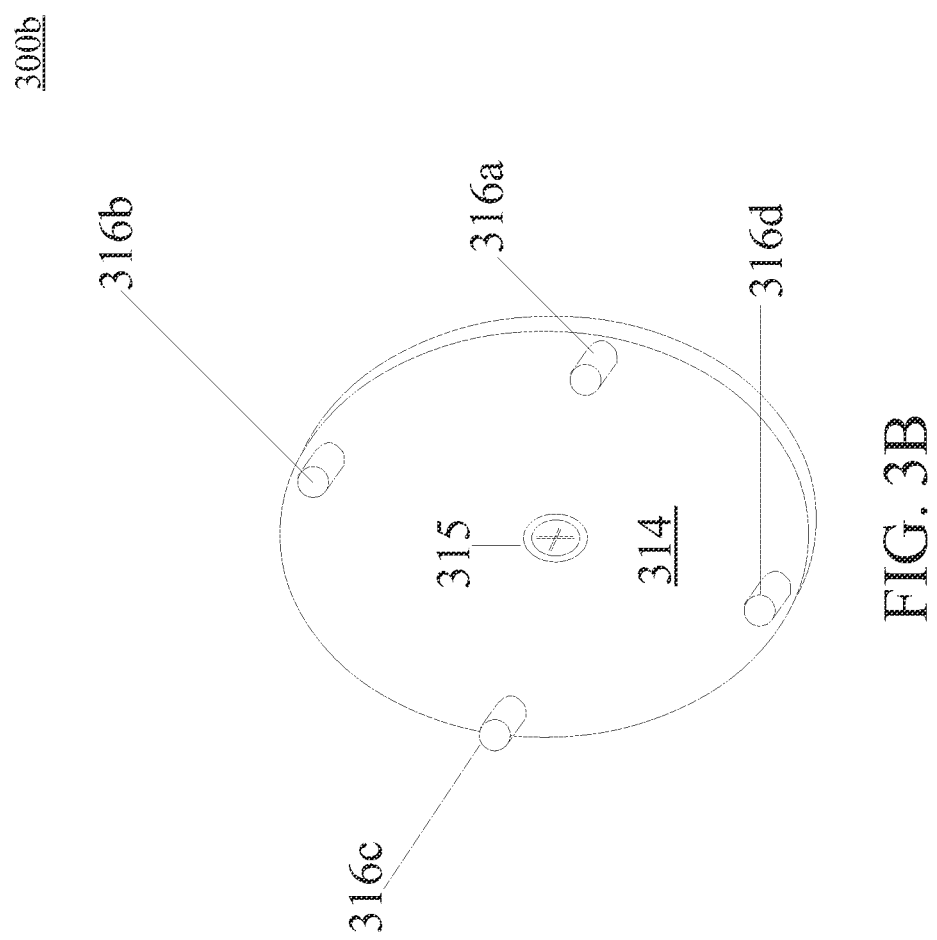

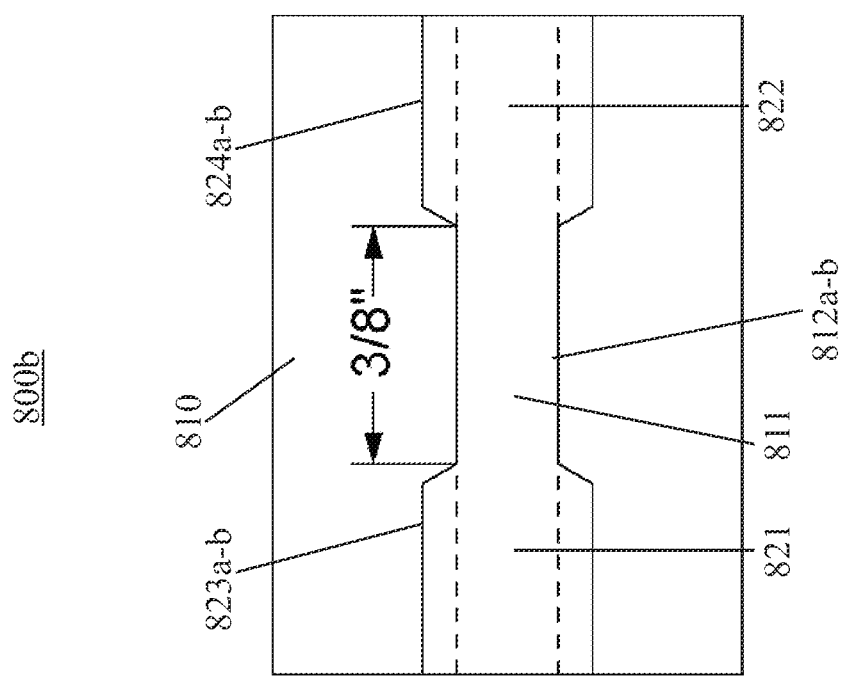

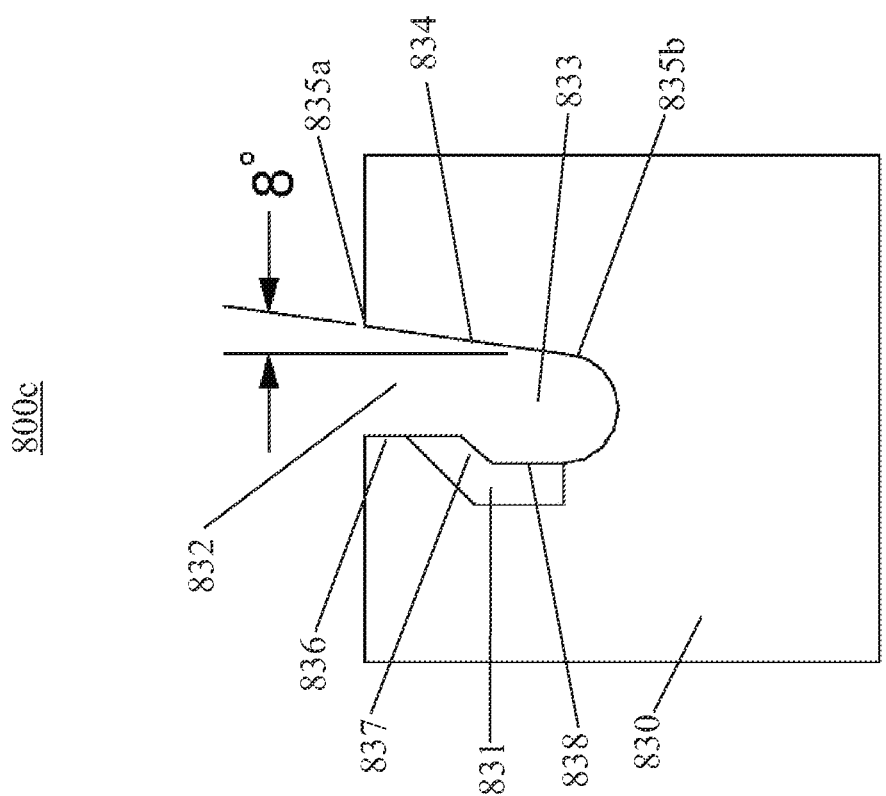

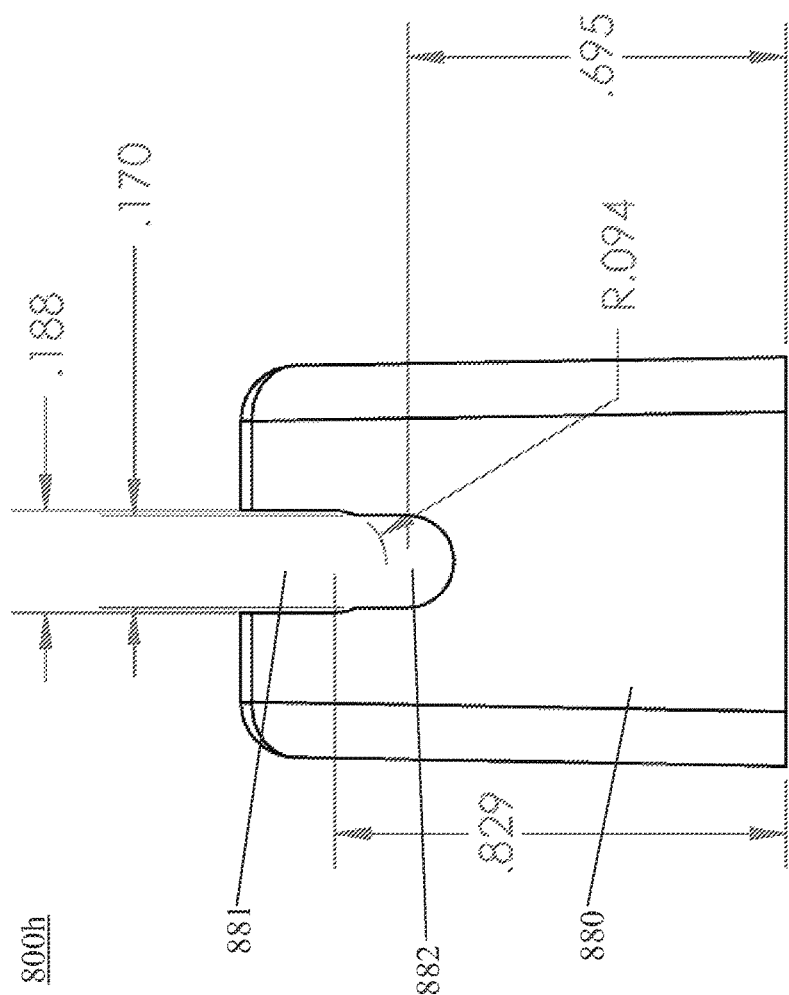

METHOD AND DEVICE FOR INSERTION OF TUBING INTO IRRIGATION AND INFUSION FLUID PUMPS

CROSS-REFERENCE TO RELATED APPLICATIONS

This application is a continuation-in-part of U.S. patent application Ser. No. 14/280,643, entitled "Method and Device for Insertion of Tubing into irrigation and Infusion Fluid Pumps," filed May 18, 2014, by Sean Y. Sullivan et al., which in turn is a continuation of U.S. patent application Ser. No. 13/359,455, entitled "Method and Device for insertion of Tubing into Irrigation and Infusion Fluid Pumps," filed Jan. 26, 2012, by Sean Y. Sullivan et al., which in turn claims priority to U.S. Provisional Patent Application Ser. No. 61/436,589, filed Jan. 26, 2011, by Sean Y. Sullivan et al. All of the above Applications are incorporated herein by reference.

FIELD

This specification generally relates to delivering fluids to patients.

BACKGROUND

The subject matter discussed in the background section should not be assumed to be prior art merely as a result of its mention in the background section. Similarly, a problem and the understanding of the causes of a problem mentioned in the background section or associated with the subject matter of the background section should not be assumed to have been previously recognized in the prior art. The subject matter in the background section may merely represent different approaches, which in and of themselves may also be inventions.

Medical diagnostic and therapeutic procedures often involve delivering fluids to patients. For example, procedures affecting subcutaneous or internal tissues often utilize catheters to access these tissues. There are many other medical procedures involving delivery of fluids to patients including delivery of medications, nutrients, anesthetic agents, and diagnostic agents. Examples of procedures utilizing catheters include delivery of medicines to tissue sites, measurement of tissue electrical and mechanical properties, imaging of tissues, and ablation of tissues. These procedures may use catheters which require the delivery of fluids to these tissues or the circulation of fluids within the catheter.

BRIEF DESCRIPTION OF THE FIGURES

In the following drawings like reference numbers are used to refer to like elements. Although the following figures depict various examples of the invention, the invention is not limited to the examples depicted in the figures.

FIG. 3B shows another view of an example of rotor assembly that may be used in the pump system of FIG. 3A;

FIG. 8B shows a view of an embodiment of the sensor and sensor slot of FIG. 8A;

FIG. 8C shows a cross sectional side view of another embodiment of a sensor having a sensor slot;

FIG. 8H shows a side view of another embodiment of a pressure sensor with a sensor slot;

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification.

Some embodiments may only partially address some deficiencies or just one deficiency that may be discussed in the specification, and some embodiments may not address any of these deficiencies.

In general, at the beginning of the discussion of each of FIGS. 1-9B is a brief description of each element, which may have no more than the name of each of the elements in the one of FIGS. 1-9B that is being discussed. After the brief description of each element, each element is further discussed in numerical order. In general, each of FIGS. 1-9B is discussed in numerical order and the elements within FIGS. 1-9B are also usually discussed in numerical order to facilitate easily locating the discussion of a particular element. Nonetheless, there is no one location where all of the information of any element of FIGS. 1-9B is necessarily located. Unique information about any particular element or any other aspect of any of FIGS. 1-9B may be found in, or implied by, any part of the specification.

In various places in discussing the drawings a range of letters, such as a-n are used to refer to individual elements of various series of elements that are the same. In each of these series, the ending letters are integer variables that can be any number. Unless indicated otherwise, the number of elements in each of these series is unrelated to the number of elements in others of these series. Specifically, even though one letter (e.g. "c") comes earlier in the alphabet than another letter (e.g., "n"), the order of these letters in the alphabet does not mean that the earlier letter represents a smaller number. The value of the earlier letter is unrelated to the later letter, and may represent a value that is greater the same or less than the later letter.

Figure 1:
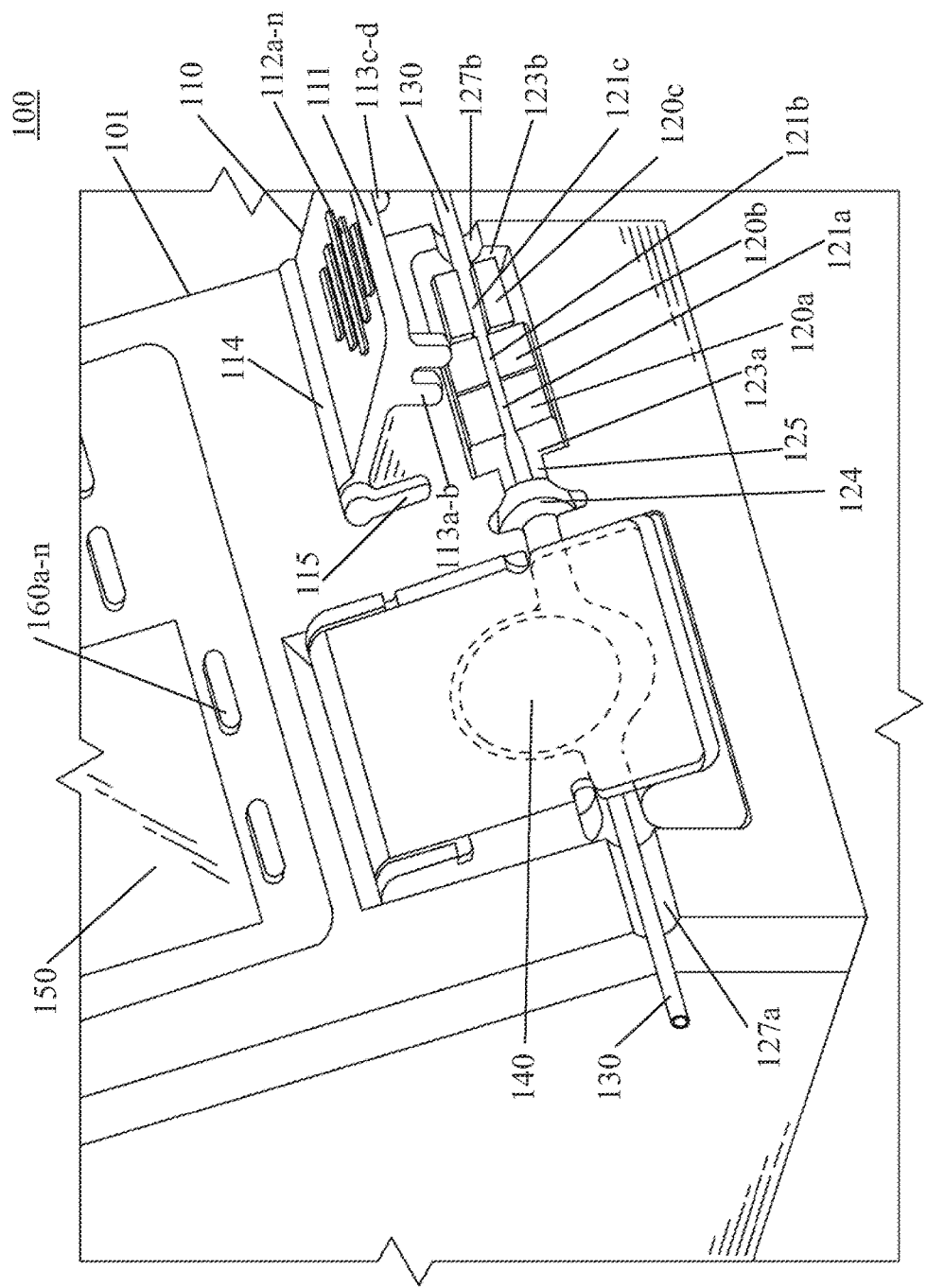
FIG. 1 shows an embodiment of a device for inserting tubing into irrigation pumps and infusion fluid pumps.

FIG. 1 shows an embodiment of a device 100 for inserting tubing into irrigation pumps and infusion fluid pumps. FIG. 1 may include a pump 101, a door 110, a flat portion 111, bumps 112a-n, guiding stubs 113a-d, a hinge 114, an optional lock 115, sensors 120a-c, sensor slots 121a-c, openings 123a and 123b, bearing 124, opening 125, guiding concaves 127a and 127b, tubing 130, a pump mechanism 140, an output system 150, and buttons 160a-n. In other embodiments, FIG. 1 may not have all of the elements or features listed and/or may have other elements or features instead of or in addition to those listed.

Pump 101 is a pump for delivering fluid to catheters or tubing for irrigation or infusion purposes. For example, pump 101 may be used to deliver fluid to ablation catheters (during ablation the fluid provides cooling of the catheter tip or adjacent tissues). In one embodiment, fluid may be circulated in a loop enclosed within the catheter, often referred to as closed loop cooling. In other embodiments, fluid may be delivered, for example into heart's chambers, often referred to as open irrigation where the fluid is mixed with blood. In at least one embodiment, pump 101 includes a pump mechanism that is required to deliver fluid (e.g., sterile saline) in a controlled and safe manner. Optionally, the fluid (e.g., sterile saline) is supplied from bags connected to tubing that is inserted into the pump mechanism.

In at least one embodiment, pump 101 is a peristaltic pump, and/or uses a pumping method that is peristaltic style, which moves the fluid by successive compression and relaxation of the tubing or by moving compressing a location and moving the region that is compressed in the direction in which it is desired to pump the fluid, causing the fluid to be pushed through the tubing into the catheter. In at least one embodiment, pump 101 includes one or more sensors to detect the presence of air bubbles in the fluid, which could pose a safety risk to the patient. In another embodiment, pump 101 may include other types of sensors for detecting other fluid properties including, but not limited to, pressure, velocity, flow rate, composition, optical characteristics, and electrical characteristics.

At least one embodiment of this specification relates to devices and/or methods that improve the ease and reliability of tubing insertion into medical irrigation and infusion fluid pumps. At least one embodiment relates to the insertion of tubing into sensor slot(s) on the pumps. In at least one embodiment, a user must insert the tubing into slots in the sensors for the pump 101 to function correctly. In at least one embodiment, in order for the sensors to function properly, the tubing must fit snuggly into the sensor slots such that there is intimate contact between the walls of the sensors and the wall of the tubing. In at least one embodiment, in order to secure the tubing in the sensors, the sensors are designed with slots that are 0.030" to 0.050" smaller than the outside diameter of the tubing and may have an entrance opening that is even smaller to act as a retainer for the tubing. The use of a tight fitting the tubing, may require users to elongate the tubing prior to insertion and then to push the tubing into the sensor slots, to fully insert the tubing into the sensor slots. The process of elongating the tubing and pushing the tubing into the slot while the tubing is still elongated is subject to user technique and can often lead to partially inserted tubing and complaints by users regarding the difficulty inserting the tubing.

Door 110 is a structure that is connected to the pump 101 via a hinge for assisting tubing insertion and/or retention. In at least one embodiment, door 110 aligns with entrance openings of sensors on the pump 101, which entrance openings are intended for tubing insertion. In another embodiment, door 110 may align with a peristaltic pump mechanism on pump 101 for assisting and/or retaining tubing in the pump mechanism. In at least one embodiment, the door 110 includes structures that provide mechanical leverage for fully and uniformly inserting the tubing into the sensor slots. The mechanical leverage overcomes the resistance to the tubing sliding into the sensor slots, where the resistance is due to the tight fit of the tubing within the sensor slots. In at least one embodiment, the door 110 includes guiding stubs to engage and/or retain the tubing along the tubing's length. In at least one embodiment, the user places the tubing on the door to fit in-between the guiding stubs while the door is open. In an alternative embodiment, the user positions the tubing at the entrance openings to sensor slots of the sensors, optionally via guiding structures on either side(s) of the sensor(s) to retain the tubing in a proper position.

In at least one embodiment, the door 110 is connected via a hinge to the pump 101 and can be locked and/or retained via a clutch. In at least one embodiment, when the door 110 is fully closed, a latch retains the door in its closed position and the tubing in a fully inserted position in the sensor slots. In one embodiment, the tubing is retained by the door 110 and is removed from the sensor slots when the door 110 is opened. In an alternative embodiment when tubing is not retained by the door 110, tubing may be removed by releasing the latch and opening the door 110, and then pulling the tubing out of the sensor slots.

Flat portion 111 is a flat plate or panel of the door 110 that aligns with sensors on the pump 101. In at least one embodiment, the flat portion 111 is rectangular with one side connected to the pump 101, via a hinge and may rotate with respect to the hinge. In at least one embodiment, flat portion 111 includes one or more pairs of guiding stubs 113a-n that are protruding vertically from the side of flat portion 111 facing the sensors. In at least one embodiment, the flat portion 111 of the door 110, when closed, covers the sensors and/or gets in contact with the top surface of the sensors.

Bumps 112a-n are structures on the side of flat portion 111 facing away from the sensors. In at least one embodiment, bumps 112a-n provide a better grip when closing the door 110, and/or may be present for decoration purposes.

Guiding stubs 113a-b are a pair of stubs protruding vertically from the door 110 for guiding and/or retaining the tubing during insertion. In at least one embodiment, between guiding stubs 113a and 113b a slot is formed (by guiding stubs 113a and b) for holding the tubing, which is inserted into the sensor slots. In at least one embodiment, guiding stubs 113a-b are located on the side of the door 110, and close to the end of the door 110 that is further away from the hinge. In at least one embodiment, the door 110 includes another pair of stubs at the other side of door 110 opposite to the guiding stubs 113a-b, for a better alignment of the tubing to be in parallel to the sensor slots. In other embodiments, the guiding stubs 113a-b may be at other locates so long as the guiding stubs 113a-b align the tubing with the sensor slots and do not interfere with the sensors on pump 101 when the door 110 is closed.

Guiding stubs 113c-d are another pair of stubs that are similar to guiding stubs 113a-b. Guiding stubs 113c-d are located at the other side of door 110 opposite to the guiding stubs 113a-b for aligning and guiding the tubing to be inserted to the sensor slots.

Hinge 114 is an elongated tubular bearing structure that connects the door 110 to the pump 101 on which the door 110 rotates—rotating about the axis of hinge 114 for a limited angle. In at least one embodiment, the door 110 may be able to rotate about 180 degrees with respect to the hinge 114. In at least one embodiment, hinge 114 is a continuous hinge having a cylindrical rod with a circular cross section. The cylindrical rod may be located within tubular cavities at the end of door 110 and/or on pump 101. Hinge 114 may run the entire length of the side of the door 110. In other embodiment, other types of hinges may be used to connect the door 110 to the pump 101. In at least one embodiment, hinge 114 is made from stainless steel, copper, aluminum, nickel, tin, or a mixture of any combination of stainless steel, brass, copper, aluminum, nickel, tin, silver, and/or gold or another conductor, with or without gold and/or silver plating instead of or in addition to any other materials.

Optional lock 115 is a clutch structure for locking and/or retaining the door. In at least one embodiment, optional lock 115 locks the door in a closed position for retaining the tubing in a fully inserted position in the sensor slots.

Sensors 120a-c are three sensor structures for measuring fluid properties and/or detecting bubbles in the tubing that is inserted in sensor slots of the sensors 120a-c. Optionally, sensors 120a-c use optical, mechanical, electrical, and/or sonic techniques for measuring fluid properties (e.g., temperature, fluid level, pressure, velocity, density, flow rate, etc.) and/or detecting presence of bubbles. In one embodiment, at least one of sensors 120a-c includes a bubble detecting mechanism for detecting bubbles in the tubing in order to alert the user. In at least one embodiment, at least one of sensors 120a-c includes an ultrasonic sensor and ultrasound generator. In at least one embodiment, the ultrasound generator sends an ultrasonic signal across the tubing in the sensor slot, and the presence of a bubble, air or foam in the liquid in the tubing will cause an interruption in the acoustical index of refraction modifying the output of the acoustic signal leaving the tube, so that the acoustic signal that leaves the tube when no bubbles are in the tube is different than the acoustic signal that leaves the tube when bubbles are present. In another embodiment, at least one of sensors 120a-c includes a pressure sensor mechanism for measuring the pressure of the fluid in the tubing. In yet another embodiment, sensors 120a-c may include a flow detector for measuring the rate of fluid flow. In yet another embodiment, the sensors 120a-c may include a thermometer, thermister, thermocouple, or other thermo-sensor for detecting temperature of the fluid and/or fluid level. In other embodiments, sensors 120a-c may include other types of sensors and/or for measuring other properties.

In at least one embodiment, sensors 120a-c are able to measure multiple parameters and show various properties of the fluid. In one embodiment, at least two of the sensors 120a-c are the same type of sensors and/or for the same purposes (e.g., in FIG. 1, both of sensors 120a and 120b may be bubble detectors while sensor 120c may be a pressure sensor). In another embodiment, each of sensors 120a-c is a different type and/or for different purposes. In one embodiment, sensors 120a-c may be installed in line with one another in the pump 101. In another embodiment, sensors 120a-c may be installed at different locations of the pump 101. In this specification, whenever one type of sensor is used another type of sensor may be substituted to obtain a different embodiment. Also in this specification which of sensors 120a-c is located at which position may be reversed or switched to obtain a different embodiment. For example, the locations or sequence of a bubble detector and a pressure sensor may be reversed from that which is shown in the drawings to obtain another embodiment. In other embodiments, other numbers and/or types of sensors may be installed in pump 101.

Sensor slots 121a-c are slots or slits in the sensors 120a-c, respectively, for exposing the tubing to sensing elements of the sensors 120a-c in order for the sensors 120a-c to measure the properties of the fluid and/or detect bubbles in the tubing. In at least one embodiment, the door 110 presses the tubing into the sensor slots 121a-c when the door 110 is closed, and the tubing is retained in the sensor slots 121a-c when the sensors 120a-c taking measurements. In at least one embodiment, one or more of the sensor slots 121a-c is slightly smaller than (e.g., 0.030" to 0.050" smaller than) the outside diameter of the tubing so that the tubing has a tight fit so that the one or more sensors is in close proximity to the tubing in order for the at least one of the sensors 120a-c to obtain accurate reading. In another embodiment, one or more of the sensor slots 121a-c has the same width as the outside diameter of the tubing. In another embodiment, at least one of the sensor slots 121a-c has an entrance opening that is even smaller than the tubing, so as to retain the tubing. In one embodiment, each of the sensor slots 121a-c have a different size and/or shape. In another embodiment, at least two of the sensor slots 121a-c may have the same size and/or shape. In the embodiment when the sensors 120a-c are in line with one another, the sensor slots 121a-c may be in line with one another as well. In other embodiments, the sensor slots 121a-c have other shapes or sizes for the tubing to be inserted in.

Openings 123a and 123b are openings at either side(s) of the area where sensors 120a-c are located on the pump 101, for meeting the guiding stubs 113a-b and 113c-d so that the flat portion 111 of door 110 may press the tubing into the sensor slots 121a-c without the protruding guiding subs 113a-b and 113c-d interfering. In at least one embodiment, openings 123a and 123b are part of a chamber within which the sensors 120a-c are installed, with the openings 123a and 123b at the sides of the chamber for the guiding stubs 113a-b and 113c-d to go into.

Bearing 124 is an asymmetrical shaped bearing for placing the tubing in one orientation and preventing (or at least hindering) the tubing from being inserted in a reverse orientation. In at least one embodiment, bearing 124 may be mounted temporarily or permanently on the tubing, and may fit into an opening in the pump 101 in a predetermined orientation. In at least one embodiment, bearing 124, when oriented in a reverse orientation, is not able to fit into the asymmetrical opening, thus preventing the tubing to be placed in a reverse orientation. In at least one embodiment, bearing 124 includes a hat shaped structure, with a rim or disc portion of the hat fitted into a wider side of the opening and a top or cylindrical portion of the hat fitted into a narrower side of the opening, for proper orientation. In FIG. 1, the hat is at the right side of the rim.

In other embodiments, bearing 124 may be in other shapes and/or sizes.

Opening 125 is an opening in the pump 101 for engaging the bearing 124 for proper orientation of the tubing. In at least one embodiment, opening 125 is asymmetrical. In at least one embodiment, opening 125 has a wider semicylindrical side or partial cylindrical side for engaging the rim portion of bearing 124, and a narrower semicylindrical side or partial cylindrical side for engaging the top portion of bearing 124. In one embodiment, opening 125 is located between the pump mechanism and sensors 120a-c. In other embodiments, opening 125 may be in other shapes, sizes, and/or locations.

Guiding concave channels 127a and 127b are guiding structures, such as channels or notches located on either side or both sides of the pump 101 for aligning and guiding the tubing in a proper position so that the tubing may align with the sensor slots and/or the pump mechanism. The tubing rests in guiding concave channels 127a and 127b which the pump is working. In at least one embodiment, guiding concave cannels 127a and/or 127b include a portion (e.g., a half) of a cylindrical concave surface that faces away from the pump 101. The width of the cross section of guiding concave cannels 127a and/or 127b is equal to or greater than the tubing. Guiding concaves 127a and/or 127b are optional. In at least one embodiment, pump 101 includes another number of guiding concaves and/or other structures for aligning and/or retaining the tubing.

Tubing 130 is an elongated flexible tube that is made of plastic or other materials for delivering fluid. In at least one embodiment, tubing 130 has a circular cross section. In at least one embodiment, tubing 130 is made from a soft, resilient (shape restoring) elastomeric material, so as to maintain the circular cross section after repeated squeezing by the pump 101. In at least one embodiment, tubing 130 is made of one of, or any combination of, nitrile rubber (NBR), polyethylene (PET), fluoropolymer, silicone, polyvinyl chloride (PVC), ethylene propylene diene monomer (EPDM), polypropylene, polyurethane, synthetic rubber, natural rubber, etc. In at least one embodiment, tubing 130 is biocompatible and non toxic, and can be used in medical and surgical applications.

Pump mechanism 140 uses a peristaltic mechanism including a rotor and a number of rollers that rotate and compress the tubing within a circular pump casing in order to force fluid to move through the tubing. Pump mechanism 140 will be discussed further in conjunction with FIG. 3A.

Output system 150 may include any one of, some of, any combination of, or all of a monitor system, a handheld display system, a printer system, a speaker system, a connection or interface system to a sound system, an interface system to peripheral devices and/or a connection and/or interface system to a computer system, intranet, and/or internet, for example. In an embodiment, output system 150 may include a display or screen for displaying the results of the sensors, displaying parameters and/or settings of the pump mechanism 140, displaying the time, displaying the results of ongoing or selected programs, displaying alerts, displaying the end of a treatment, and/or displaying errors, for example. In other embodiments, output system 150 also includes a speaker system or sound system for alerting (e.g., by beeping) the user, for example at selected time points, when bubbles or errors are detected, when the tubing is not properly inserted, and/or when the treatment finishes, for example. Output system 150 may also include a user interface for communicating or interacting with the user via keypads, buttons, touch screen functions, voice commands, and/or other means.

Buttons 160a-n are a plurality of buttons on the pump 101 for controlling and operating pump 101, inputting commands, selecting options or functions, etc. In at least one embodiment, buttons 160a-n bear digits, symbols, letters, and/or words (e.g., start, enter, etc), for making the pump easier to operate. In at least one embodiment, some or all of buttons 160a-n have pre-determined functions, optionally indicated by digits, symbols, letters, words on or close to the buttons 160a-n. In at least one embodiment, some or all of the buttons 160a-n are next to a screen of the output system 150, which allows the user to select from the options on the screen by pressing the corresponding buttons that are close to and/or aligned with the options appeared on the screen. In at least one embodiment, the buttons 160a-n are arranged in a block or pad, optionally a numeric keypad or an alphanumeric keyboard. In other embodiments, other numbers of buttons may be arranged in other configurations and/or at other locations.

Figure 2A:
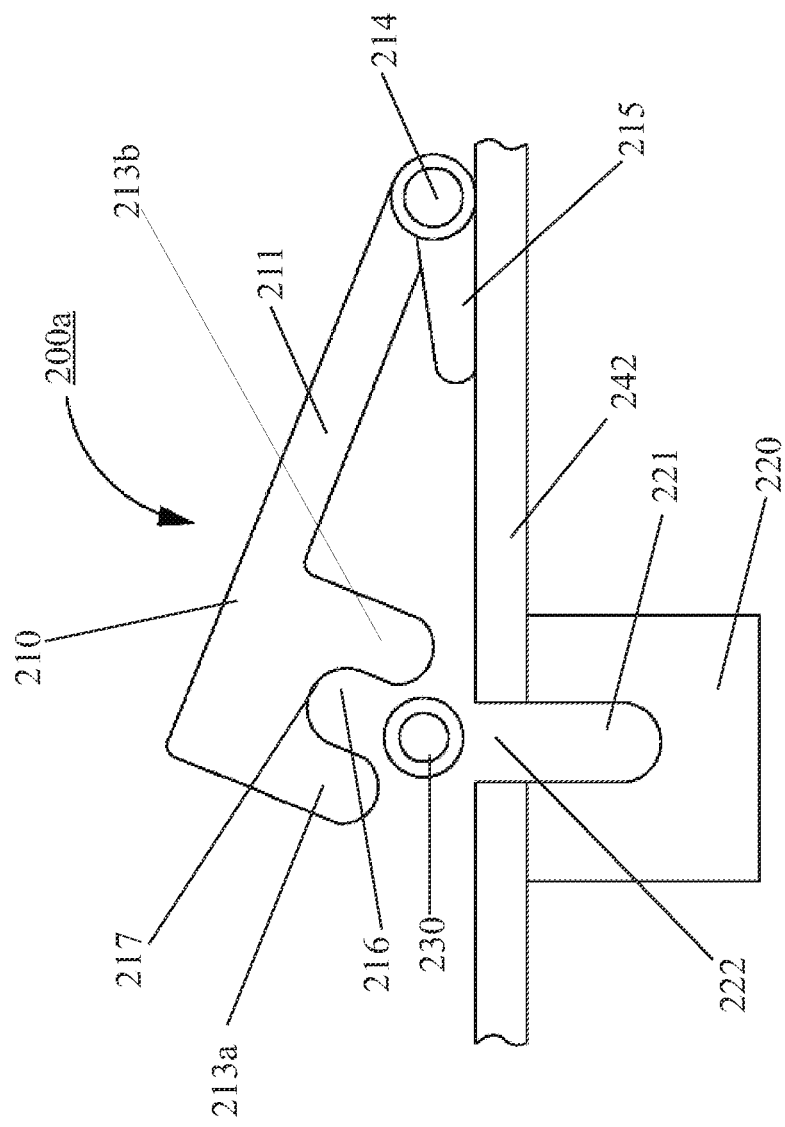
FIG. 2A shows a cross sectional partial view of an embodiment of the pump of FIG. 1.

FIG. 2A shows a cross sectional partial view 200a of an embodiment of the device 100 of FIG. 1. FIG. 2A includes at least a door 210, a flat portion 211, guiding stubs 213a-b, a hinge 214, a optional lock 215, a guiding slot 216, an apex 217, a sensor 220, a sensor slot 221, an entrance opening 222, tubing 230, and a chassis 242. In other embodiments, FIG. 2A may not have all of the elements or features listed and/or may have other elements or features instead of or in addition to those listed.

Door 210, flat portion 211, guiding stubs 213a-b, hinge 214, optional lock 215, guiding slot 216, apex 217, sensor 220, sensor slot 221, entrance opening 222, and tubing 230, are embodiments of door 110, flat portion 111, guiding stubs 113a-b, a hinge 114, optional lock 215, guiding slot 116, one of sensor 120a-c, one of sensor slots 121a-c, and tubing 130, respectively, which were discussed in conjunction with FIG. 1.

FIG. 2A shows that door 210 is hinged to the chassis of pump 101, so that the door 210 may rotate with respect to the hinge axis within a limited range and may be locked. The door 210 includes a pair of guiding stubs facing the sensor, with a guiding slot in-between and formed by the guiding stubs for guiding and/or retaining tubing. When door 210 is closed, the guiding slot aligns the tubing with the entrance of sensor slot. In at least one embodiment, a bar protruding from the flat portion of door 210 connects the guiding slots at both sides of the door 210 for providing a uniform pressure across the length of the tubing and presses the tubing into the sensor slot.

Guiding slot 216 is a slot in-between, and formed by, the guiding stubs 213a-b for guiding and/or retaining the tubing 230 to be inserted to a sensor slot(s). Slot 216 may be referred to as a notch. In at least one embodiment, the user needs to manually insert the tubing 230 into the guiding slot 216 before the tubing 230 is pressed into the sensor slot by the door 210. In one embodiment, the guiding slot 216 is slightly smaller than the outside diameter of the tubing 230, for retaining the tubing 230 when the door 210 is opened, and then the user may remove the tubing 230 from the door 210. In another embodiment, the width of guiding slot 216 is equal to, or slightly larger than, the outside diameter of the tubing 230, so that closing the door 210 pushes the tube 230 snuggly to the bottom of the sensor slot. The tubing 230 is retained in the sensor slot until is manually taken out by the user.

Apex 217 is at the top of guiding slot 216 that may be a part (e.g., a half) of a circular shape (as illustrated in the orientation of FIG. 2). Apex 217 is the portion of the surface of guiding slot 216 that is closest to flat portion 211. In at least one embodiment, apex 217 is below the bottom surface of the flat portion 211 that is facing the sensor. Apex 217 pushes the tubing into the sensor slot. The perpendicular distance between the apex 217 and the bottom surface of the flat portion 211 is discussed below after the discussion of chassis 242. In another embodiment, apex 217 and flat portion 211 are flush with one another. In other embodiments, apex 217 may have other shapes and/or may be other distances away from the flat portion 211.

Sensor 220 may be any one of or any combination of the sensors discussed in conjunction with sensors 120a-c of FIG. 1, for detecting bubbles and/or measuring fluid properties in tubing 230. In at least one embodiment, sensor 220 includes multiple sensors that align with one another so that the sensor slots of the multiple sensors are in the same plane for the tubing 230 to be inserted.

Sensor slot 221 is similar to either one of the sensor slots 121a-c as discussed in conjunction with FIG. 1. In at least one embodiment, the cross section of sensor slot 221 has two linear side walls with a portion (e.g., a half) of a circular bottom wall. In at least one embodiment, sensing elements of the sensor 220 on the side walls close to the bottom of the sensor slot 221, so that the tubing 230 needs to be pushed down to (or close to) the bottom of the sensor slot 221 for a proper reading. In other embodiments, sensor slot 221 has other shapes and/or sizes. In at least one embodiment, the sensor slot 221 aligns with an entrance opening that is formed on a chassis of pump 101. In at least one embodiment, the user needs to pull the tubing 230 out of sensor slot 221 when the tubing 230 is no longer in use.

Entrance opening 222 is an opening or slot on the chassis of pump 101 (FIG. 1) that aligns with the sensor slot 221 for the tubing 230 to be inserted into. In at least one embodiment, the entrance opening 222 has the same width as the sensor slot 221. In another embodiment, the width of the entrance opening 222 is slightly smaller than the sensor slot 221, for retaining the tubing 230 after insertion. In yet another embodiment, the entrance opening 222 is wider than the sensor slot 221 or has another shape that makes it easier to insert the tubing 230 into the sensor slot 221.

Chassis 242 is a top portion of the frame of the pump 101 (FIG. 1) to which the door 210 is connected, via hinge 114/214. In at least one embodiment, hinge 214 is attached or fixed to the top or outer most surface of chassis 242, while the sensor 220 is connected to the bottom surface or an inner surface of chassis 242 from the inside of the pump 101, aligning with the entrance opening 222 that leads to the sensor slot 221.

In at least one embodiment, the perpendicular distance between the apex 217 and the bottom surface of the flat portion 211 is equal to the depth of slot 221 plus the opening thickness of the chassis 242, less the outside diameter of tubing 230.

Figure 2B:
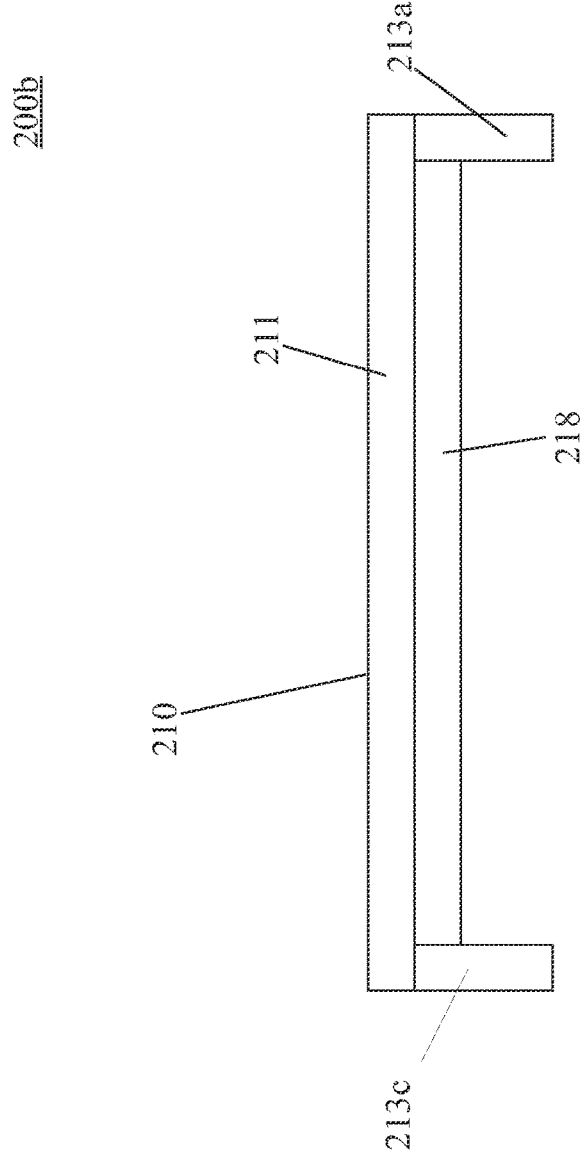
FIG. 2B shows a view of an embodiment of the door of the pump of FIG. 1.

FIG. 2B shows a view 200b of an embodiment of the door 210 of FIG. 2A. FIG. 2B includes at least door 210, flat portion 211, guiding stub 213a, which were discussed in conjunction with FIG. 2A. FIG. 2B also includes guiding stubs 213a and 213c, and a bar 218. In other embodiments, FIG. 2B may not have all of the elements or features listed and/or may have other elements or features instead of or in addition to those listed.

FIG. 2B shows another view of the door 210 that has a flat portion 211 and guiding stubs at both sides of the flat portion 211, and a bar in-between the guiding stubs for pushing the tubing 230 with uniform pressure across the length of the tubing 230 down into the sensor slot 221. The view 200b shows guiding stubs 213a and 213b. Guiding stubs 213a and 213b are on the opposite side of the flat portion 211 with respect to stubs 213c and 213d. Guiding stub 213c and 213d are similar to the pair of guiding stubs 113c-d, which were discussed in conjunction with FIG. 1.

Bar 218 is a rectangular shaped bar that runs across the length of the flat portion 211 and connects the guiding stubs at both sides of the flat portion 211. In at least one embodiment, bar 218 has a concave surface facing the chassis 242. The concave surface of bar 218 is a portion of a surface having a circular cross section making an arc of between 60 degrees and 120 degrees. In another embodiment, the arc of the surface having the circular cross section is between 60 degrees and 180 degrees. In another embodiment, the arc of the surface having the circular cross section is between 90 degrees and 120 degrees. In another embodiment, the arc of the surface having the circular cross section is between 90 degrees and 180 degrees. In another embodiment, the arc of the surface having the circular cross section is between 120 degrees and 180 degrees. The concave surface of bar 218 faces the sensor 220 for providing a uniform support to tubing 230 during insertion. In at least one embodiment, the concave surface of bar 218 has a width that is slightly smaller than the width of sensor slot 221 so as to fit within sensor slot 221 and push tubing 230 into sensor slot 221. In at least one embodiment, the radius of the concave surface of bar 218 is equal to or slightly greater than the radius of the outer surface of tubing 230. In another embodiment, the concave surface of bar 218 may be in different shapes and/or sizes. In at least one embodiment, bar 218 serves to apply a uniform pressure across the length of the tubing 230, so that the tubing 230 is pushed down through entrance opening 222 further into sensor slot 221 to a position where the sensing elements of sensor 220 is located (e.g., to be in contact with the bottom of sensor slot 221 and/or in contact with the sensing elements of sensor 220 on the side wall(s) of the sensor slot). In an embodiment tubing 130 is placed closer to the bottom of sensor slot 221 than to the top of sensor slot 221 (where the opening of sensor slot 221 is located). In at least one embodiment, the height of bar 218 is equal to the perpendicular distance between the apex 217 of guiding slot 216 and the bottom surface of the flat portion 211.

Figure 2C:
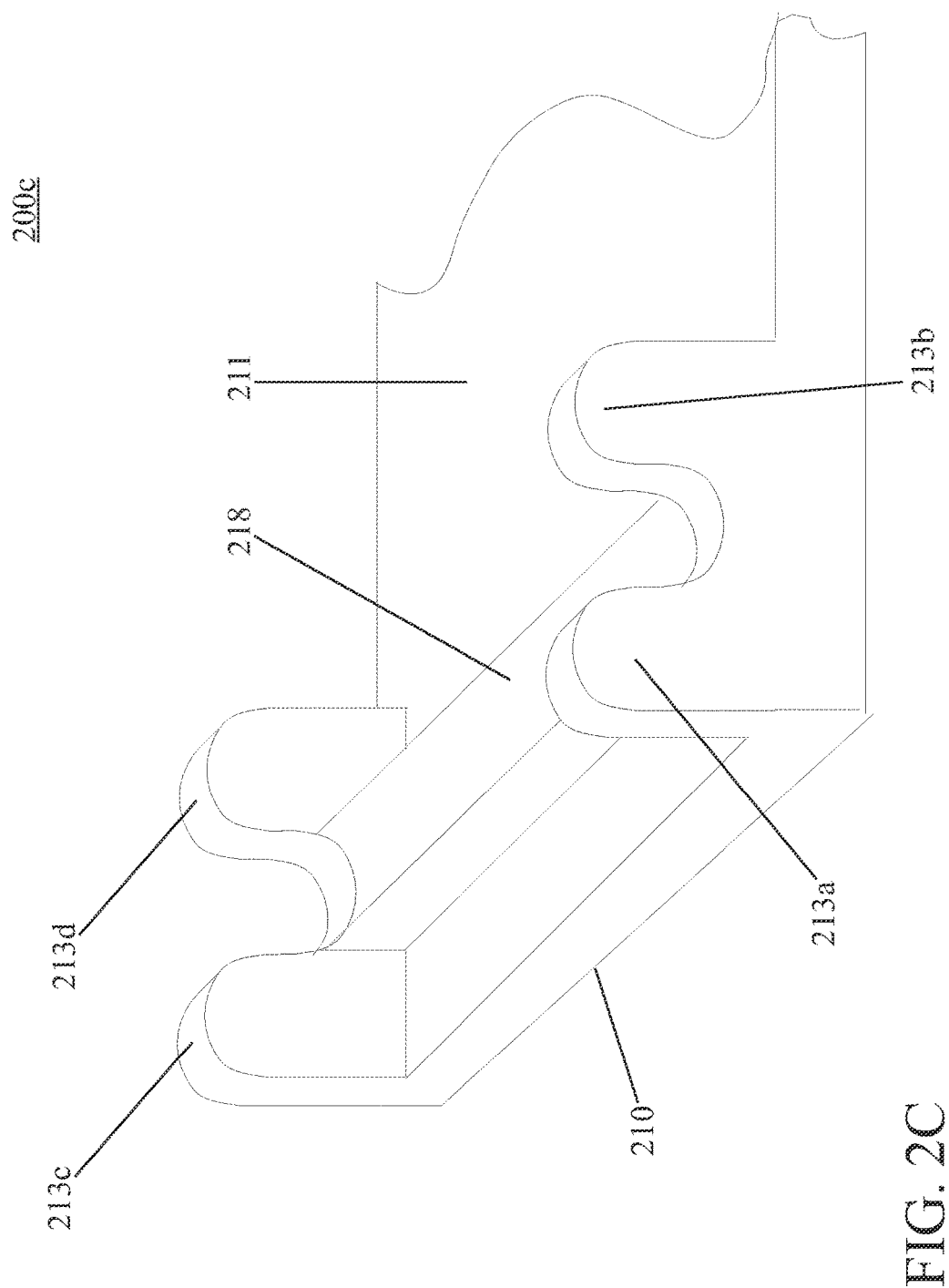
FIG. 2C shows another view of an embodiment of the door of FIG. 1.

FIG. 2C shows another view 200c of an embodiment of the door 210 of FIG. 1. FIG. 2C includes at least door 210, flat portion 211, guiding stubs 213a and 213b, guiding stubs 213c and 213d, and bar 218, which were discussed in conjunction with FIGS. 2A and 2B. In other embodiments, FIG. 2C may not have all of the elements or features listed and/or may have other elements or features instead of or in addition to those listed.

FIG. 2C shows another view of the door 210 with the guiding stubs 213a, 213b, 213c, and 213d facing upwards. In at least one embodiment, the bar 218 runs across the flat portion 211 between guiding stubs 213a and 213b and guiding stubs 213c and 213d, with the concave surface connecting the slots formed by the guiding stubs on the sides of the flat portion 211 for providing a uniform pressure on the tubing to be inserted into the sensor slot(s).

Figure 3A:
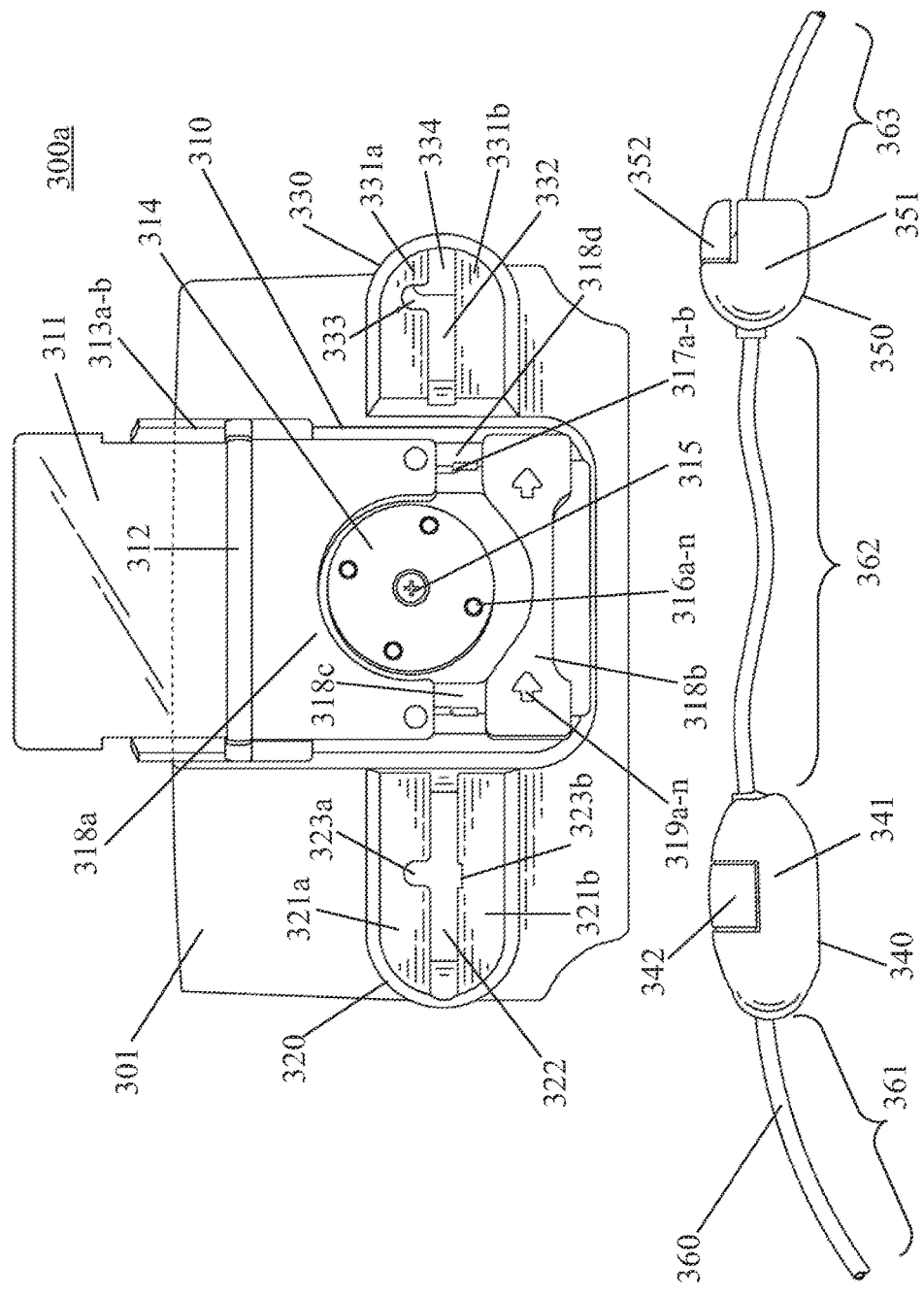
FIG. 3A shows an embodiment of a pump system including two connectors for inserting tubing into irrigation and infusion fluid pumps.

FIG. 3A shows an embodiment of a pump system 300a including two connectors for inserting tubing into irrigation and infusion fluid pumps. Pump system 300a includes at least a chassis 301 of the pump and a pump mechanism 310, which includes at least a door 311, a hinge 312, side panels 313a and 131b, a rotor 314, an axial shaft 315, a plurality of rollers 316a-n, a pair of guiding pins 317a and 317b, a top casing 318a, a bottom casing 318b, a suction side 318c, a discharge side 318d, and arrows 319a-n. Pump system 300a may also include a first receptacle 320, which includes at least a top panel 321a, a bottom panel 321b, a slot 322, an opening 323a, and an opening 323b. Pump system 300a may further include a second receptacle 330, which includes at least a top panel 331a, a bottom panel 331b, a slot 332, an opening 333, and a side panel 334. Pump system 300a may also include a first connector 340 that includes at least a body 341 and a tab 342, and a second connector 350 that includes at least a body 351 and a tab 352. FIG. 3A also includes a tubing 360, which includes an input portion 361, a middle portion 362, and an output portion 363. In other embodiments, FIG. 3A may not have all of the elements or features listed and/or may have other elements or features instead of or in addition to those listed.

FIG. 3A shows an alternative embodiment for inserting tubing into irrigation and infusion fluid pumps, using at least two connectors for holding and/or retaining the tubing. At least one embodiment allows the user to insert the tubing into pump sensor slots by pushing the connectors that hold the tubing into mating receptacles on the pump within which the sensors are installed. In FIG. 3A, the tubing may be removed from the sensor slots by depressing the connectors' latch, which releases the connectors from the receptacles, and then pulling the connectors out of the pump receptacles.

Chassis 301 is a frame and/or other internal supporting structure on which elements of the pump system 300a are mounted and/or connected. In at least one embodiment, chassis 301 is made of plastic. In other embodiments, chassis 301 is made of other materials. In at least one embodiment, a pump mechanism is mounted on the chassis 301. In at least one embodiment, the chassis 301 includes two receptacles, one on each side of the pump mechanism, for engaging two connectors that assist insertion of a tubing. In other embodiments, chassis 301 may include other structures and/or elements.

Pump mechanism 310 is a mechanism for moving fluid that is contained within flexible tubing fitted inside a pump casing. In at least one embodiment, pump mechanism 310 is a positive displacement pump that, on a suction side, captures fluid and pushes (or displaces) that captured fluid to a discharge side in order to move and transport the fluid. In at least one embodiment, pump mechanism 310 is a peristaltic pump having a rotating assembly that includes a rotor with a number of rollers attached to the external circumference of the rotor. The rollers compress the flexible tubing against a stationary casing to push the fluid through the tube. As the rotor turns, the part of the tubing under compression is pinched closed (or occludes) thus forcing the fluid to be pumped to move through the tubing toward the outlet (discharge side) of the pump mechanism 310. In an embodiment, as the rollers move along the length of the tubing, the compressed portion moves with the roller, pushing the fluid along the length of the tubing. Additionally, as the tubing opens to the natural width of the tube, after the passing of the rollers ("restitution" or "resilience") fluid flow is induced to the pump mechanism 310 from the suction side. In at least one embodiment, the pump mechanism 310 may run continuously. In at least one embodiment, the pump mechanism 310 may be controlled to run a pre-determined distance or time, or may be stopped at any point. In at least one embodiment, pump mechanism 310 is used to pump clean/sterile or aggressive fluids as a result of the fluids being enclosed in the tubing without exposure to pump components, thus avoids cross contamination.

Door 311 is a flat panel or plate that is connected to the chassis 301 or pump mechanism 310, via a hinge for covering pump mechanism 310 when the pump mechanism 310 is operating. In at least one embodiment, door 311 aligns with the pump mechanism 310 and may rotate with respect to the hinge for a limited angle. In at least one embodiment, door 311 is made from plastic that may be clear or semi-transparent for users to view pump mechanism 310 when the door 311 is closed. In at least one embodiment, the door 311 may be laid flat on the top surface of the pump mechanism 310 when fully closed. In one embodiment, door 311 may be connected to the chassis 301, via a friction hinge. In another embodiment, door 311 may be connected to a bottom case of pump mechanism 310, via the hinge and/or other structures, so that when the door 311 is closed, the bottom casing is raised up to a position allowing the rollers to compress the tubing. Door 311 may help keep the tubing in a channel under the rotor, while the rotor rotates. In yet another embodiment, the door 311 may be locked and/or retained via a clutch mechanism. In one embodiment, door 311 may include side panels at either side(s). In other embodiments, the door 311 may include other structures.

Hinge 312 is similar to hinge 114. Hinge 312 connects the door 311 to the chassis 301 or to the pump mechanism 310. In at least one embodiment, hinge 312 is a friction hinge which holds the door 311 in a position at any point in the rotational range of the door 311, and allows the user to position and leave the door 311 at an angle that the user desires. In another embodiment, hinge 312 connects the door 311 to structures that further links to the bottom casing of pump mechanism 310, so that closing the door 311 may cause the bottom casing to rise up for proper operation of the pump mechanism 310. In other embodiment, hinge 312 may be other types of hinges or with other structures.

Side panels 313a-b are a pair of panels at both sides of the door 311 for protecting and/or guiding the door 311 when closed. Side panels 313a-b are optional. In at least one embodiment, side panels 313a-b are in contact with on either side of the pump mechanism 310 when the door 311 is closed.

Rotor 314 is a circular disc that rotates to move and transport fluid in flexible tubing that is fitted in-between a portion of the rotor 314 and a circular pump casing. In at least one embodiment, rotor 314 includes a drum shaped body that may rotate with respect to a concentric axial shaft, while a plurality of rollers are installed on the external circumference of rotor 314 for compressing the tubing. In other embodiments, rotor 314 may include other structures or in other shapes. In at least one embodiment, the rotor 314 rotates in a direction that moves the fluid in the tubing from the suction side to the discharge side of the pump mechanism 310. For example, the rotor 314 in FIG. 3A rotates counterclockwise for squeezing the tubing fitted in-between rotor 314 and the bottom casing to move in a direction from the suction side to the discharge side as indicated by a pair of arrows on the bottom casing. In another embodiment, pump system 300a may also include a reverse direction mode, and the rotor 314 may rotate in the reverse direction for moving fluid in the reverse direction (e.g., in the opposite direction as the arrows) when in the reverse direction mode.

Axial shaft 315 is a shaft that connects to, and aligns with, the axis of the rotor 314. Axial shaft 315 bears the radial forces while the rotor 314 rotates with respect to the axial shaft 315. In at least one embodiment, the axial shaft 315 is affixed, optionally via a screw, to the middle of a motor inside the pump chassis. In another embodiment, other fasteners may be substituted for the screw to obtain different embodiments. In other embodiments, axial shaft 315 may include other structures.

Rollers 316a-n are cylindrical elements, that function as wheels or bearing structures, that are rotate-ably connected to the external circumference of the rotor 314 for pressing on the tubing. The fluid is pushed in the same direction as the movement of the rollers that compress the tubing. In at least one embodiment, as the rotor 314 of the pump 301 rotates, rollers 316a-n pass over the tubing, each roller forming a moving compressed section of tubing that pushes the fluid through the tubing in the direction of rotation of the rotor 314. In at least one embodiment, the rollers 316a-n compress the tubing against the bottom pump casing while the tubing is deformed in the gap in-between the roller and the bottom pump casing. In at least one embodiment, the gaps between the rollers 316a-n and the bottom casing determine the degree to which the tubing is squeezed by rollers 316a-n, which further affects pumping performance and the tubing life. In at least one embodiment, the tubing is occluded as a result of being compressed by the roller. In one embodiment, the rollers 316a-n include four rollers, evenly distributed on the external circumference of the rotor 314 (e.g., two nearest rollers are 90° apart with respect to the axial shaft 315). In another embodiment, the rollers 316a-n may include other numbers of rollers (e.g., two rollers that are 180° apart, 8 rollers, 12 rollers, etc). In one embodiment, the rollers 316a-n have fixed locus as the rollers 316a-n turn, keeping the compression on the tubing constant. In another embodiment, the rollers 316a-n are mounted on springs (may be referred to as spring-loaded rollers), and may help overcome the variations in the tubing wall thickness over a broader range to types of tubes.

Guiding pins 317a-b are pins or tabs for guiding and/or retaining the tubing at the suction side and discharge side of the pump mechanism 310, respectively. In at least one embodiment, guiding tabs 317a-b are flexible and/or spring loaded.

Top casing 318a is a top portion of the pump casing for enclosing a part of the rotor 314. In at least one embodiment, top casing 318a is stationary with respect to the chassis 301 and may include a partially circular (e.g., more than a half circle) shaped casing. In at least one embodiment, top casing 318a meets with a bottom casing to form a circular casing that is concentric to the rotor 314. In at least one embodiment, top casing 318a has a cross section that is slightly larger than the diameter of rotor 314 so that the rotor 314 may rotate freely inside top casing 318 with the rollers 316a-n not touching the top casing 318a.

Bottom casing 318b is a bottom portion of the pump casing that may be moved upward for providing a pressure boundary at the bottom of the tubing, against which the tubing in-between the bottom casing 318b and the rotor 314 is compressed by rollers 316a-n when the rotor 314 rotates to transport fluid. In at least one embodiment, the bottom casing 318b includes a partially circular (e.g., less than a half circle) shaped casing that may meet with top casing 318a and form a circular casing to house the rotor 314. In at least one embodiment, bottom casing 318b is connected via levers to the door 311, so that when the door 311 is closed the levers cause the bottom casing 318b to rise up, while opening the door 311 causes the bottom casing 318b to lower down. In at least one embodiment, the gap between the rollers 316a-n and the bottom casing 318b, when the bottom casing 318b is raised up, is smaller than the outside diameter of the tubing and equal to or slightly greater than twice the thickness of tubing wall, so that the rollers 316a-n may squeeze the tubing against the bottom casing 318b for transporting fluid. In other embodiments, bottom casing 318b may include other structures and/or shapes.

Suction side 318c is the side of the pump mechanism 310 from which the fluid is drawn to the pump mechanism 310, while a volume of fluid is pushed forwards by at least one of the rollers 316a-n toward the discharge side.

Discharge side 318d is the side of the pump mechanism 310 at which the fluid in the tubing flows out of the pump mechanism 310 (as a result of the rollers 316a-n compressing the tubing and pushing the fluid to the discharge side 318d).

Arrows 319a-n are a plurality of arrows that are printed or molded on the bottom casing 318b for indicating the direction of the fluid movement. In at least one embodiment, arrows 319a-n includes two arrows, one on the suction side 318c and the other on the discharge side 318d, both pointing to the direction of the discharge side 318d. In another embodiment, other numbers of arrows may be included at other locations of the pump mechanism 310 or on the chassis 301. In at least one embodiment, the rotor 314 may rotate in the same direction indicated by arrows 319a-n. In another embodiment, rotor 314 may also have a reverse mode in which rotor 314 rotates in a reverse direction when the user instructs the pump to reverse the direction of flow of the fluid.

First receptacle 320 is a structure for engaging a first connector that retains tubing for inserting into a sensor slot(s) located within a slot of the first receptacle 320. In at least one embodiment, the first receptacle 320 is located at the suction side of the pump mechanism 310. First receptacle 320 may have two parallel sides at the top and bottom, a circular (e.g., semicircular) side opposite to the pump mechanism 310 and a linear side close to the suction side of the pump mechanism 310. In another embodiment, the first receptacle 320 may be located at the discharge side or other locations. In at least one embodiment, a sensor(s) is installed at the back side of the first receptacle 320 from inside the chassis 301, so that the sensor slot(s) of the sensor(s) aligns with the slot of the first receptacle 320 and therefore the sensor also aligns with the tubing retained in the first connector (the first connector is be inserted into first receptacle 320). In at least one embodiment, the first receptacle 320 includes openings that mate with a tab of the first connector so that the first connector may be locked in, and released from, the first receptacle 320. In at least one embodiment, the first receptacle 320 is molded or shaped in a way that only the structure of the first connector may be inserted into the first receptacle 320, and the first connector may only be inserted into first receptacle 320 in one direction. Connectors with other structures cannot be properly inserted into the first receptacle 320. In at least one embodiment, a clear visual and/or audible indication is provided (e.g., by the first connector or by the pump) to the user that the tubing retained by the first connector is fully and properly inserted into the sensor slot(s) within the first receptacle 320. In another embodiment, the first receptacle 320 may include electrical sensor, optical sensor, or other means for detecting that the first connector is properly and fully inserted. For example, the first connector may include a conductor that completes a circuit causing an indicator to indicate the proper insertion of the first connector into first receptacle 320. Similarly, the first connector may break an optical beam when properly inserted into the first receptacle 320. In at least one embodiment, the detection means has the advantage of providing a means for the pump to ensure that the tubing is properly inserted independent of the user. For example, the detection means may prevent the user from bypassing the use of the first connector, installing the tubing in a reverse direction, or using incompatible tubing sets that do not have the proper mating connector.

In at least one embodiment, the first receptacle 320 may include a top panel 321a, a bottom panel 321b, a slot 322, an opening 323a, and an opening 323b. In other embodiments, first receptacle 320 may not have all of the elements or features listed and/or may have other elements or features instead of or in addition to those listed.

Top panel 321a is a panel that covers the top portion within the first receptacle 320. In at least one embodiment, the top panel 321a includes an opening facing the bottom portion for engaging the latch of the first connector.

Bottom panel 321b is a panel that covers the bottom portion within the first receptacle 320. In at least one embodiment, the bottom panel 321a includes an opening facing the opening of the top panel 321a for engaging the latch of the first connector.

Slot 322 is a slot or opening in-between the top panel 321a and the bottom panel 321b, within which a portion of the first connector is inserted and engaged.

Opening 323a is an opening at the top panel 321a facing the bottom panel 321b for engaging a portion of the latch of the first connector. In at least one embodiment, the opening 323a is in the middle of the first panel 321a and has a semicircular top wall and two linear side walls.

Opening 323b is an opening at the bottom panel 321b facing the opening 323a of the top panel 321a. In at least one embodiment, the opening 323b is of different size and/or shape than the opening 323a for proper orientation of the first connector.

Second receptacle 330 is similar to the first receptacle 320 except that the second receptacle 330 is of different shape than the first receptacle 320 for engaging a second connector, and is located at the discharge side of the pump mechanism 310. In at least one embodiment, the second receptacle 330 has two parallel sides at the top and bottom that are shorter than the top and bottom sides of the first receptacle 320, a semicircular side opposite to the pump mechanism 310, and a linear side close to the discharge side of the pump mechanism 310. In this specification, which one of first receptacle 320 and second receptacle 330 is at which of suction side and discharge side can be reversed to obtain different embodiments. In at least one embodiment, a sensor(s) may be installed to the second receptacle 330 with a sensor slot(s) aligning with a slot within the second receptacle 330. In other embodiments, the second receptacle 330 may include other structures or shapes, and/or may be mounted at other locations on the chassis 301.

Top panel 331a is a panel that covers the top portion within the second receptacle 330. In at least one embodiment, the top panel 331a includes an opening facing the bottom portion for engaging a latch of the second connector.

Bottom panel 331b is a panel that covers the bottom portion within the second receptacle 330.

Slot 332 is a slot or opening in-between the top panel 331a and the bottom panel 331b, within which a portion of the second connector is inserted and engaged.

Opening 333 is an opening at the top panel 331a facing the bottom panel 331b for engaging the latch of the second connector. In at least one embodiment, the opening 333 is close to the semicircular side of the second receptacle 330 and has a circular top wall and two linear side walls for proper orientation of the second connector.

Side panel 334 is a panel that covers the semicircular side within the second receptacle 330. In at least one embodiment, the side panel 334 is connected to the top panel 331a and bottom panel 331b. In at least one embodiment, the side panel 334 is not at the same plane as the top panel 331a and/or the bottom panel 331b.

First connector 340 is a structure that holds and/or guides the tubing and engages the first receptacle 320 for inserting and/or retaining the tubing into sensor slot(s) within the first receptacle 320. In at least one embodiment, the first connector 340 is molded with plastic or other materials. In at least one embodiment, the first connector 340 has an oval shaped base from the view of FIG. 3A. In at least one embodiment, the first connector 340 includes a portion that connects to a tab that mates with the slot 322 of the first receptacle 320 and retains the first connector 340 within the first receptacle 320. In at least one embodiment, the tubing may be removed from sensor slots by pressing the latch and pulling the first connector 340 out of the first receptacle 320. In at least one embodiment, the structure of the first connector 340 only allows the first connector 340 to be inserted into the first receptacle 320 in one direction, but not in the reverse direction and not in the second receptacle 330. The structure of the first connector 340 will be discussed in FIGS. 5A-S. In other embodiments, the first connector 340 may include other structures or other shapes.

Body 341 is the body portion of the first connector 340 for guiding and/or supporting the tubing to be inserted into the sensor slot(s) in the first receptacle 320. Optionally, the body 341 may include at least an arrow points at the same direction as the flow of fluid when the first connector 340 is correctly inserted. In at least one embodiment, the body 341 is partially connected to a tab on one side such that the tab may be pressed toward the body 341 in a limited range in order to disengage the first connector 340 from the first receptacle 320.

Tab 342 is a latch structure on one side of the first connector 340 for retaining in or disengaging from the first receptacle 320. In at least one embodiment, the tab 342 is partially connected to and biases away from the body 341, so that when the first connector 340 is pushed into the slot 322 the tab 342 engages the slot 322 and lock the first connector 340 in the first receptacle 320. Tab 342 is made from a resilient material that tends to keep the shape of the material. In at least one embodiment, the tab 342 may be pressed toward the body 341 to disengage the first connector 340 from the first receptacle 320 so that the first connector 340 and the tubing may be removed from the slot 322 and/or the sensor slot(s) in the first receptacle 320. In at least one embodiment, the tab 342 is molded using plastic or other materials. In another embodiment, the tab 342 may be spring loaded, or has other mechanisms for locking and releasing the first connector 340.

Second connector 350 is similar to the first connector 340 except that the second connector 350 has a different shape than the first connector 340, such that second connector 350 engages the second receptacle 330. In at least one embodiment, the second connector 350 has a base portion that has a shape that appears oval from the view of FIG. 3A, and has a tab on a corner that mates with the slot 332 for locking the second connector 350 in the second receptacle 330. In at least one embodiment, the structure of the second connector 350 only allows the second connector 350 to be inserted into the second receptacle 330 in one direction, but does not allow second connector 350 to be inserted in a reverse direction or in the first receptacle 320. In this specification, when the tubing is retained or held by more than one connector, the connectors shall each be of a shape and size that prevents each connector from mating with the other connector's receptacle. In at least one embodiment, which pair of connector and receptacle is at which location can be reversed to obtain a different embodiment.

Body 351 is similar to the body 341. Body 351 is a portion of the second connector 350 for engaging the second receptacle 330. In at least one embodiment, body 351 and body 341 are in different shapes and/or sizes.

Tab 352 is similar to tab 342. Tab 352 is located on one corner of the second connector 350 for locking or disengaging the second connector 350 in the second receptacle 330. In other embodiments, tab 352 may include other structures or shapes.

Tubing 360 is flexible tubing similar to the tubing 130 as discussed in conjunction with FIG. 1. In at least one embodiment, tubing 360 is held or retained by the first connector 340 and the second connector 350 for inserting the tubing into sensor slots within the first receptacle 320 and/or the second receptacle 330, respectively. In at least one embodiment, the portion of the tubing 360 between the first connector 340 and the second connector 350 is fitted into the pump mechanism 310 for transporting fluid in the direction indicated by arrows 319a-n.

Input portion 361 is a portion of tubing 360 leading to the suction side 318c of the pump mechanism 310 for providing an input of fluid to the pump mechanism 310. In at least one embodiment, the input portion 361 meets with the first connector 340 and the fluid flows into the tubing that is held and supported by the first connector 340.

Middle portion 362 is a portion of tubing 360 for fitting into the pump casing 318 of pump mechanism 310 to be compressed by the rollers 316a-n in order to force the fluid in the middle portion 362 to move toward the discharge side 318d. In at least one embodiment, the middle portion 362 is the portion of tubing 360 that is located between the first connector 340 and the second connector 350, and the fluid in the middle portion 362 flows toward the discharge side 318d.

Output portion 363 is a portion of tubing 360 within which the fluid runs out of discharge side 318d of the pump mechanism 310. In at least one embodiment, the output portion 363 meets with the second connector 350 and fluid flows from the tubing that is held and supported by the second connector 350 to the output portion 363.

FIG. 3B shows another view of an example of rotor assembly 300b. Rotor assembly 300b may include rotor 314, axial shaft 315, and rollers 316a-n. In other embodiments, rotor assembly 300b may not include all of the components of FIG. 3B and/or may include other components in addition to, on instead of those listed in FIG. 3B.

Rotor 314, axial shaft 315, and rollers 316a-n were discussed in conjunction with FIG. 3A. However, FIG. 3B shows how rollers 316a-n (in FIG. 3B, four rollers 316a-d are shown as an example) protrude from rotor 314. During operation, rotor 314 is on the side of the tubing 360, while rollers 316a-n are on top of the tubing 360, so that rotor 314 does not touch the tubing 360 whereas rollers 316a-n, when at the bottom third of arc or bottom quarter of arc of rotor 314, press down on the tubing 360, compressing the tubing 360.

Figure 4:
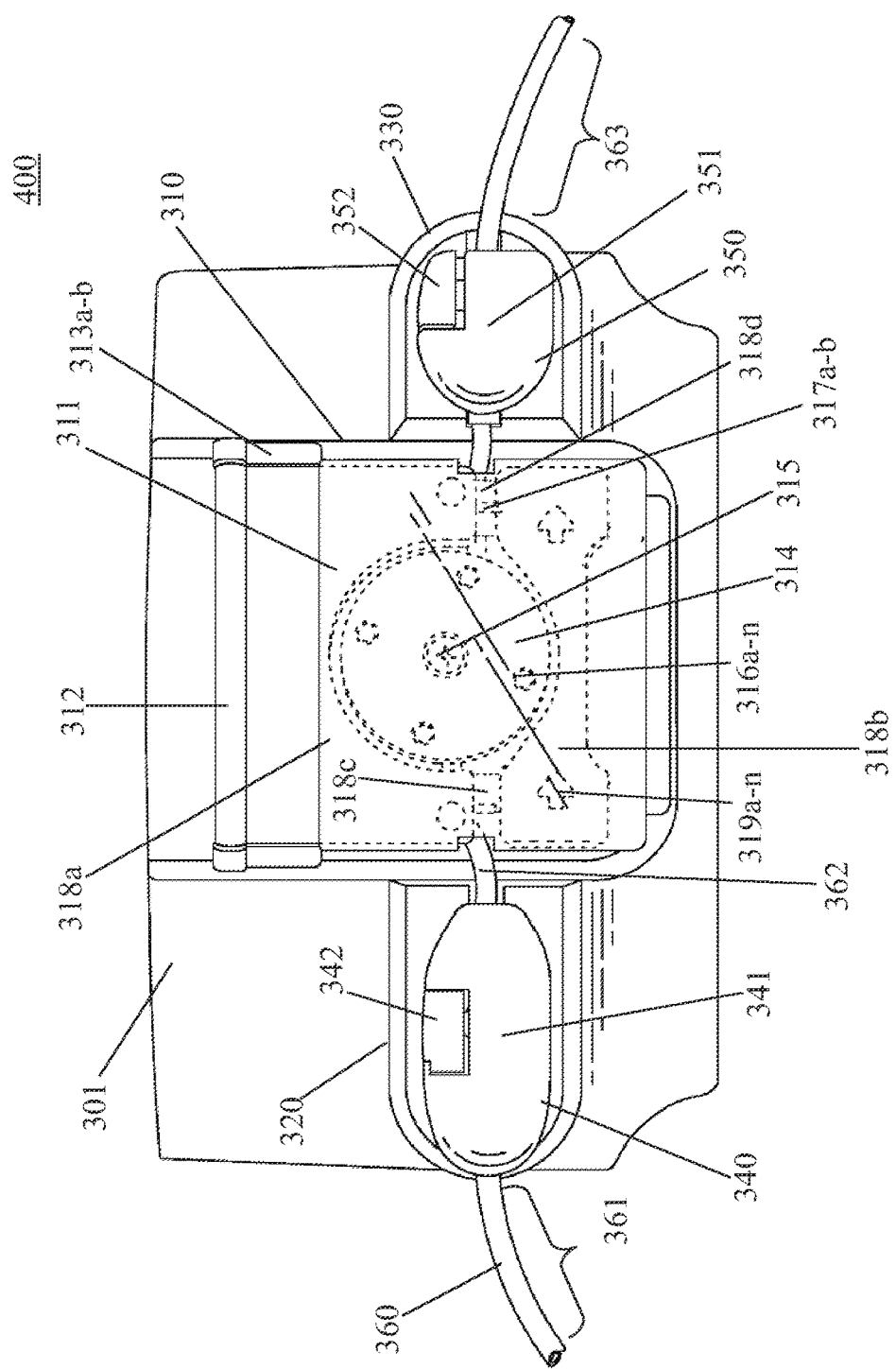
FIG. 4 shows another view of an embodiment of the pump system of FIG. 3A, in which the connectors are connected to the pump system.

FIG. 4 shows another view 400 of an embodiment of the pump system of FIG. 3A, in which the connectors are connected to the pump. FIG. 4 includes at least chassis 301, pump 310, door 311, hinge 312, side panels 313a-b, rotor 314, axial shaft 315, rollers 316a-n, guiding pins 317a-b, top casing 318a, bottom casing 318b, suction side 318c, discharge side 318d, arrows 319a-n, first receptacle 320, second receptacle 330, first connector 340, body 341, tab 342, second connector 350, body 351, tab 352, tubing 360, input portion 361, middle portion 362, and output portion 363, which were discussed in conjunction with FIG. 3A. In other embodiments, FIG. 4 may not have all of the elements or features listed and/or may have other elements or features instead of or in addition to those listed.

FIG. 4 shows the manner in which the first connector 340, the second connector 350, and tubing 360 connect to pump system 300. Specifically, the first connector 340 and the second connector 350 are securely attached to the first receptacle 320 and the second receptacle 330, respectively. Similarly, the middle portion 362 of tubing 360 is fitted into the pump mechanism 310.

Figure 5A:
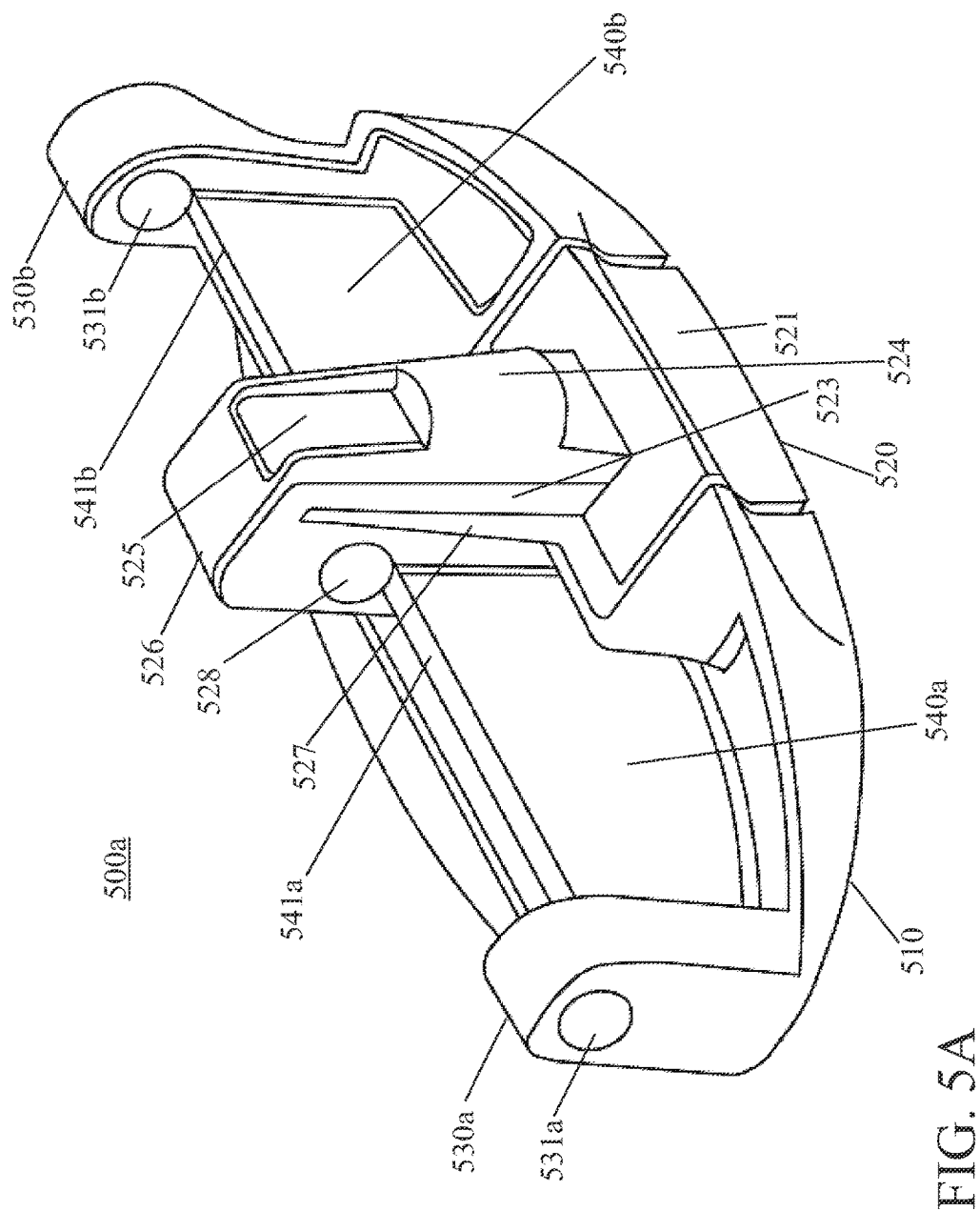
FIG. 5A shows an embodiment of a first connector of FIG. 3A.

FIG. 5A shows an embodiment of a first connector 500a that may be used as first connector 340 of FIG. 3A. First connector 500a includes at least a body 510, a tab 520, a tab base 521, a tab member 523, a protrusion 524, an indent 525, a middle member 526, a space 527, a hole 528, a side member 530a, a hole 531a, a side member 530b, a hole 531b, a pair of panels 540a and 540b, and panel edge 541a and 541b. In other embodiments, first connector 500a may not have all of the elements or features listed and/or may have other elements or features instead of or in addition to those listed.

In at least one embodiment, FIG. 5A shows a view of the elements at the bottom of the base of first connector 340 of FIG. 3, similar to a view when the first connector 340 is flipped to lie on the base. In at least one embodiment, the connectors (e.g., the first connector 340 and the second connector 350 of FIG. 3A) includes structures for guiding and supporting the tubing 360 and position the tubing 360 for proper insertion into sensor slots in the mating receptacles.

Body 510 and tab 520 may be embodiments of the body 341 and tab 342, which were discussed in conjunction with FIG. 3A.

Tab base 521 is the base portion of the tab 520. In at least one embodiment, tab base 521 includes a concave side on the side facing away from the body 510, for providing a better grip when the user presses the tab base 521 to release the tab 520 from the first receptacle 320.

Tab member 523 is a structure that protrudes from the tab base 521 and connects to a middle member of the body 510 at the far end away from the tab base 521. In at least one embodiment, at least the portion connecting tab member 523 and middle member of body 510 is flexible with good fatigue life, and biases the tab member 523 away from the body 510. In at least one embodiment, a portion or all of the tab member 523 is made from resilient plastic, which is flexible enough to allow the user to press the tab 520 toward the body 510, and then return to the original position when the user releases the tab 520. In at least one embodiment, the first connector 500a is pushed into the first receptacle 320 and the tab member 523 is inserted into opening 323a, with a protrusion on the tab member 523 for engaging the opening 323a and for retaining the first connector 500a in pump system 300. In at least one embodiment, when the tab base 521 is pressed, the tab member 523 is bent toward the middle member of body 510 so that the protrusion on the tab member 523 is bent away from the opening 323a, and as a result the first connector 500a may be removed from the first receptacle 320. In at least one embodiment, the tab member 523 is made of plastic.

Protrusion 524 is a tab on the side of the tab member 523 opposite to the middle member of the body 510, for engaging the opening 323a and retaining the first connector 340 in the first receptacle 320. In at least one embodiment, protrusion 524 has a cross section that is a part (e.g., a half) of a circular shape, parallel to the surface of the tab base 521. In at least one embodiment, the side of protrusion 524 facing the tab base 521 has a sharp edge for preventing the protrusion 524 from slipping off from the opening 323a when the tab 520 is engaged with the slot 322. In at least one embodiment, the side of protrusion 524 faces away from the tab base 521 and has a blunt edge for an easier insertion of protrusion 524 into the opening 323a. In at least one embodiment, when the tab base 521 is pressed, the protrusion 524 moves towards the body 510 and the protrusion 524 may be released from the opening 323a.

Indent 525 is an indent on the tab member 523 between the protrusion 524 and the end of tab member 523 that is connected to body 510. Indent 525 is optional. In at least one embodiment, indent 525 is molded to keep a uniform thickness.

Middle member 526 is a structure of the body 510 that protrudes from the middle of the body 510 and connects to the tab member 523 at the end facing away from the tab base 521, and in at least one embodiment, middle member 526 includes a hole for holding and/or retaining the tubing 360.

Space 527 is a space in-between the tab member 523 and the middle member 526. In at least one embodiment, space 527 may vary when the tab 520 is pressed or released.

Hole 528 is a hole in the middle member 526 close to the end that is connected to the tab member 523, for holding and/or retaining the tubing 360. In at least one embodiment, hole 528 aligns with the longitudinal axis of the first connector 500a and includes a cross section that is slight larger than the outside diameter of the tubing 360.

Side member 530a is a structure protruding from one end of the body 510 in parallel to the middle member 526 for guiding and/or supporting the tubing 360. In at least one embodiment, side member 530a includes a hole that is coaxial with hole 528.

Hole 531a is a hole in the end of side member 530a coaxial with the hole 528, for holding and/or retaining the tubing 360. In at least one embodiment, hole 531a has a cross section that is slight larger than the outside diameter of the tubing 360.

Side member 530b is similar to the side member 530a. Side member 530b is on the other end of the body 510 opposite to the side member 530a. In at least one embodiment, side member 530b includes a different shape and/or size than side member 530a for proper orientation of the first connector 500a.

Hole 531b is similar to hole 531a. Hole 531b is in the end of member 530b. In at least one embodiment, hole 531a and 531b have different length.

Panels 540a and 540b are panels or plates that connect the middle member 526 with side member 530a and 530b, respectively, for supporting and pushing the tubing 360 into sensor slot(s) within the first receptacle 320. In at least one embodiment, as shown in FIG. 5A the top surfaces of panels 540a and 540b connect the bottom surfaces of the holes 528, 531a, and 531b in order not to block the holes, while the tubing 360 across the length is supported by the holes 528, 531a, and 531b and the top surface of the panels 540a and 540b.

Panel edge 541a and 541b are the top surfaces of panels 540a and 540b, respectively, for supporting the tubing 360 and uniformly insert the tubing 360 into the sensors slot(s) within the first receptacle 320. In at least one embodiment, the panel edge 541a and 541b are a part of a circular shape that is concentric to and extends from the holes 528, 531a, and 531b, so that the tubing 360 with a slightly smaller or equal outside diameter may receive a uniform pressure around a portion along the tubing 360 without the tubing 360 slipping off the panel edge 541a and 541 b.

Figure 5B:
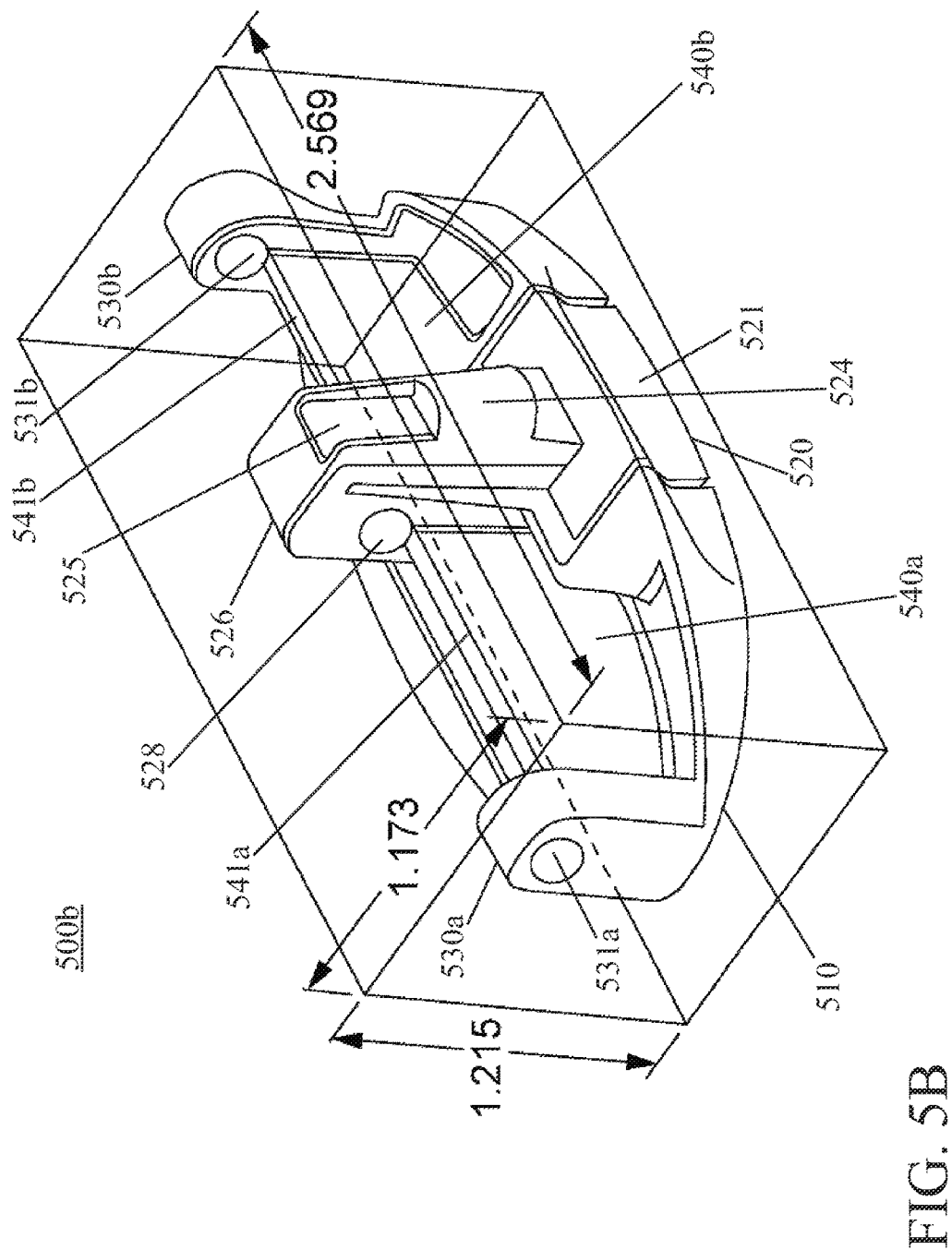
FIG. 5B shows an embodiment of the dimensions of the first connector of FIG. 5A.

FIG. 5B shows an embodiment of the dimensions 500b of the first connector 500a of FIG. 5A. FIG. 5B includes at least body 510, tab 520, tab base 521, protrusion 524, indent 525, middle member 526, hole 528, side member 530a, hole 531a, side member 530b, hole 531b, panels 540a and 540b, and panel edge 541a and 541b, which were discussed in conjunction with FIG. 5A. In other embodiments, FIG. 5B may not have all of the elements or features listed and/or may have other elements or features instead of or in addition to those listed.

In general, the dimensions of the elements shown in FIGS. 5B, 5D, 5F-L, 5N-S, and 8E-H are in inches and the angles are in degrees. FIGS. 5B, 5D, 5F-L, 5N-S, and 8E-H show examples of the embodiments of the invention, and the invention is not limited to the examples and dimensions shown in FIGS. 5B, 5D, 5F-L, 5N-S, and 8E-H. It should be understood that modifications may be made without departing from the essential teachings of the invention. In general, the dimensions of any particular feature shown in FIGS. 5B, 5D, 5F-L, 5N-S, and 8E-H may be varied by at least ±10%, as long as corresponding features with interdependent dimensions are varied in a similar manner. For example, components that are intended to fit snugly within one another need to vary together so that those components still fit within one another, snugly. In other embodiments other dimensions may be used that are outside of the ±10% tolerances or ranges of the dimensions shown in FIGS. 5B, 5D, 5F-L, 5N-S, and 8E-H. For example, the length of the first connector 500 may be within a range of 2.569±0.257 inches.

Figure 5C:
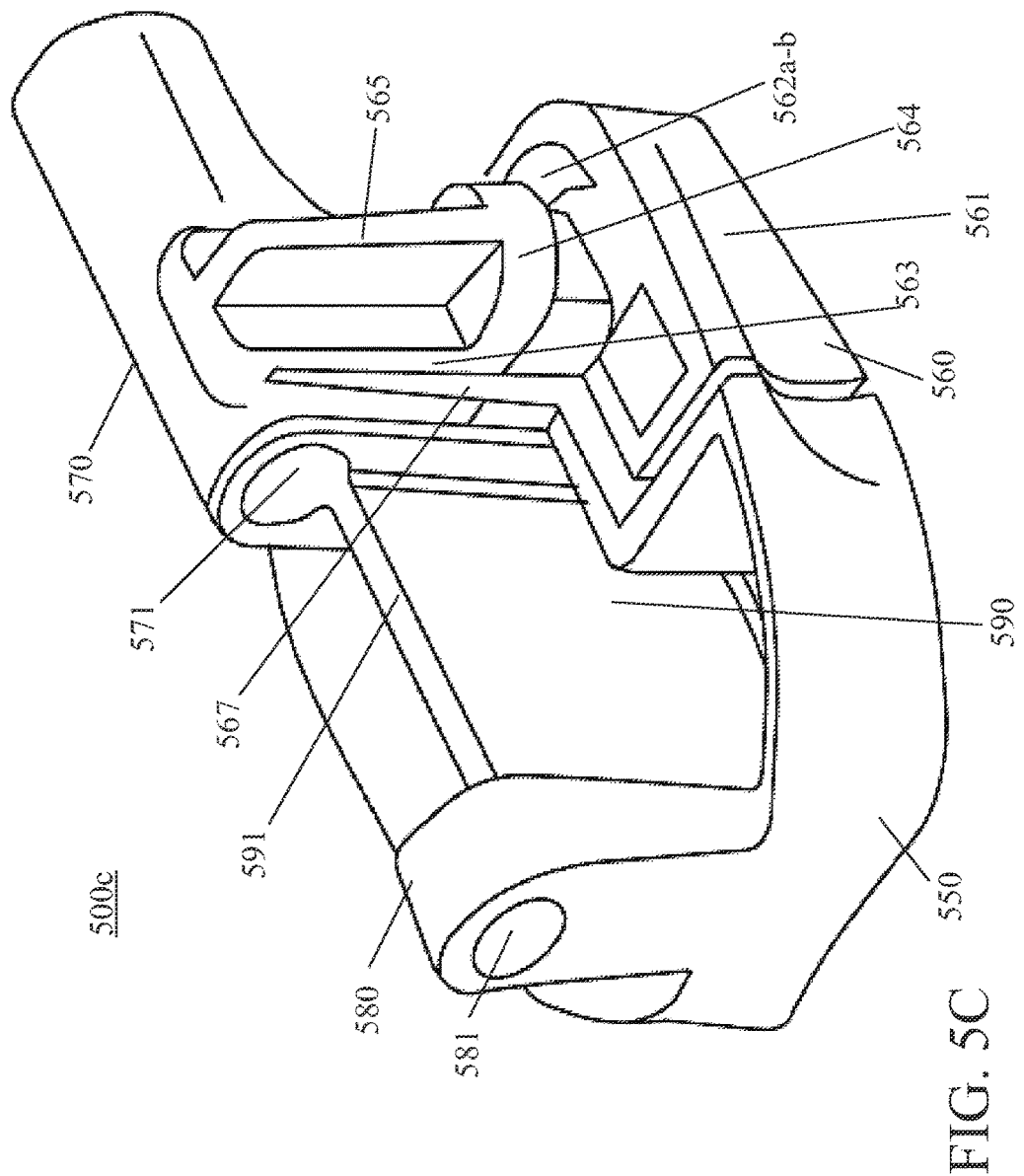
FIG. 5C shows an embodiment of a second connector of FIG. 3A.

FIG. 5C shows an embodiment of a second connector 500c of FIG. 3A. Second connector 500c includes at least a body 550, a tab 560, a tab base 561, holes 562a-b, a tab member 563, a protrusion 564, an extended portion 565, a space 567, a side member 570, a hole 571, a side member 580, a hole 581, a panel 590, and a panel edge 591. In other embodiments, second connector 500c may not have all of the elements or features listed and/or may have other elements or features instead of or in addition to those listed.

Body 550 and tab 560 may be embodiments of the body 351 and tab 352, which were discussed in conjunction with FIG. 3A.

Tab base 561 is similar to the tab base 521 that was discussed in conjunction with FIG. 5A. The tab base 561 is the base of the tab 560 and is in a different shape than tab base 521.

Holes 562a-b are a pair of holes for molding purposes. Holes 562a-b are Optional.

Tab member 563 is similar to tab member 523 that was discussed in conjunction with FIG. 5A. Tab member 563 protrudes from the tab base 561 for engaging opening 333 in the second receptacle 330. In at least one embodiment, tab member 563 connects to a side member of the body 550 at the far end away from the tab base 561 and includes a different shape and/or size than the tab member 523, so that one of latch members 523 and 563 cannot be inserted into the other's mating slot.

Protrusion 564 is similar to the protrusion 524 that was discussed in conjunction with FIG. 5A. Protrusion 564 meets with an extended portion at the side opposite to the tab base 561 and engages the slot 333 of the second receptacle 330 (FIG. 3A). In at least one embodiment, protrusion 564 may be in a different shape and/or size than protrusion 524.

Extended portion 565 is a panel or plate that extends vertically from the tab member 563 and meets the protrusion 564, for properly guiding and engaging the opening 333 of the second receptacle 330 (FIG. 3A).

Space 567 is a space in-between the tab member 563 and a side member and may vary when the tab 560 is pressed or released.

Side member 570 is a structure protruding vertically from one end of base of the body 550 for guiding and/or supporting the tubing 360. In at least one embodiment, side member 570 includes a hole at the end away from the tab base 561.

Hole 571 is a hole at the end of the side member 570 for holding and/or retaining the tubing 360 (FIG. 3A). In at least one embodiment, hole 571 includes a cross section that is slight larger than the outside diameter of the tubing 360.

Side member 580 is similar to side member 570. Side member 580 protrudes vertically from the other end of the body 550 and is in a different shape than side member 570, for proper orientation of the tubing 360 for insertion. In at least one embodiment, side member 580 includes a hole at the end away from the tab base 561.

Hole 581 is similar and concentric to hole 571, except that the length of hole 581 may be different than that of hole 571.

Panel 590 is similar to either one of the panels 540*a* and 540*b* that were discussed in conjunction with FIG. 5A. Panel 590 connects side members 570 and 580 for supporting the tubing 360 to be inserted into sensor slot(s) within the second receptacle 330.

Panel edge 591 is similar to either one of the panel edge 541*a* and 541*b* that were discussed in conjunction with FIG. 5A. Panel edge 591 connects the bottom surfaces of holes 571 and 581 for uniformly insert the tubing 360 into the sensors slot(s) within the second receptacle 330.

Figure 5D:
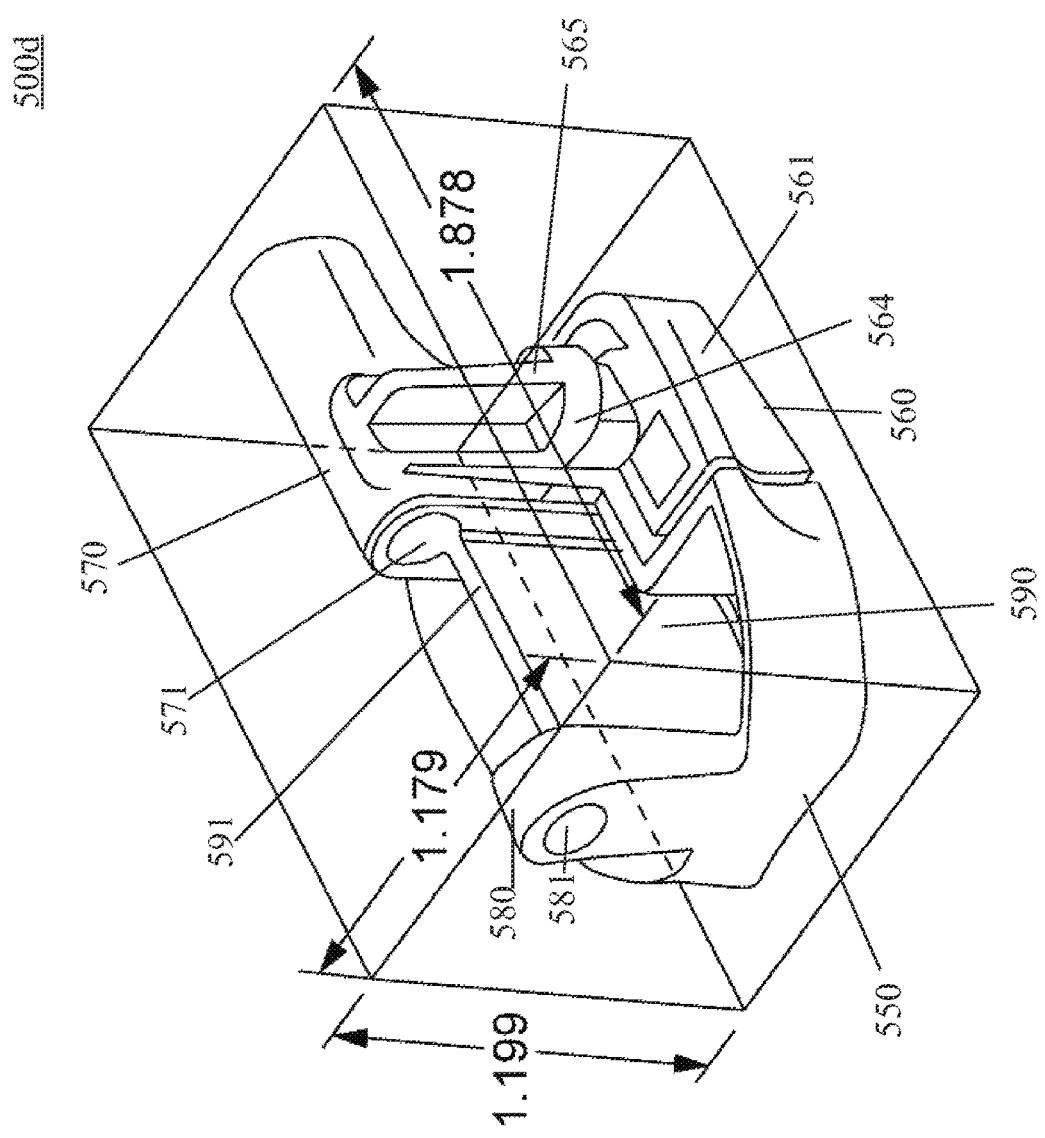
FIG. 5D shows an embodiment of the dimensions of the second connector of FIG. 5C.

FIG. 5D shows an embodiment of the dimensions 500*d* of the second connector 500*c* of FIG. 5C. FIG. 5D may include body 550, tab 560, tab base 561, protrusion 564, extended portion 565, side member 570, hole 571, side member 580, hole 581, panel 590, and panel edge 591, which were discussed in conjunction with FIG. 5C. In other embodiments, second connector 500*d* may not have all of the elements or features listed and/or may have other elements or features instead of or in addition to those listed.

Figure 5E:
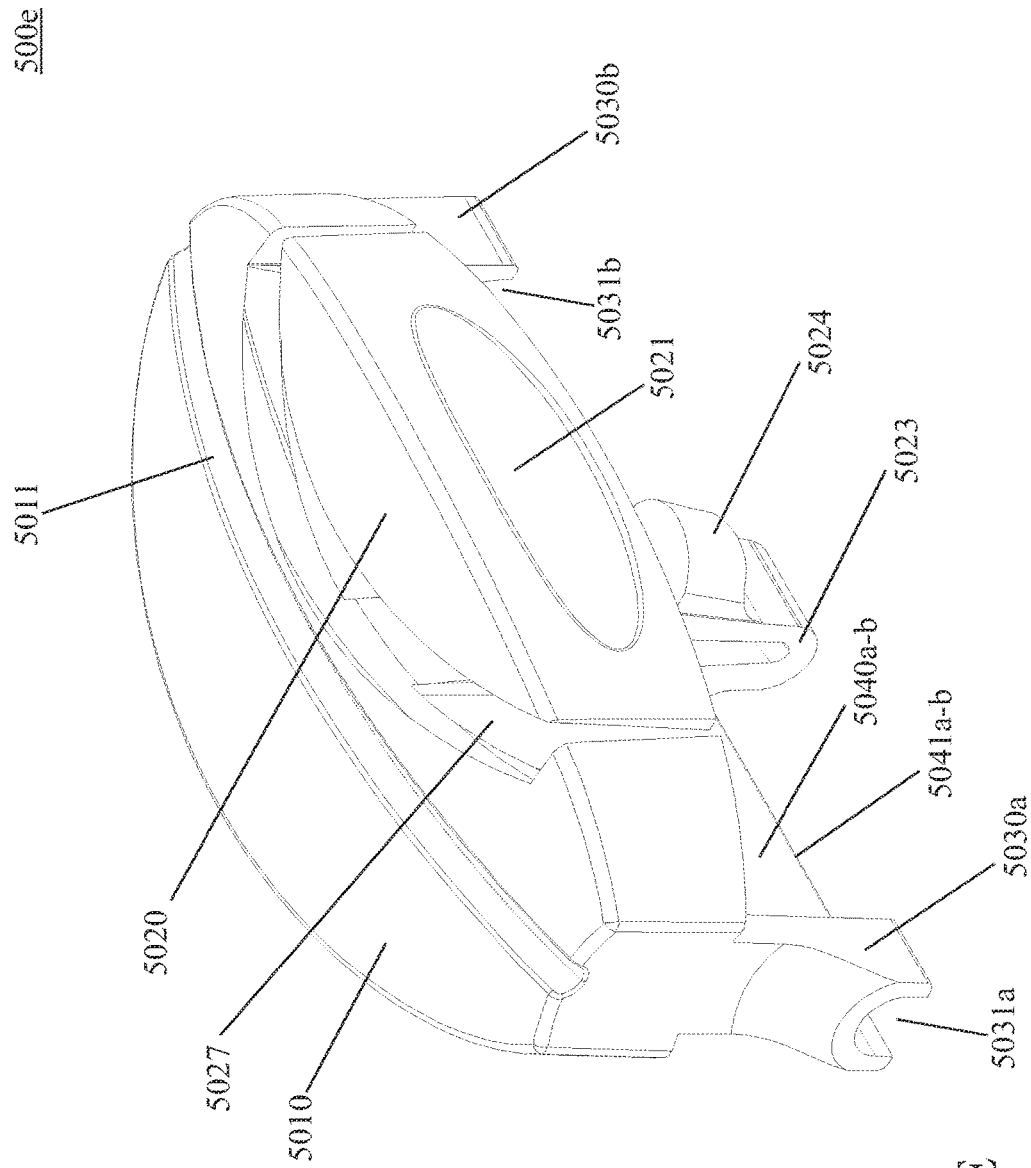
FIG. 5E shows an alternative embodiment of the first connector that may be used in the pump system of FIG. 3A.
Figure 5F:
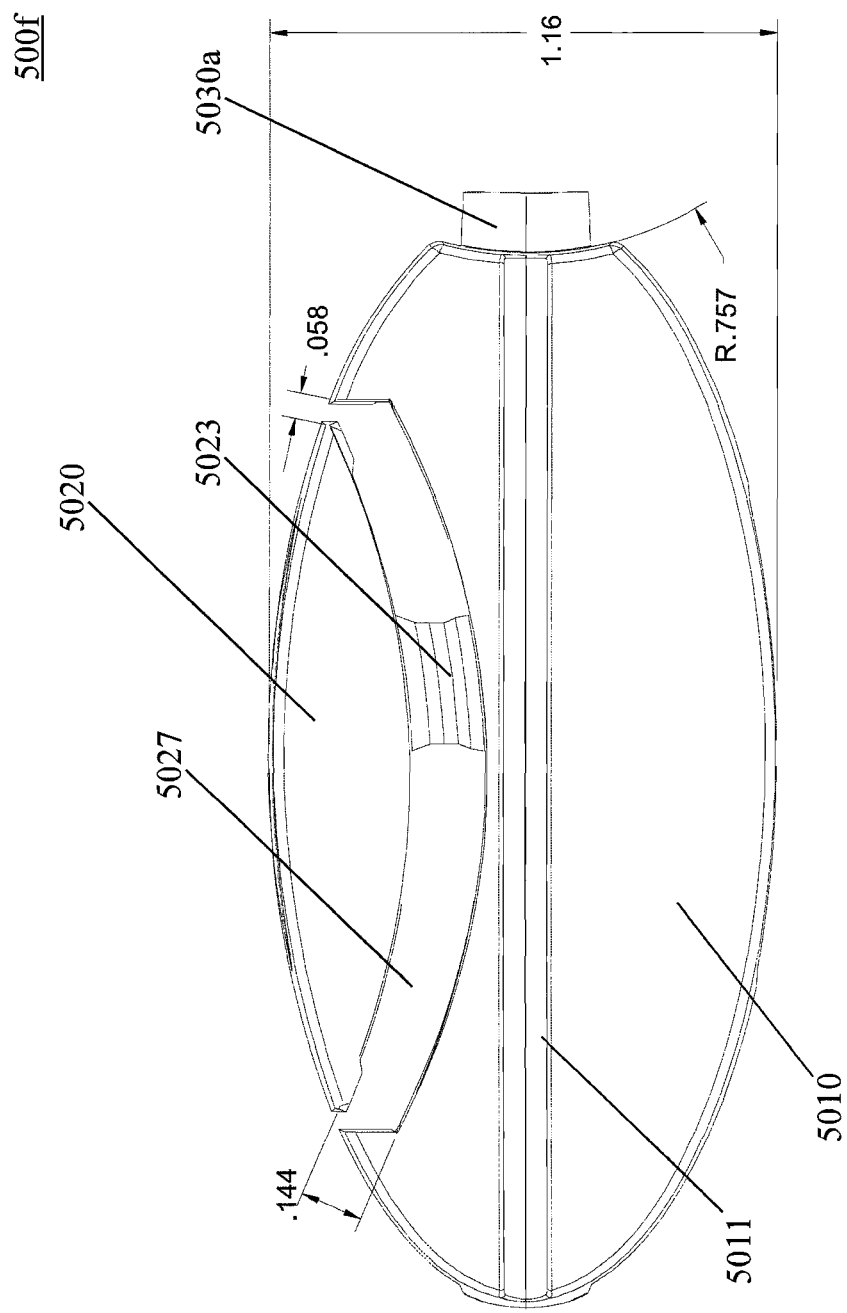
FIGS. 5F-L show dimensions of an embodiment of the first connector of FIG. 5E.

FIG. 5E shows an alternative embodiment of first connector that may be used in the pump system 300*a* of FIG. 3A. In at least one embodiment, first connector 500*e* includes at least a body 5010, a groove 5011, a tab 5020, a tab base 5021, a tab member 5023, a tab 5024, a space 5027, side members 5030*a* and 5030*b*, grooves 5031*a* and 5031*b*, a panel 5040, and a panel edge 5041. In other embodiments, first connector 500*e* may not have all of the elements or features listed and/or may have other elements or features instead of or in addition to those listed.

FIG. 5E shows an alternative embodiment of first connector 340 of FIG. 3A or 500*a* of FIG. 5A. Instead of having holes in the ends of the middle member 526 and side members 530*a* and 530*b* (FIG. 5A), the first connector 500*e* in FIG. 5E includes grooves (e.g., semicircular grooves) in the ends of two side members for guiding the tubing 360 to be inserted into the sensor slot(s) in the first receptacle 320.

In at least one embodiment, body 5010 is similar to the body 510 except that the base of body 5010 has a different shape with two side members protruding from either ends of the base. Groove 5011 is a groove across the base of the body 5010 for molding purposes. Tab 5020 is similar to the tab 520 except that tab 5020 has a different shape and is connected to a panel that connects the two side members of body 5010. Tab base 5021 is similar to the tab base 521 except that tab base 5021 includes a different shape with an oval shaped concave on the side facing away from the body 5010. Tab member 5023 is similar to tab member 523. Tab member 523 connects to the panel between the two side members. Tab 5024 is similar to the protrusion 524. Tab 5024 meets with a flat surface on the side of the tab member 5023 opposite the tab base 5021. Space 5027 is similar to the space 527. Space 5027 is in-between body 5010 and tab 5020. Side members 5030*a* and 5030*b* are similar to side members 530*a* and 530*b*. Side members 5030*a* and 5030*b* include grooves (rather than holes) on the end facing away from the base. Grooves 5031*a* and 5031*b* are grooves with a cross section of a part (e.g., a half) of a circular shape, located on the ends of side member 5030*a* and 5030*b* facing away from the base for guiding and supporting the tubing 360 to be inserted into the first receptacle 320. Panel 5040 is similar to either one of panels 540*a* and 540*b*. Panel 5040 protrudes from the base of body 5010 and connects side members 5030*a* and 5030*b*. Panel edge 5041 is similar to either one of panel edge 541*a* and 541*b*. Panel edge 5041 connects the bottom surfaces of grooves 5031*a* and 5031*b*.

Figure 5G:
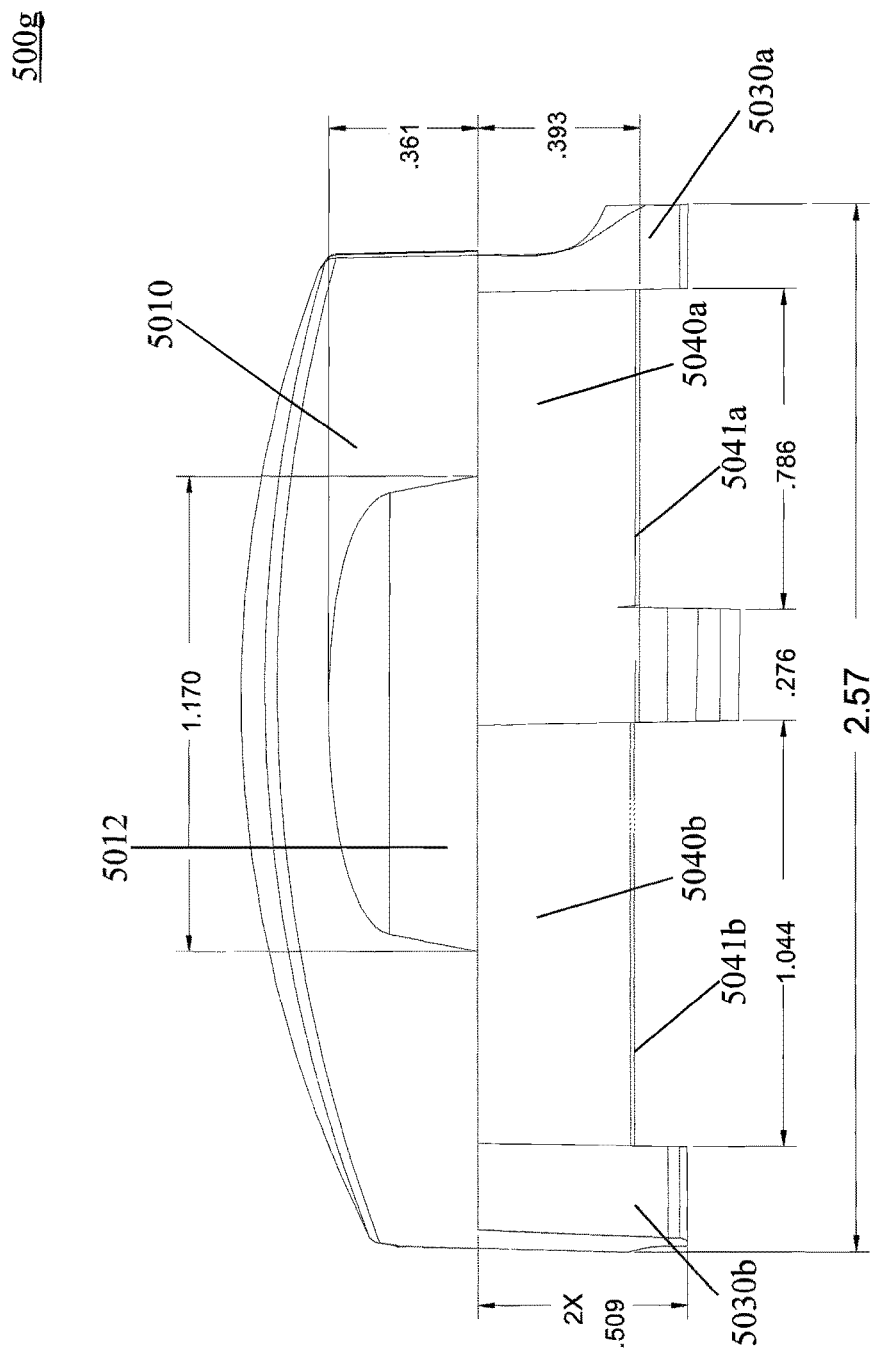
Figure 5H:
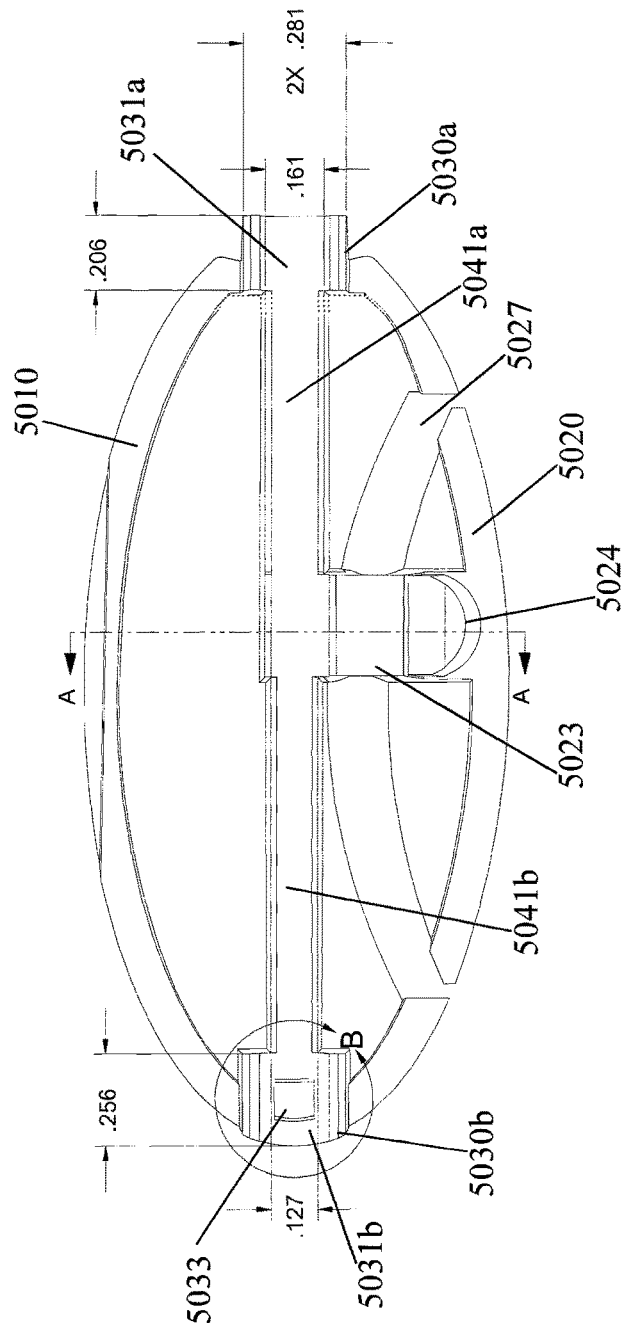
Figure 5I:
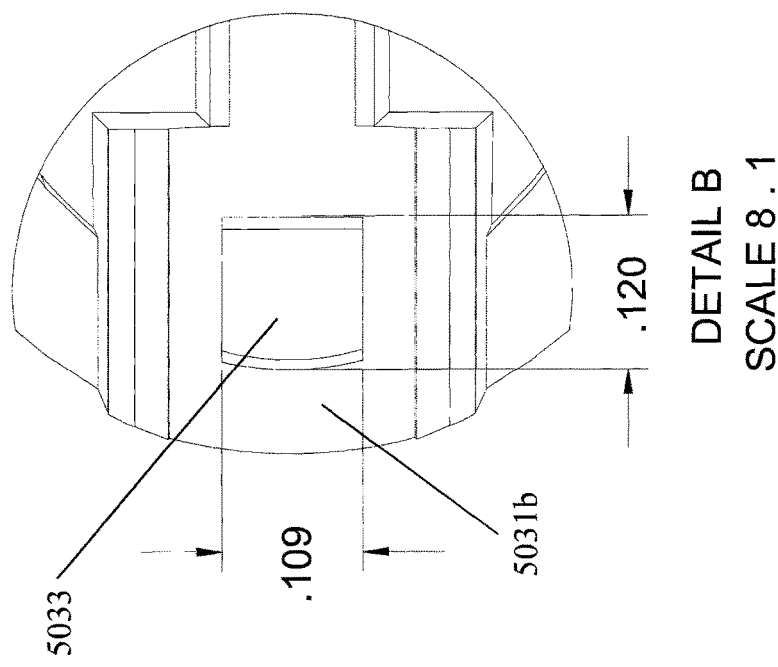
Figure 5J:
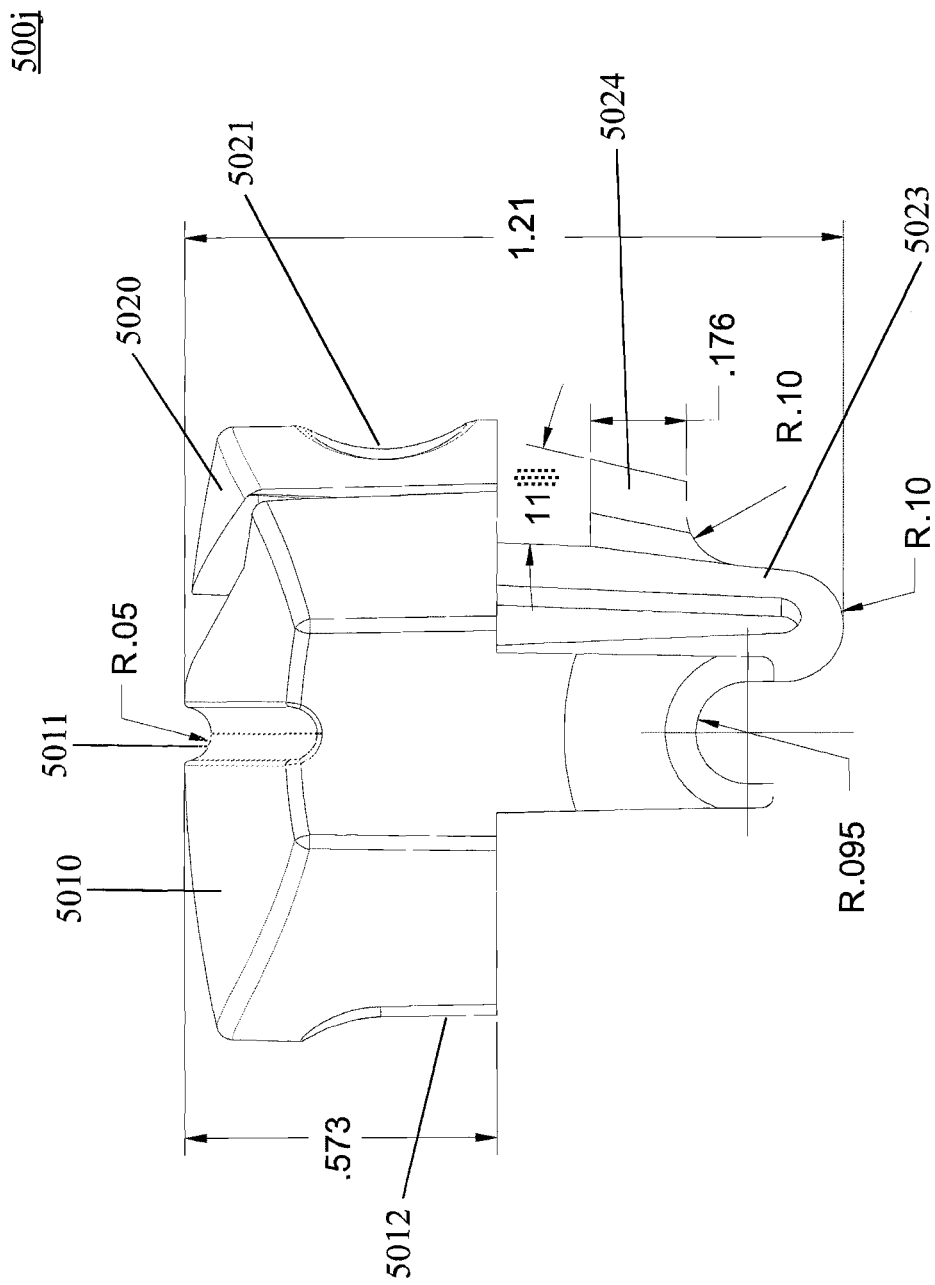
Figure 5K:
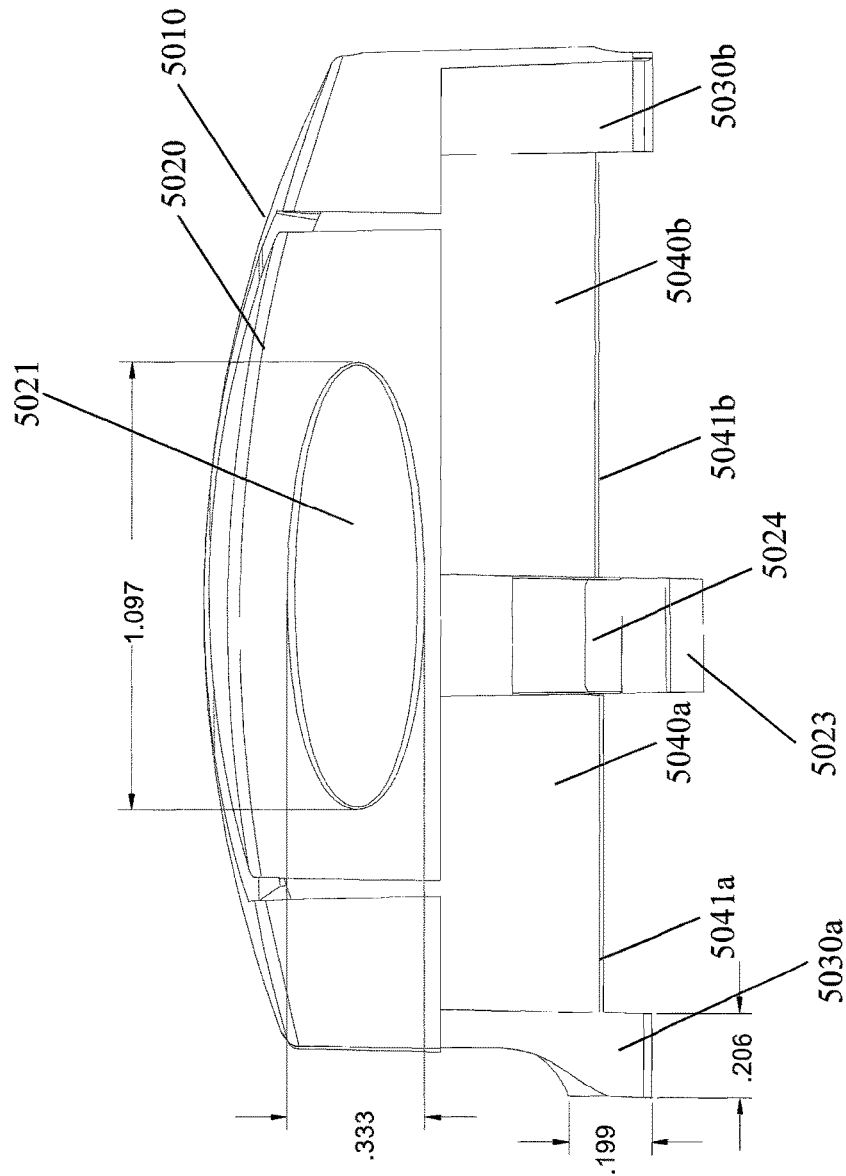
Figure 5L:
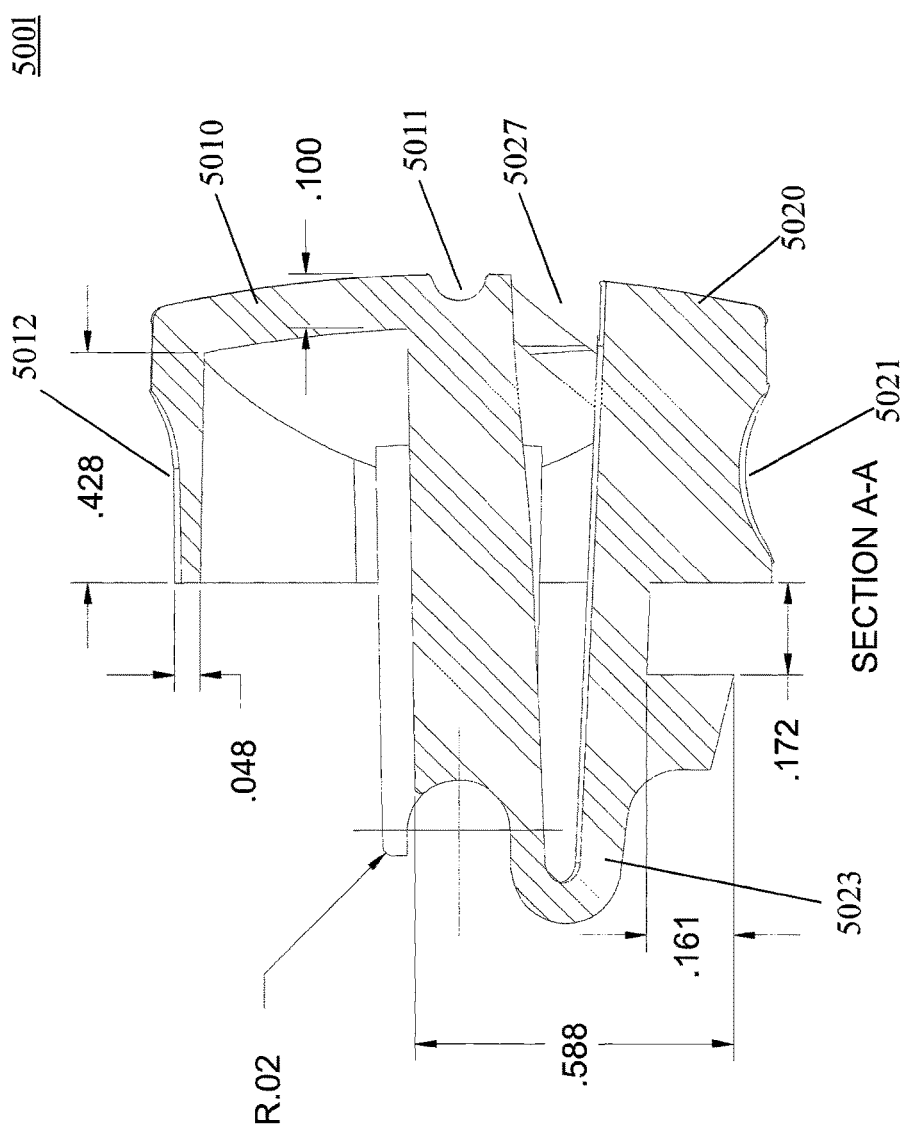

FIGS. 5F-L show dimensions of the first connector 500*e* of FIG. 5E. FIG. 5G also includes a concave 5012 on the side of the body 5010 opposite to the tab 5020 for a better grip of the first connector 500*e*. FIG. 5H further shows a hole 5033 with a square cross section in the groove 5031*b* of the side member 5030*b* for molding purposes (section B of FIG. 5H and FIG. 5I). In other embodiments, first connector 500*e* includes other dimensions, shapes, and/or structures.

Figure 5M:
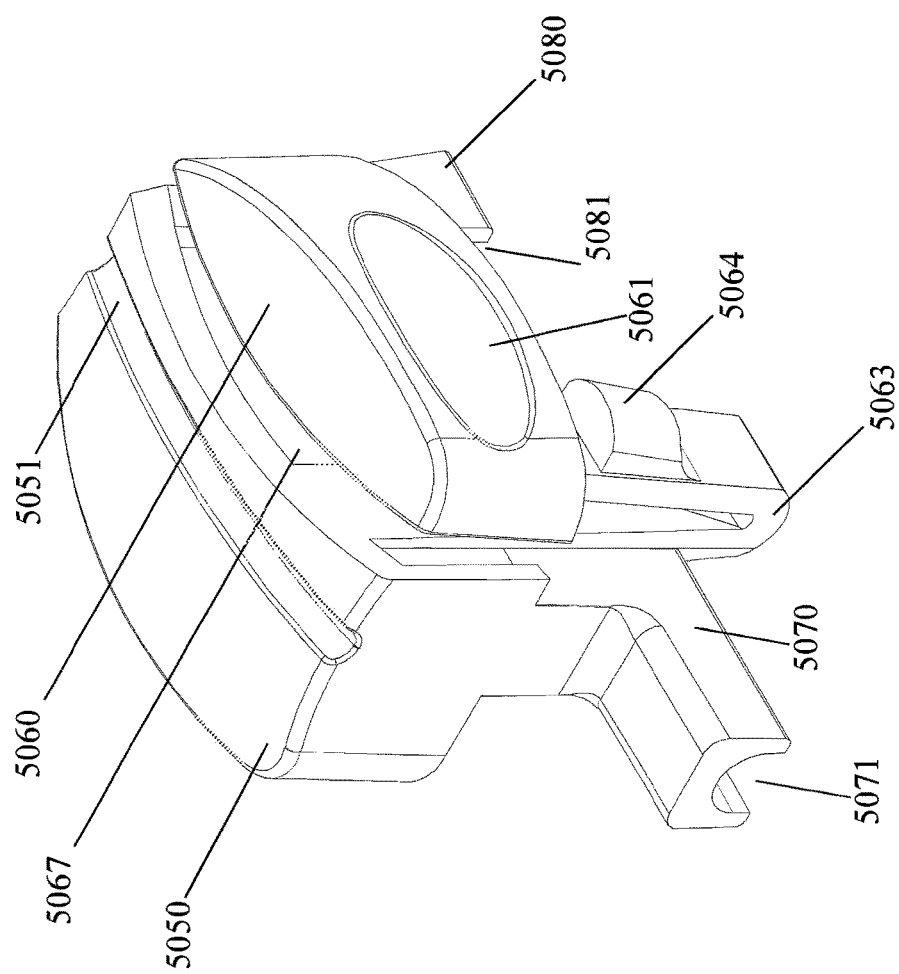
FIG. 5M shows an alternative embodiment of the second connector that may be used in the pump system of FIG. 3A.
Figure 5N:
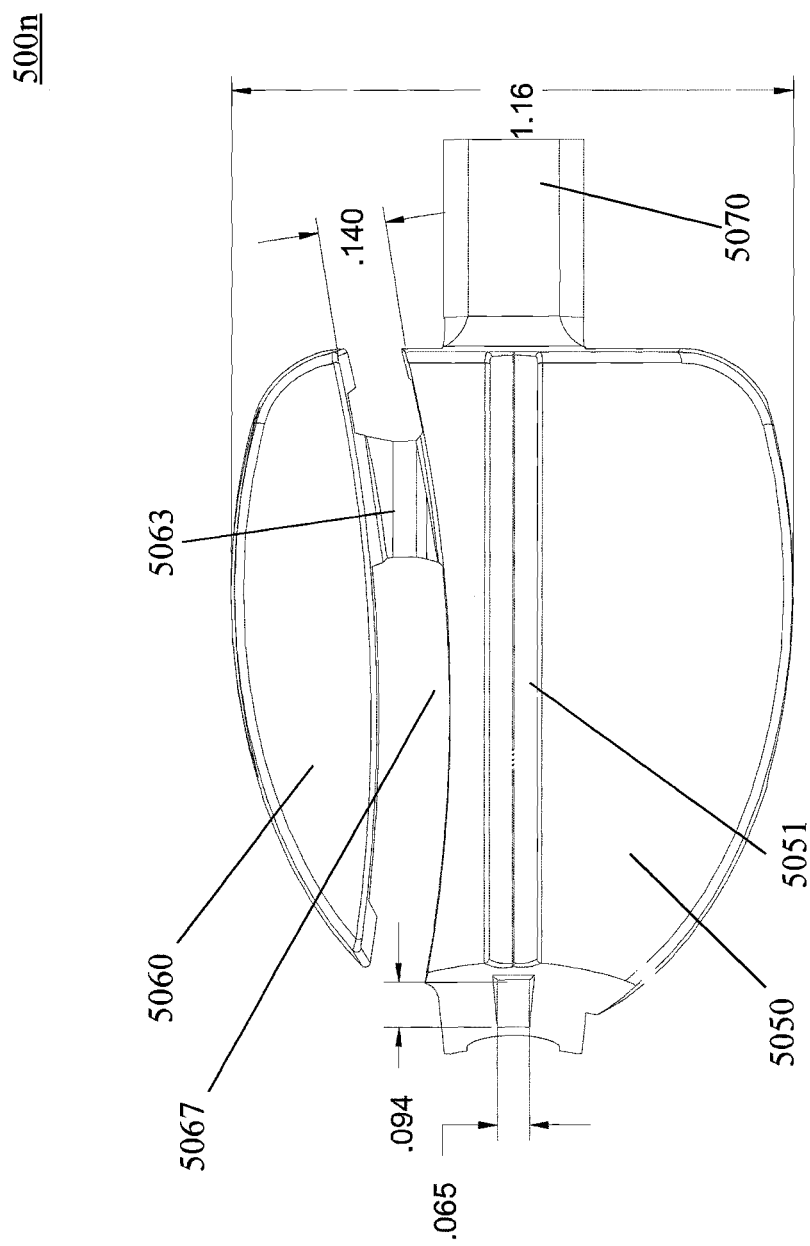
FIGS. 5N-S show dimensions of an embodiment of the second connector of FIG. 5M.

FIG. 5M shows an alternative embodiment of second connector that may be used in the pump system 300*a* of FIG. 3A. In at least one embodiment, second connector 500*m* includes at least a body 5050, a groove 5051, a latch 5060, a tab base 5061, a tab member 5063, a tab 5064, a space 5067, side members 5070 and 5080, and grooves 5071 and 5081. In other embodiments, second connector 500*m* may not have all of the elements or features listed and/or may have other elements or features instead of or in addition to those listed.

FIG. 5M shows an alternative embodiment of second connector 350 of FIG. 3A or 500*c* of FIG. 5A, having grooves (e.g., semicircular grooves) in the ends of two side members for guiding the tubing 360 to be inserted into the sensor slot(s) in the second receptacle 330.

Body 5050 may be similar to body 550. Body 5050 includes approximately one fourth of an oval shaped base with two side members protruding from either end of the body 5050. Groove 5051 is similar to groove 5011. Groove 5051 runs across the base of the body 5050. Latch 5060 is similar to tab 560. Latch 5060 is connected to a panel that connects the two side members. Tab base 5061 is similar to the tab base 561 except that tab base 5061 is in a different shape and/or size than tab base 561. Tab member 5063 is similar to tab member 563. Tab member 5063 is connected to the panel linking the two side members. Tab 5064 is similar to protrusion 564. Tab 5064 is not connected to an extended portion similar to extended portion 565. Space 5067 is similar to space 567. Space 5067 is in-between body 5010 and tab 5020. Side members 5070 and 5080 are similar to side members 570 and 580, respectively. Side members 5070 and 5080 include grooves on the ends facing away from the base. Grooves 5071 and 5081 are grooves with a cross section of a part (e.g., a half) of a circular shape, located on the ends of side member 5070 and 5080 facing away from the base for guiding and supporting the tubing 360 to be inserted into the second receptacle 330.

Figure 5O:
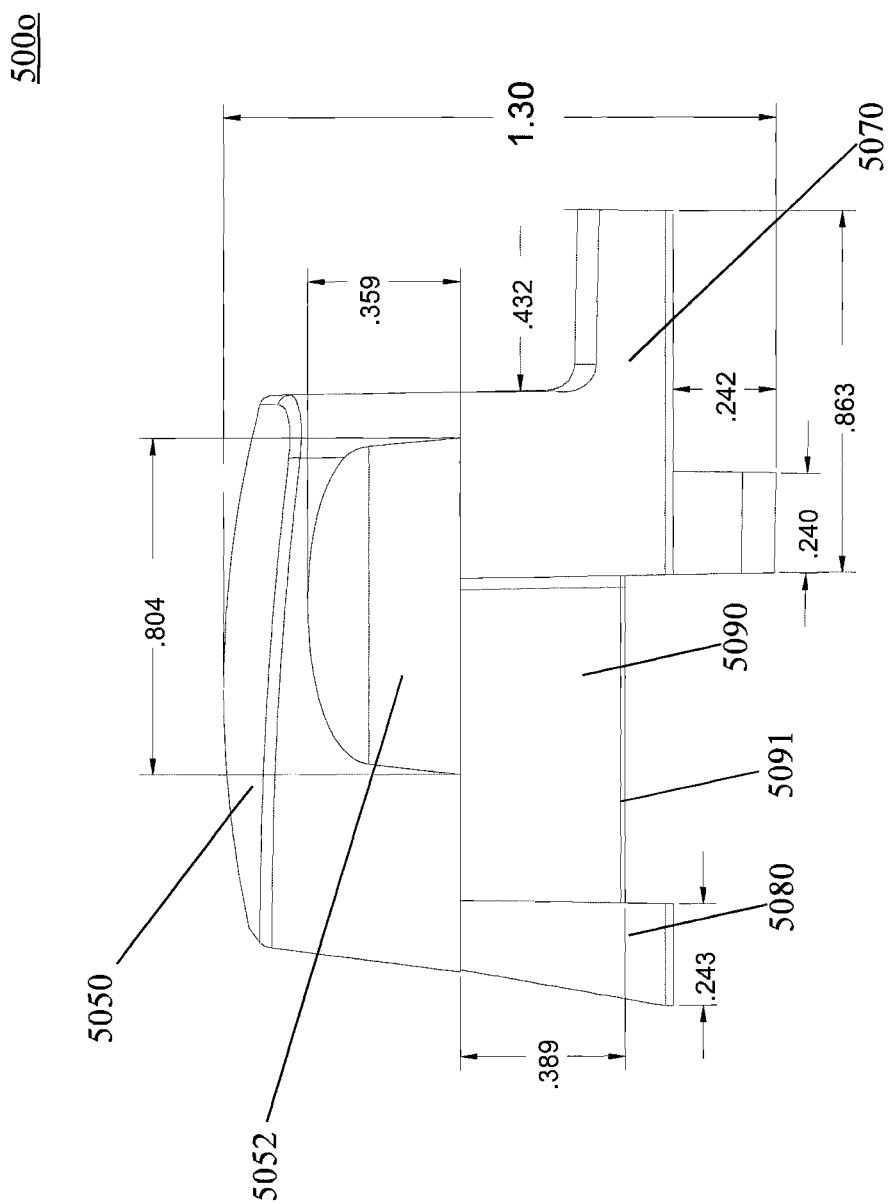
Figure 5P:
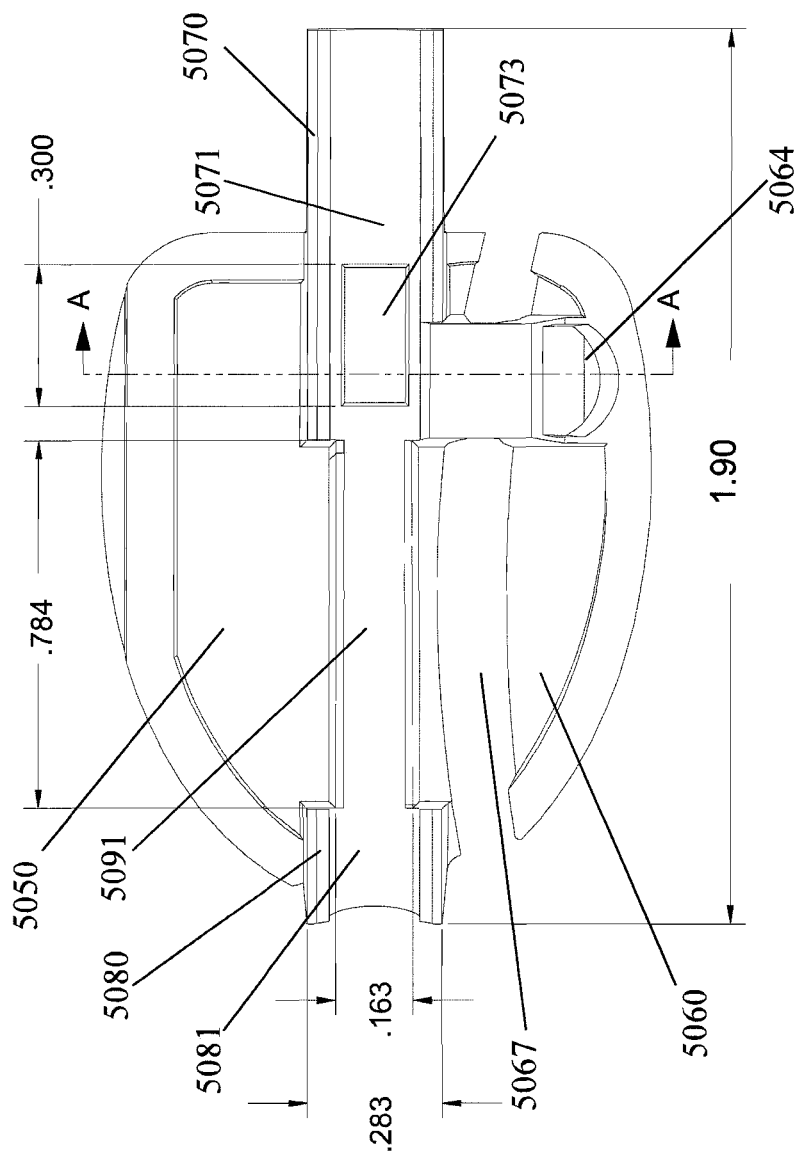
Figure 5Q:
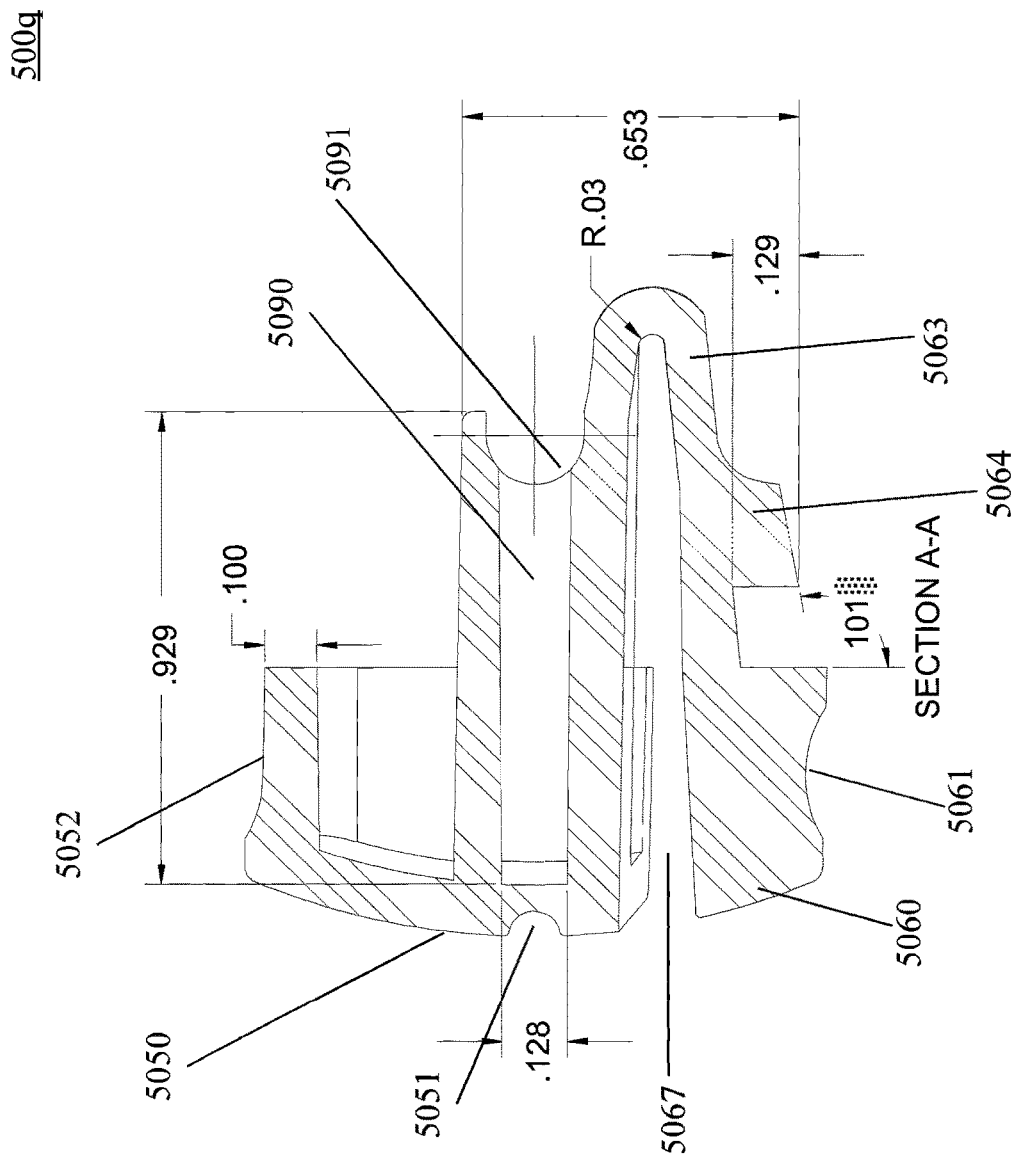
Figure 5R:
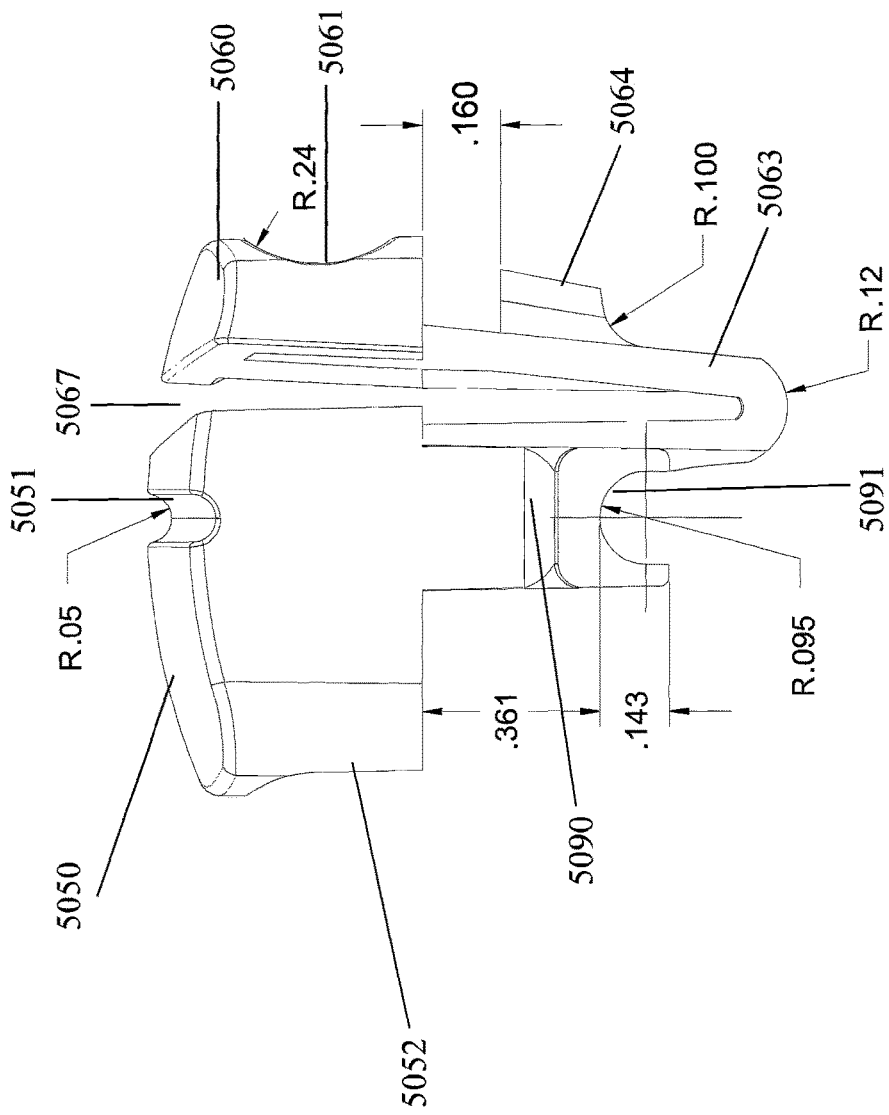
Figure 5S:
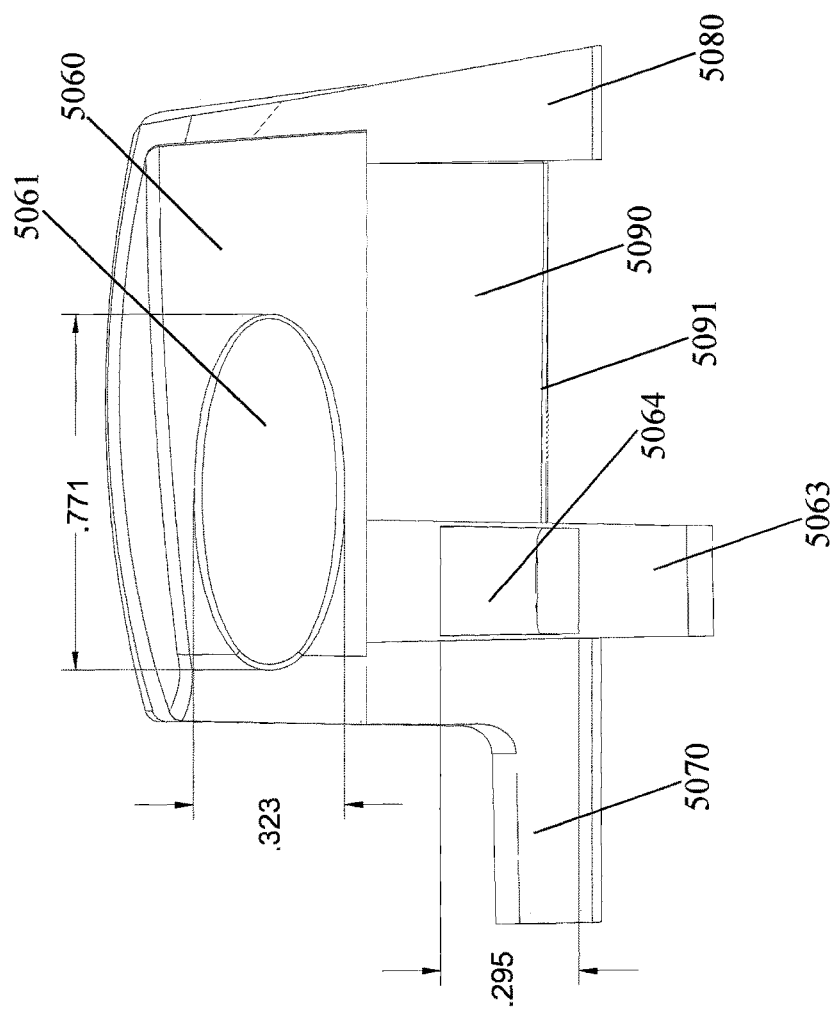

FIGS. 5N-S show dimensions of the second connector 500m of FIG. 5M. FIG. 5O further includes at least a concave 5052, a panel 5090, and a panel edge 5091. In at least one embodiment, concave 5052 is a concave on the side of the body 5050 opposite to the latch 5060 for a better grip of the second connector 500m. Panel 5090 may be similar to the panel 590. Panel 5090 connects the bottom surfaces of grooves 5071 and 5081 for supporting the tubing 360. Panel edge 5091 may be similar to the panel edge 591. Top surface 5091 is on the end of panel 5090 of the second connector 500m. FIG. 5P further includes at least a hole 5073 with a rectangular cross section located in the side member 5070. In FIG. 5Q, the number 101 indicates an angle with 101 degrees. In other embodiments, second connector 500m includes other dimensions, shapes, and/or structures.

Figure 6A:
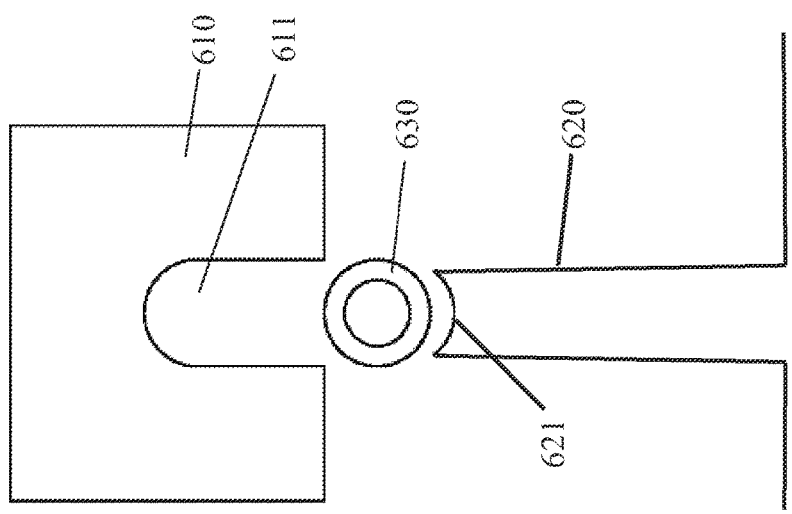
FIGS. 6A-C show embodiments of the manner in which the connectors provide support for the tubing.
Figure 6B:
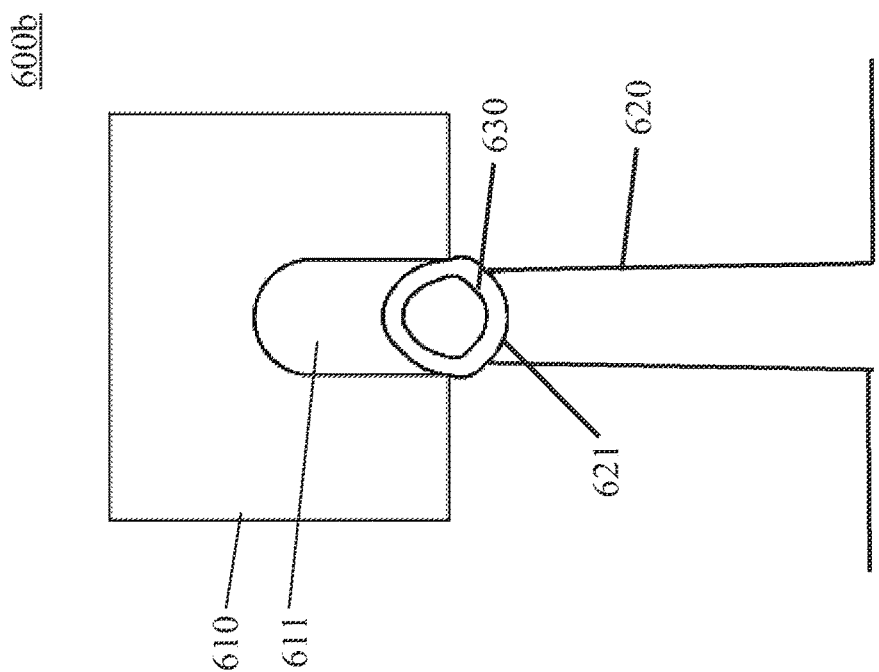
Figure 6C:
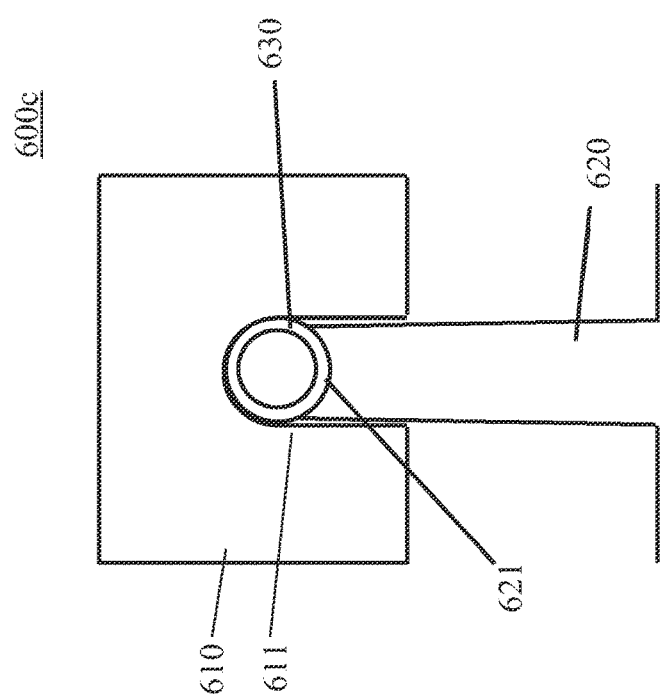

FIGS. 6A-C show embodiments of the manners in which the connectors provide support for the tubing. FIGS. 6A-C include at least a sensor 610, a sensor slot 611, a panel 620, a panel edge 621, and tubing 630. In other embodiments, FIGS. 6A-C may not have all of the elements or features listed and/or may have other elements or features instead of or in addition to those listed.

FIGS. 6A-C show that the panel edges (e.g., panel edge 541a, 541b, 591, 5041, or 5091) of connectors contact an arc of the tubing's outside diameter preferably, but not limited to between 120 degrees and 180 degrees to provide maximum support for the tubing without interfering with the sensor slots during insertion. In at least one embodiment, the panel edges provide a mechanical advantage allowing the user to overcome the resistance of the tight fit of the tubing into the sensor slots and to fully and uniformly insert the tubing into the sensors slots.

FIG. 6A shows a cross sectional view of each element before tubing insertion. In FIG. 6A, the panel edge 621 includes a portion of a surface that has a circular cross section that has a radius that is the same or similar to the outside radius of the tubing 630. FIG. 6B shows that the panel edge 621 contacts an arc of the tubing's outside diameter for providing support around an arc of tubing 630 to prevent deformation of tubing 630 that would prevent the tubing 630 from being inserted into the sensor slot 611. In at least one embodiment, when the outside diameter of tubing 630 is slightly larger than the sensor slot 611, the panel edge 621 provides a uniform pressure to insert the tubing 630, even if slightly deformed when entering the sensor slot 611 (as shown in FIG. 6B), so that tubing 630 would not slip off the panel edge 621 or away from the sensor slot 611. In at least one embodiment, the tubing 630 needs to be inserted and pushed deep into the sensor slot 611 (e.g., close to the bottom of the sensor slot 611) so that the sensing elements of the sensor 610 may obtain an accurate reading (as shown in FIG. 6C). In this embodiment, the panel 620 has a thickness at the top that is narrower than the sensor slot 611 for partially inserting into the sensor slot 611 without interfering with the sensor 610, so that the panel edge 621 may push the tubing 630 further into the sensor slot 611. In at least one embodiment, FIGS. 6A-C show the manners of tubing insertion into the sensor slot(s) of sensor(s) installed in the first receptacle 320 and/or the second receptacle 330.

Sensor 610 and sensor slot 611 may be embodiments of sensors 120a, 120b, or 120c, and sensor slots 121a, 121b, or 121c, respectively, which were discussed in conjunction with FIG. 1. In one embodiment, sensors 610 may be installed in the first receptacle 320 or the second receptacle 330. In another embodiment, at least one sensor 610 is installed in each of the first receptacle 320 and the second receptacle 330. Panel 620 may be an embodiment of the panels 540a, 540b, 590, 5040, or 5090, which were discussed in conjunction with FIGS. 5A-S. Panel edge 621 may be an embodiment of the panel edge 541a, 541b, 591, 5041, or 5091, which were discussed in conjunction with FIGS. 5A-S. Tubing 630 may be the same as tubing 130 or 360, which were discussed in conjunction with FIG. 1 and FIG. 3A.

Figure 7A:
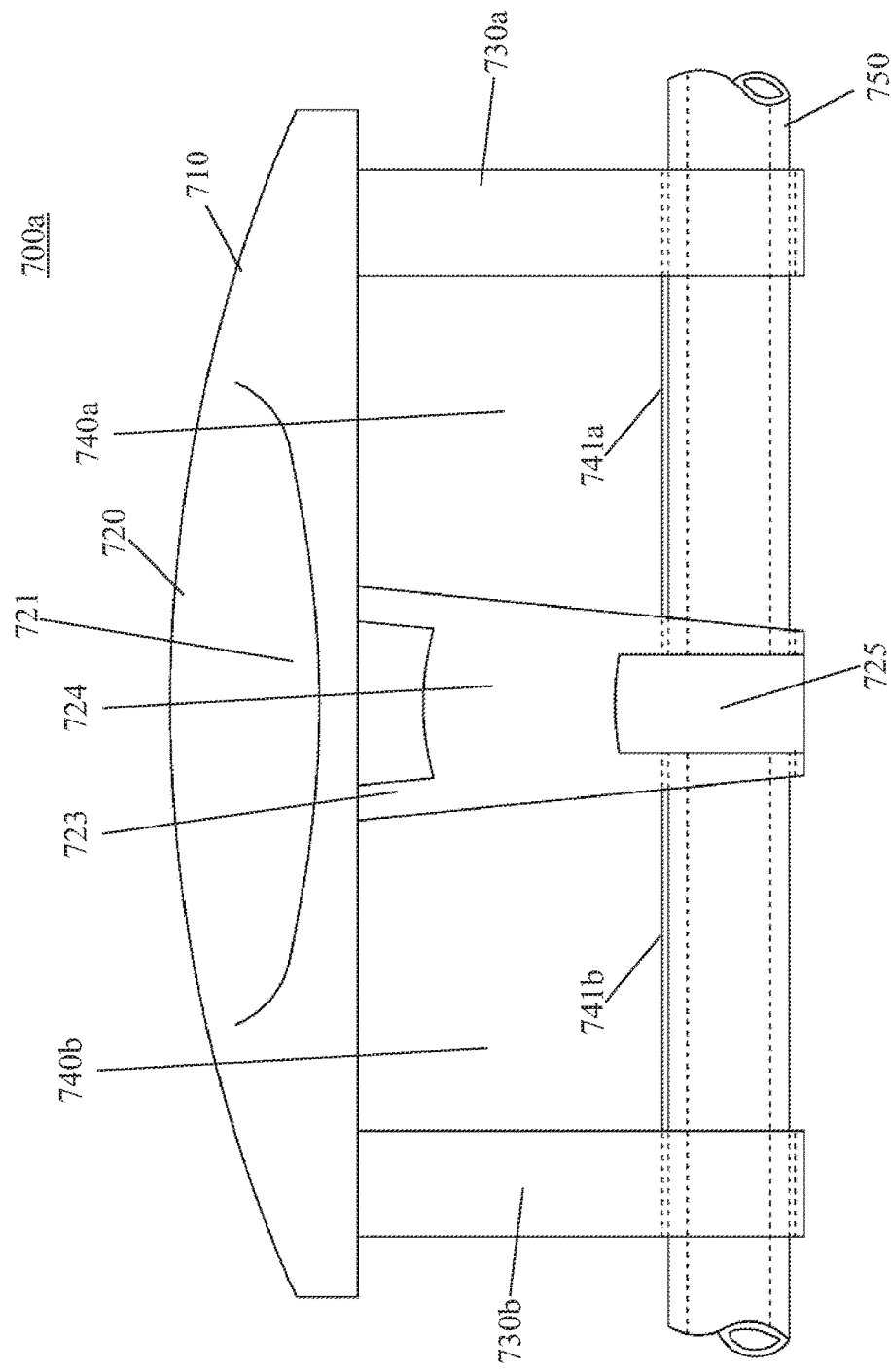
FIG. 7A shows a side view of an embodiment in which the tubing is placed in the first connector of FIG. 5A.

FIG. 7A shows a side view of an embodiment when tubing is placed in the first connector 500a of FIG. 5A. FIG. 7A includes at least a body 710, a protrusion 720, a tab base 721, a tab member 723, a protrusion 724, an indent 725, side members 730a and 730b, panels 740a and 740b, panel edges 741a and 741b, and tubing 750. In other embodiments, FIG. 7A may not have all of the elements or features listed and/or may have other elements or features instead of or in addition to those listed.

FIG. 7A shows a side view 700a of an embodiment of the first connector 500a of FIG. 5, with the base of first connector 500a at the top of FIG. 7A and with the structures for supporting the tubing facing downward, for inserting into sensor slot(s) within the first receptacle 320. In at least one embodiment, the tubing is held and/or retained in holes in the middle member and two side members, thus aligning with panel edges across the length of the tubing to apply uniform pressure for inserting the portions of tubing in-between the middle member and two side members into two sensor slots in the first receptacle 320, respectively. In at least one embodiment, tubing may be guided by grooves 5031a and 5031b and supported by panel edge 5041 of first connector 500e during insertion. In at least one embodiment, the tubing may be guided and/or supported in holes 511 and 581 and by panel edge 591 of second connector 500c of FIG. 5C, or by grooves 5071 and 5081, and panel edge 5091 of second connector 500m of FIG. 5M, for inserting into sensor slot(s) within the second receptacle 330.

In at least one embodiment, body 710, protrusion 720, tab base 721, tab member 723, protrusion 724, indent 725, side members 730a and 730b, panels 740a and 740b, and panel edges 741a and 741b are the same as body 510, tab 520, tab base 521, tab member 523, protrusion 524, indent 525, side members 530a and 530b, panels 540a and 540b, and panel edge 541a and 541b, which were discussed in conjunction with FIG. 5A. In at least one embodiment, tubing 750 is the same as tubing 130, which was discussed in conjunction with FIG. 1.

Figure 7B:
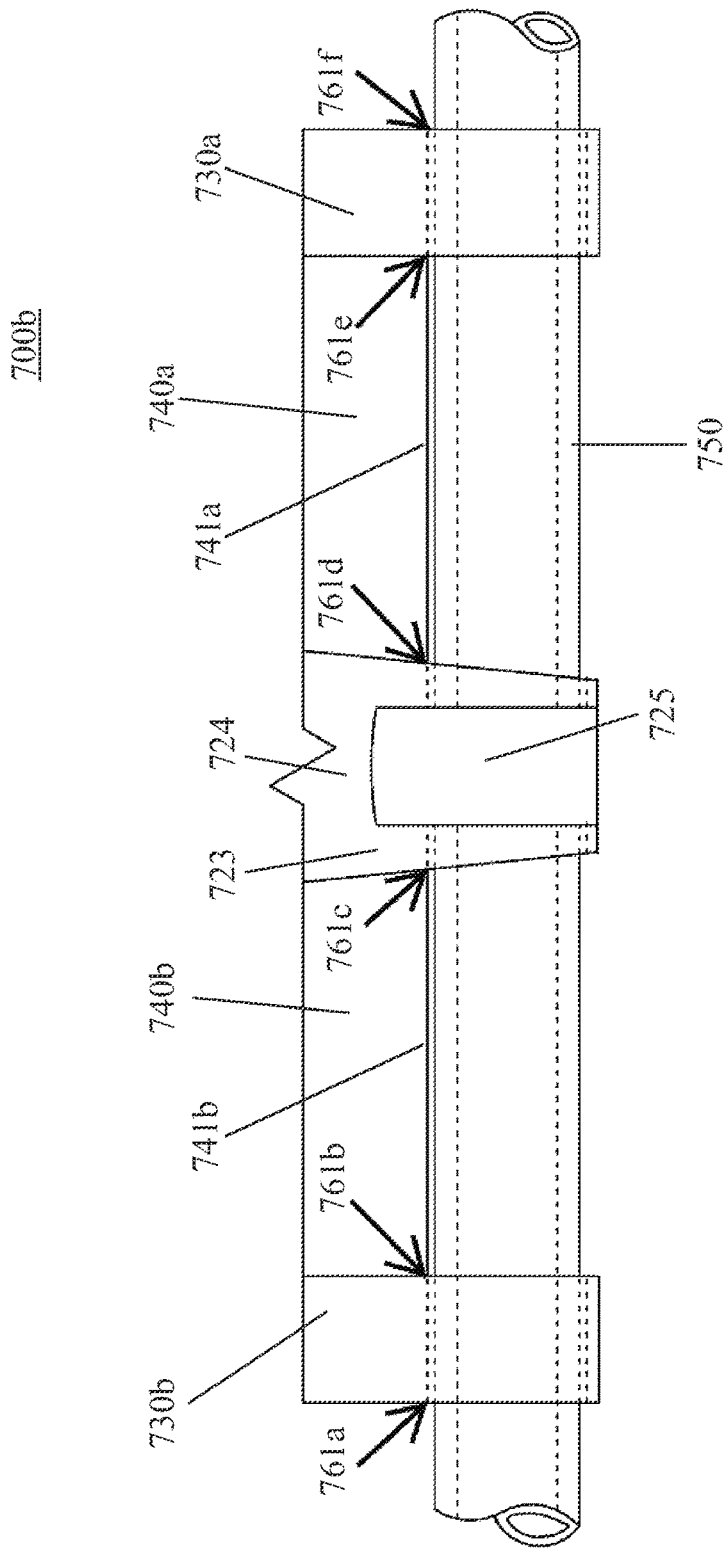
FIG. 7B shows a partial view of an embodiment in which the tubing is partially attached to the first connector of FIG. 7A.

FIG. 7B shows a partial view of an embodiment when the tubing is partially attached to the first connector in FIG. 7A. FIG. 7B includes at least tab member 723, protrusion 724, indent 725, side members 730a and 730b, panels 740a and 740b, panel edges 741a and 741b, and tubing 750, which were discussed in conjunction with FIG. 7A. FIG. 7B further includes at least a plurality of arrows 761a-f. In other embodiments, FIG. 7B may not have all of the elements or features listed and/or may have other elements or features instead of or in addition to those listed.

FIG. 7B shows that the tubing 750 may be partially affixed (e.g., glued) to the first connector 500*a* at the areas of the tubing 750 that are in contact with the middle member and side members 730*a* and 730*b*, while the tubing 750 is not affixed to the panel edges 741*a* and 741*b*. In one embodiment, the tubing 750 is glued or affixed via other methods only at the end points of the panel edges 741*a* and 741*b* (e.g., at the points indicated by the arrows 761*a*-*f* of FIG. 7B). In another embodiment, the tubing 750 is glued or affixed at the areas that are in-between arrows 761*a* and 761*b*, arrows 761*c* and 761*d*, and arrows 761*e* and 761*f*, respectively, for securely affixing the tubing 750 to the middle member and side members 730*a* and 730*b*. In at least one embodiment, the tubing is partially affixed to both the first and second connectors, at the end points of supporting webs, or to the middle member and/or side members (e.g., middle member 526 and side members 530*a* and 530*b* of the first connector 500*a*, side members 570 and 580 of the second connector 500*c*, grooves 5031*a* and 5031*b* of the first connector 500*e*, grooves 5071 and 5081 of the second connector 500*m*). In one embodiment, the tubing may be affixed or glued to the area of the panel edge 5041 close to the tab member 5023 of the first connector 500*e* (FIG. 5E). As a result of the embodiments mentioned above, once the connectors are inserted into the mating receptacles, pulling on the tubing 750 will not cause a stress on or subsequent movement of the tubing 750 in the sensor slots within the receptacles, which could adversely affect the measurement of the fluid properties by the sensors installed in the receptacles.

In at least one embodiment, the tubing 750 is not glued or otherwise affixed onto or along the panel edges 741*a* and 741*b* (or panel edge 591 of the second connector 500*c* in FIG. 5C, panel edge 5041 except the area close to the tab member 5023 of the first connector 500*e* in FIG. 5E, panel edge 5091 of the second connector 500*m* in FIG. 5M). In at least one embodiment, the advantages of not affixing the tubing 750 to the panel edges may include that small motions of the connectors along the insertion/retraction axis do not disturb the tubing's position in the sensor slots which could adversely affect the measurement of the fluid properties by the sensors. In an alternative embodiment, the connectors may be affixed or loosened from the tubing 750 in a non-permanent manner, allowing the user to reposition the connectors along the length of the tubing 750. This embodiment allows the user to provide the optimum length of tubing 750 for the inlet and outlet portions of the tubing set. In at least one embodiment, the partially affixing the tubing 750 to the connectors may provide mechanical retention force of the tubing 750 in the sensors when the connectors mate with the receptacles, while the tubing 750 may not necessarily be retained by the mechanical resistance of the sensor slots against the tubing walls. In this embodiment, the sensor slots may be enlarged so that the mechanical interference between the walls of the sensor slots and the tubing wall is minimized while still meeting the measurement requirement of an air tight fit between the sensor slots and the tubing wall. In at least one embodiment, the portions of the sensor slots that are not in direct contact with sensing elements may be enlarged for a easier insertion of the tubing 750, which will be discussed further in FIGS. 8A-D.

Figure 8A:
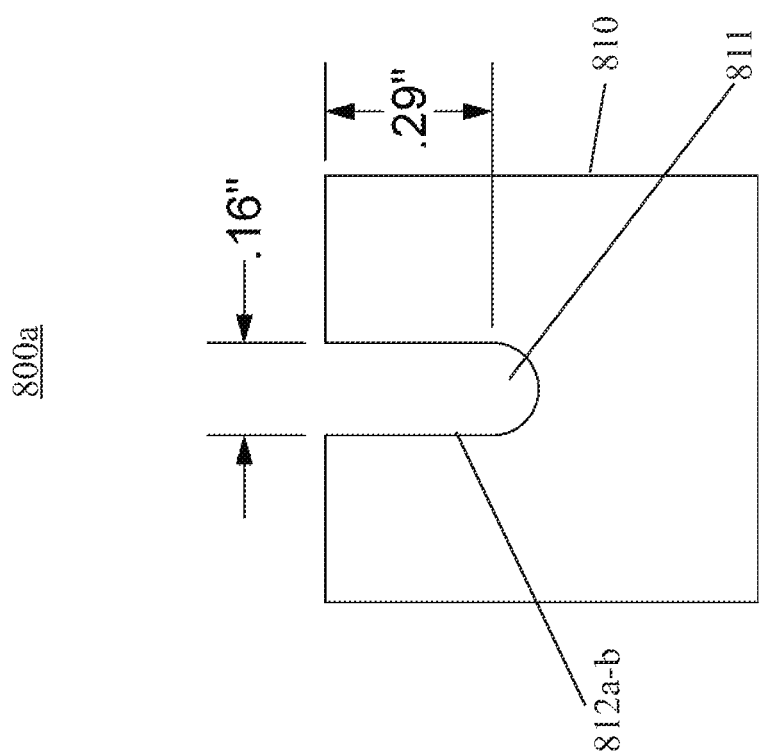
FIG. 8A shows a cross sectional side view of an embodiment of a sensor having a sensor slot.

FIG. 8A shows a cross sectional view 800*a* of an embodiment of a sensor having a sensor slot. FIG. 8A includes at least a sensor 810, a sensor slot 811, and a pair of side walls 812*a*-*b*. In other embodiments, FIG. 8A may not have all of the elements or features listed and/or may have other elements or features instead of or in addition to those listed.

FIG. 8A shows a sensor with a sensor slot with two side walls and a bottom being a part of (e.g., a half of) circular surface. Sensor 810 and sensor slot 811 may be embodiments of sensors 120*a*, 120*b*, or 120*c*, and sensor slots 121*a*, 121*b*, or 121*c*, respectively, which were discussed in conjunction with FIG. 1.

Side walls 812*a*-*b* are the walls forming the sensor slot 811 that are in direct contact with sensing elements of the sensor 810 and/or may include a surface of the sensor element. In at least one embodiment, side walls 812*a*-*b* are flat walls perpendicular to the top surface of the sensor 810. In at least one embodiment, side walls 812*a*-*b* include sensing elements of the sensor 810 close to the bottom (and/or at the bottom) of the sensor slot 811. In at least one embodiment, tubing (e.g., tubing 130, 360, 630, and/or 750) is tightly fitted into the sensor slot 811 close to the sensing elements for proper reading of the sensor 810. In one embodiment, the sensor slot 811 serves to retain the tubing with mechanical resistance of the sensor slot 811 against the tubing wall. In another embodiment, when the tubing is partially affixed to the connectors that retain the tubing when mating with pump receptacles, the sensor slot 811 may not need to provide the mechanical resistance to retain the tubing. In an embodiment, sensor slot 811 is 0.16 inches wide. The flat part of the sensor walls is 0.29 inches long. The end of the sensor slot has a radius of curvature of half the width of the sensor slot, which is 0.16/2=0.08 inches. The entire depth of the sensor slot is the same as the length of the sensor walls (0.29 inches) plus the radius of curvature of the end of the sensor slot (0.08 inches), which is the same as 0.29+0.08=0.37 inches.

FIG. 8B shows a view 800*b* of an embodiment of the sensor 810 and sensor slot 811 of FIG. 8A. FIG. 8B includes at least sensor 810, sensor slot 811, and side walls 812*a*-*b*, which were discussed in conjunction with FIG. 8A. FIG. 8B further includes at least a left slot 821, a right slot 822, a pair of walls 823*a*-*b*, and a pair of walls 824*a*-*b*. In at least one embodiment, the dashed lines in FIG. 8B may represent the edges where the walls 823*a*-*b* and 824*a*-*b* meet the rounded bottom. In other embodiments, FIG. 8B may not have all of the elements or features listed and/or may have other elements or features instead of or in addition to those listed.

FIG. 8B shows that the sensor 810 includes a narrower portion, sensor slot 811, which is where the sensing elements are located, and wider slots at both sides of the sensor slot 811 for easier insertion and/or removing of the tubing. The wider slots may not provide resistance to inserting the tubing into the slots. In at least one embodiment, the sensor slot 811 has a length of 0.375±0.038 inches. In other embodiments, sensor slot 811 may have other dimensions.

Left slot 821 is a slot to the left of the sensor slot 811 in the view 800*b*. In at least one embodiment, left slot 821 is in-between two side walls that are not necessarily in direct contact with sensing elements of sensor 810. In one embodiment, left slot 821 may have a uniform width from the top to close to the bottom. In another embodiment, the top of left slot 821 may be wider than the bottom that may have a similar width as the sensor slot 811 (e.g., a wedge shaped slot). In other embodiments, slot 821 may be in other shapes and/or sizes.

Right slot 822 is similar to the left slot 821. The right slot 822 is to the right of the sensor slot 811.

Walls 823*a*-*b* are two walls forming the left slot 821. In one embodiment, walls 823 *a*-*b* may be flat and/or perpendicular to the top surface of sensor 810. In another embodiment, walls 823a-b are tilted to form a wedge shaped slot narrower at the bottom.

Walls 824a-b are similar to walls 823a-b. Walls 824a-b form the right slot 822.

FIG. 8C shows a side view 800c of another embodiment of a sensor having a sensor slot. FIG. 8C includes at least a sensor 830, optional sensing elements 831, an opening 832, a cavity 833, a side wall 834, a neck end 835a, a inner end 835b, a neck wall 836, a tilted wall 837, and a cavity wall 838. In other embodiments, FIG. 8C may not have all of the elements or features listed and/or may have other elements or features instead of or in addition to those listed.

FIG. 8C shows a cross section of an example in which the sensor slot has an entrance opening that is wider and/or tilted to assist insertion of the tubing. Sensor 830 may be an embodiment of sensors 120a, 120b, or 120c, which were discussed in conjunction with FIG. 1.

Optional sensing elements 831 serves to measure fluid properties and/or detect presence of bubbles in the tubing. In at least one embodiment, sensing elements 831 are in direct contact with walls of the sensor slots.

Opening 832 is an entrance opening to a sensor slot. In at least one embodiment, opening 832 is wider at the top close to the surface of a housing of the sensor 830, and narrower at the bottom close to the sensor slot. In at least one embodiment, opening 832 is formed by a wall perpendicular to the top surface of the sensor 830 and a tilted wall.

Cavity 833 is a cavity in the sensor 830 in which the sensing elements 831 are located. The sensor slot is the combination of opening 832 and cavity 833. In at least one embodiment, sensing elements 831 is close to the bottom of the cavity 833.

Side wall 834 is a tilted side wall at one side of the sensor slot. In at least one embodiment, side wall 834 is 8 degrees vertically away from the direction of other side wall at the opening 832. The 8 degree slant of side wall 834 is for creating a wider opening. In at least one embodiment, side wall 834 is flat.

Neck end 835a is the neck edge (which is top edge in FIG. 8C), where side wall 834 meets the top surface of sensor 830.

Inner end 835b is the line inside cavity 833 of the sensor slot, where the side wall 834 meets the rounded end (which is at the bottom end of cavity 833 in FIG. 8C) of the cavity 833. In at least one embodiment, the inner end 835b is smooth from the side wall 834 to the rounded end of cavity 833.

Neck wall 836 is a wall perpendicular to, and in contact, with the outer surface of sensor 830, opposite the wall 834. In at least one embodiment, neck wall 836 and the neck portion of wall 834 form the opening 832.

Tilted wall 837 is a tilted wall for connecting the neck wall 836 and a cavity wall that is a side wall of cavity 833 within the sensor slot. In at least one embodiment, tilted wall 837 in combination with neck wall 836 forms a bottle neck shape, narrower at the opening of the sensor slot (in FIG. 8C above cavity 833).

Cavity wall 838 is a wall that, together with the bottom portion of wall 834, forms cavity 833 where sensing elements 831 may be located within the sensor slot.

Figure 8D:
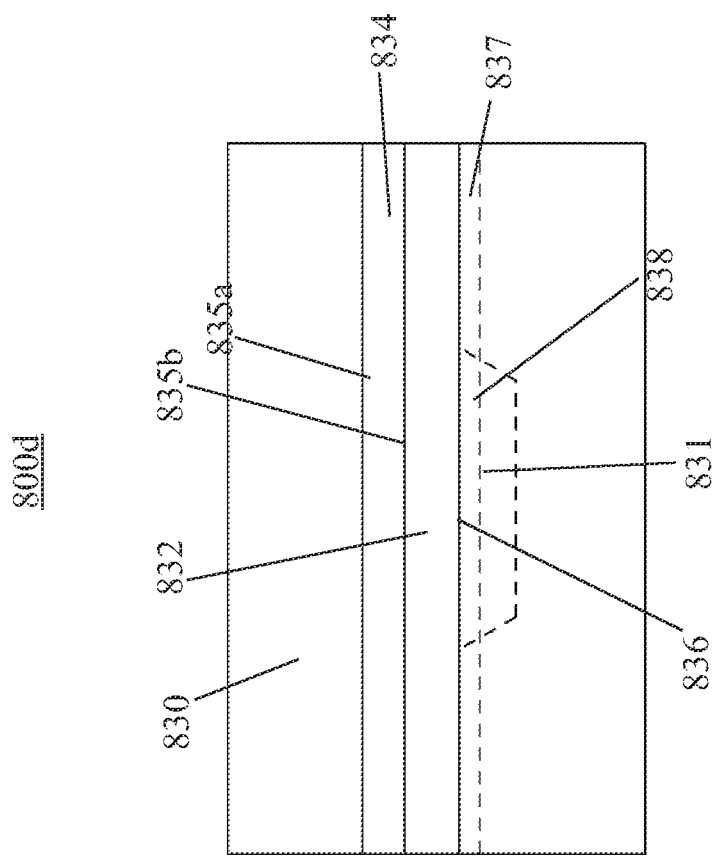
FIG. 8D shows a view of an embodiment of the sensor and sensor slot of FIG. 8C.

FIG. 8D shows a view 800d of an embodiment of the sensor and sensor slot of FIG. 8C. FIG. 8D includes at least sensor 830, sensing elements 831, opening 832, side wall 834, neck end 835a, inner end 835b, neck wall 836, tilted wall 837, and cavity wall 838, which were discussed in conjunction with FIG. 8C. In other embodiments, FIG. 8D may not have all of the elements or features listed and/or may have other elements or features instead of or in addition to those listed.

FIG. 8D shows that a wider entrance opening may be used to guide and position the tubing for insertion into the cavity 833 with a bottle neck portion close to where sensing elements 831 may be located. The wider opening allows a user to easily locate the entrance for the tubing to be inserted into, with less resistance for easier insertion and/or removing of the tubing.

Figure 8E:
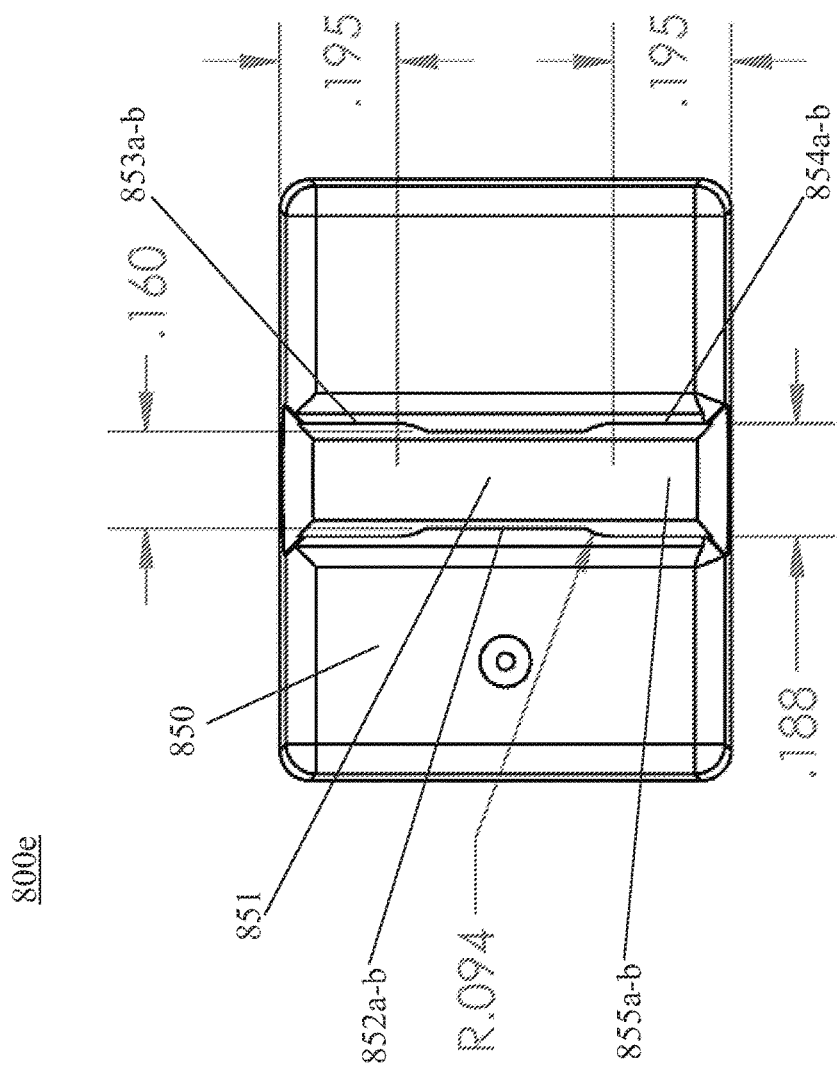
FIG. 8E shows a view of an embodiment of a bubble sensor with sensor slot.

FIG. 8E shows a view 800e of an embodiment of a bubble sensor with sensor slot. FIG. 8E may include a sensor 850, a sensor slot 851, side walls 852a-b, side walls 853a-b and 854a-b, and slots 855a-b. In at least one embodiment, the concentric circles may represent a screw or other fastener for fastening sensing elements inside a housing of the bubble sensor. In other embodiments, FIG. 8E may not have all of the elements or features listed and/or may have other elements or features instead of or in addition to those listed.

FIG. 8E shows an alternative embodiment that may be used as one of sensors 120a-b in device 100 of FIG. 1 or may be installed in the receptacles (e.g., first receptacle 320, second receptacle 330) of the pump system 300a for detecting bubbles in the tubing 130 or 360. In at least one embodiment, sensor 850 may have a narrower slot formed by side walls 852a-b in FIG. 8E where sensing elements are located, and wider slots that are not in direct contact with the sensing elements (e.g., slots formed by side walls 853a-b and 854a-b in FIG. 8E). In at least one embodiment, sensor 850 may be any one of the sensors as described in FIG. 1 with two side walls 852a-b forming a sensor slot 851 into which the tubing is inserted. Slots 855a and 855b are formed by side walls 853a-b and 854a-b, respectively, which are wider than the sensor slot 851. In at least one embodiment, a bottom with a partially circular groove extends along the slots 851, 855a and 855b, which groove has two flat portions on either side of the groove that meet with side walls 852a-b, 853a-b, and 854a-b. FIGS. 8E-H also show the dimensions of the elements of at least one embodiment of the sensors. In other embodiments, sensor 800e may have other structures and/or dimensions.

Figure 8F:
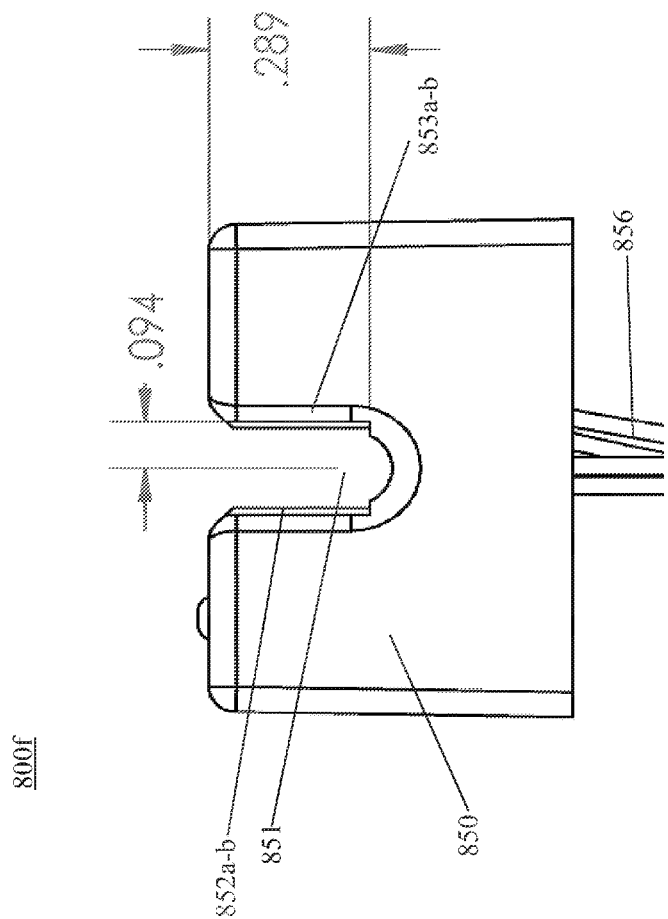
FIG. 8F shows a side view of an embodiment of the bubble sensor of FIG. 8E.

FIG. 8F shows a side view 800f of an embodiment of the bubble sensor 800e of FIG. 8E. In at least one embodiment, FIG. 8F includes at least sensor 850, sensor slot 851, and side walls 852a-b, which were discussed in conjunction with FIG. 8E. FIG. 8F further includes electrical wires 856 for transmitting signals between the sensor 850 and an operating system of the pump 101. In other embodiments, FIG. 8F may not have all of the elements or features listed and/or may have other elements or features instead of or in addition to those listed.

Figure 8G:
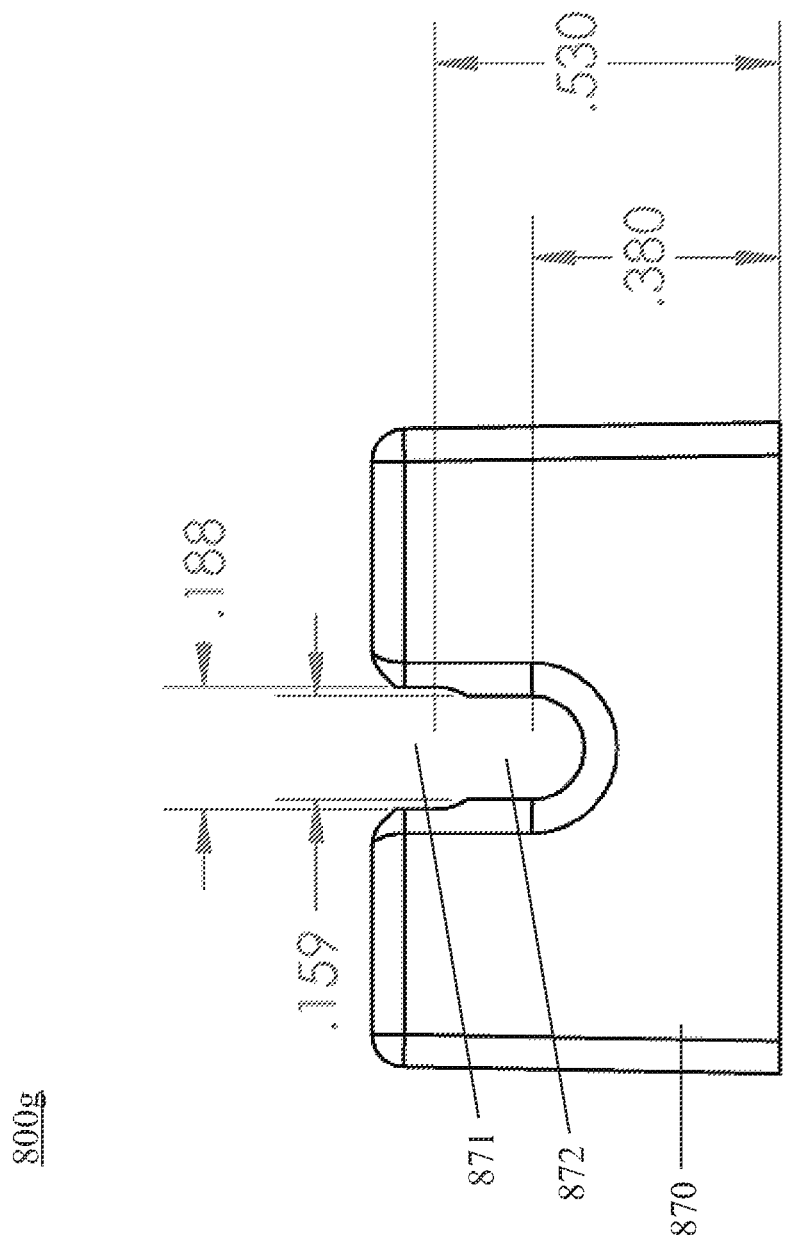
FIG. 8G shows a side view of an embodiment of a pressure sensor with a sensor slot.

FIG. 8G shows a side view 800g of an embodiment of a pressure sensor with sensor slot that may be used in the device 100 of FIG. 1. In at least one embodiment, FIG. 8G includes at least a sensor 870, an entrance opening 871, and a sensor slot 872. In other embodiments, FIG. 8G may not have all of the elements or features listed and/or may have other elements or features instead of or in addition to those listed.

FIG. 8G shows an alternative embodiment that may be used as one of sensors 120a-b in device 100 of FIG. 1 or may be installed in the receptacles (e.g., first receptacle 320, second receptacle 330) of the pump system 300a for measuring the pressure of the tubing 130 or 360. In FIG. 8G, the sensor 870 includes a sensor slot 872 that is in direct contact with sensing elements of sensor 870, which meets an entrance opening 871 that is wider than the sensor slot 872 for easier position and insertion of the tubing into the sensor slot 872. In other embodiments, sensor 870 may include other structures or other dimensions.

FIG. 8H shows a side view 800h of another embodiment of a pressure sensor with sensor slot. In at least one embodiment, FIG. 8H includes at least a sensor 880, an entrance opening 881, and a sensor slot 882. In other embodiments, FIG. 8H may not have all of the elements or features listed and/or may have other elements or features instead of or in addition to those listed.

FIG. 8H shows an alternative embodiment that may be used as sensor 120c in pump 100 of FIG. 1 or may be installed in the receptacles (e.g., first receptacle 320, second receptacle 330) of the pump system 300a for measuring the pressure of the tubing 130 or 360. Similar to sensor 870 of FIG. 8G, the sensor 880 also includes a wider entrance opening 881 leading to a narrower sensor slot 882 that is in direct contact with sensing elements of sensor 880 for easier position and insertion of the tubing. In one embodiment, sensor 880 has a greater height and smaller width than the sensor 870. In other embodiments, sensor 880 may include other structures or other dimensions.

Figure 9A:
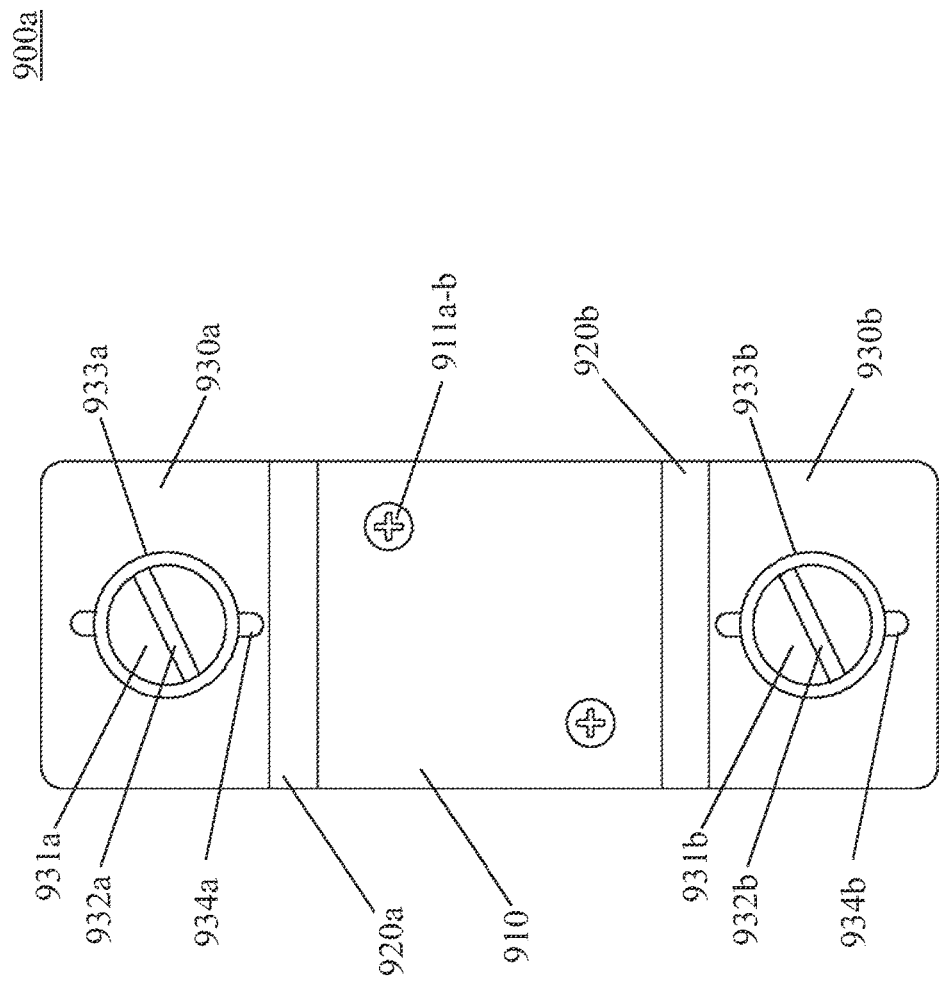
FIG. 9A shows a view of an embodiment of a structure for mounting the sensors in the pump receptacle to the back side of the pump receptacle inside the pump.

FIG. 9A shows a back view 900a of an embodiment of the structure for mounting the sensors in the pump receptacle from the back side inside the pump. FIG. 9A includes at least a middle portion 910 that includes at least two screws 911a-b, and two connector portions 920a and 920b for connecting to a top portion 930a and a bottom portion 930b. FIG. 9A also includes, in the top portion 930a, a screw 931a, a groove 932a, a washer 933a, and a slit 934a. FIG. 9A further includes, in the bottom portion 930b, a screw 931b, a groove 932b, a washer 933b, and a slit 934b. In other embodiments, FIG. 9A may not have all of the elements or features listed and/or may have other elements or features instead of or in addition to those listed.

Middle portion 910 is a portion of the structure to which the sensor(s) may be mounted on the front side (not shown in FIG. 9A), optionally via screws. In at least one embodiment, middle portion 910 may connect to a top portion and a bottom portion, which are further attached to two bosses of either of the pump receptacles (e.g., first receptacle 320, and second receptacle 330) for positioning the sensor(s) in the slot of the receptacle.

Screws 911a-b are a pair of screws for fastening the sensor(s) to the middle portion 910 on the front side. In this specification, whenever one type of fastener is used, another type of fastener may be substituted to obtain a different embodiment. For example, screws, snaps, rivets, tabs that engage in slots, glue, adhesives, and/or straps may be used for any of the fasteners in this specification. Screws, snaps, rivets, tabs that engage in slots, glue, adhesives, and/or straps may be substituted one for another to obtain different embodiments. Also, in general, many fasteners have two parts that interlock with one another to hold two pieces together, where one of the two parts of the fastener is on one piece and another of the two parts in another piece. In this specification which piece has which part may be reversed to obtain a different embodiment. For example, two pieces—one piece having slots and one piece having screws that mate with the slots, which piece has the slots and which piece has the screws may be reversed from that which is shown in the drawings to obtain another embodiment.

Connector portions 920a and 920b connects the middle portion 910 to a top portion and a bottom portion, respectively. In at least one embodiment, connector portions 920a and 920b are perpendicular to the middle portion 910 that is not at the same plane as the top and/or bottom portion.

Top portion 930a is the top portion of the structure for connecting to a boss of the receptacle, optionally via a screw. In at least one embodiment, top portion 930a includes a slit for the screw to go through for fastening the top portion to the receptacle. In at least one embodiment, top portion 930a is parallel to the middle portion 910. In other embodiments, top portion 930a may include other structures and/or shapes.

Bottom portion 930b is similar to the top portion 930a. Bottom portion 930b includes the bottom portion of the structure below the middle portion 910.

Screws 931a and 931b are a pair of screws for fastening the top portion 930a and bottom portion 930b, respectively, to the pump receptacle. In at least one embodiment, screws 931a and 931b go through slits on top portion 930a and bottom portion 930b and further mate with holes, optionally with screw threads, in a top boss and a bottom boss that are part of the receptacle. In other embodiment, other types and/or numbers of fasteners may be substituted to obtain different embodiments.

Grooves 932a and 932b are linear grooves on the surfaces of screw 931a and 931b for tightening screw 931a and 931b, respectively. In at least one embodiment, a user may use a flat head screw driver or other tools.

Washers 933a and 933b are a pair of thin disks or rings with a hole in the middle, for the purpose of distributing the load of the screws 931a and 931b toward the top portion 930a and bottom portion 930b, respectively. In at least one embodiment, washers 933a and 933b are made from plastic, metal, or other materials. Washers 933a and 933b are optional.

Slits 934a and 934b are slits or slots located in top portion 930a and bottom portion 930b, respectively, for the screw 931a and 931b to go through for fastening the top portion 930a and the bottom portion 930b to the bosses of pump receptacle.

Figure 9B:
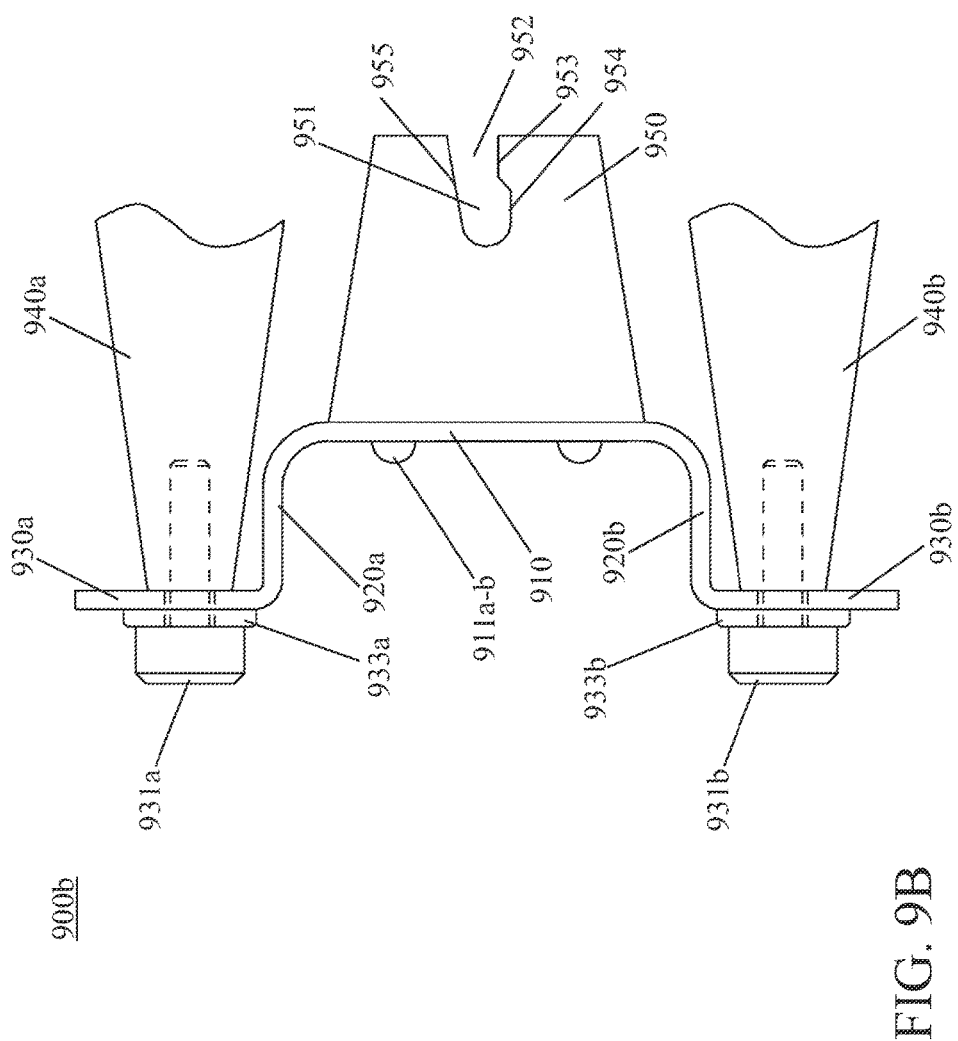
FIG. 9B shows a side view of an embodiment of the structure for mounting the sensors in the pump receptacle.

FIG. 9B shows a side view 900b of an embodiment of the structure for mounting the sensors in the pump receptacle. FIG. 9B includes at least middle portion 910, screws 911a-b, connector portions 920a and 920b, top portion 930a, bottom portion 930b, screw 931a, washer 933a, screw 931b, and washer 933b, which were discussed in conjunction with FIG. 9A. FIG. 9B further includes at least a top boss 940a, a bottom boss 940b, a sensor 950, a slot 951, an opening 952, and walls 953, 954, and 955. In other embodiments, FIG. 9B may not have all of the elements or features listed and/or may have other elements or features instead of or in addition to those listed.

FIG. 9B shows that sensor(s) may be mounted to the middle portion of the structure facing the pump receptacle, which structure is affixed, at the top and bottom portions, to the back side of the pump receptacle inside the pump. In at least one embodiment, the sensor(s) protrudes from the middle portion of the structure with the sensor slot(s) aligning with a slot of the receptacle, while the connector is inserted into the receptacle from the front side thus inserting the tubing into the sensor slot(s). FIG. 9B shows an embodiment of mounting the sensor(s) in the pump receptacle such that a small amount of vertical movement allows the sensor slot(s) to align with the tubing that is attached to or retained by the connector during the insertion or extraction of the tubing.

Top boss 940a is a structure located on top of the receptacle from inside the pump, for engaging a screw that fastens the top portion 930a to the top boss 940a so that the sensor(s) on the middle portion 910 may be properly positioned.

Bottom boss 940b is similar to the top boss 940a. Bottom boss 940b is below the receptacle of the pump.

Sensor 950 may be an embodiment of sensors 120a, 120b, 120c, 610, 830, 850, 870, or 880, which were discussed in conjunction with FIGS. 1, 6A-C, and 8A-H. Slot 951, opening 952, and walls 953, 954, and 955 may be similar to cavity 833, opening 832, neck wall 836, cavity wall 838, and side wall 834, respectively, which were discussed in conjunction with FIGS. 8C and 8D. In at least one embodiment, sensors with a wider entrance opening (e.g., as shown in FIGS. 8G and 8H) may be mounted to the structure for positioning the wider entrance opening in the slot of the receptacle. In other embodiments, other structures and/or sensors may be included for positioning sensors in pump receptacles.

Figure 10:
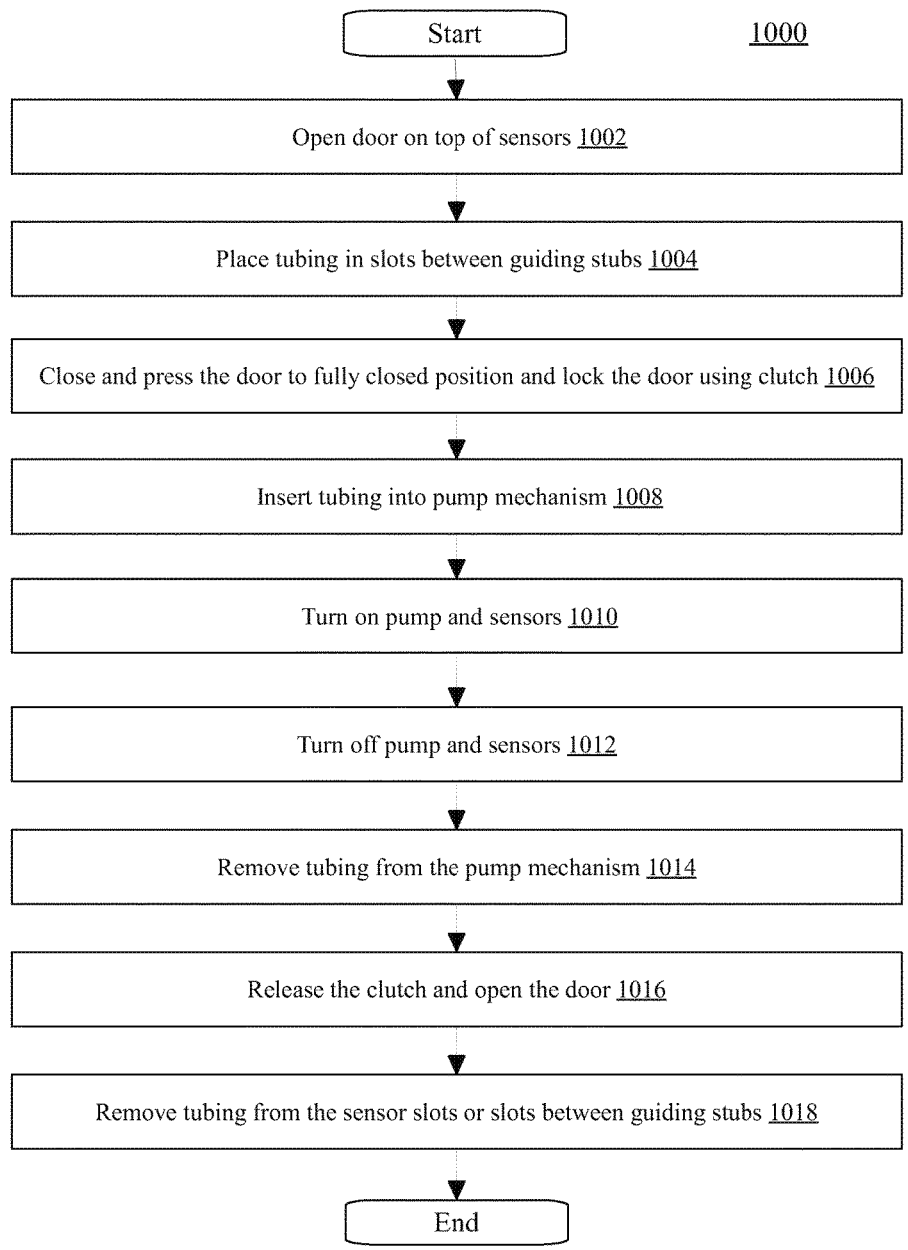
FIG. 10 shows a flowchart of an embodiment of a method of using the pump of FIG. 1.

Methods of Using and Assembling Device for Insertion of Tubing into Irrigation and Infusion Fluid Pumps FIG. 10 shows a flowchart of an embodiment of a method 1000 of using the device of FIG. 1.

In step 1002, door 110 is opened. Optionally step 1002 includes releasing optional lock 115 before opening the door 110.

In step 1004, tubing 130 is placed into slots in-between guiding stubs 113a-b and 113c-d. Alternatively, tubing 130 may be placed in guiding concave 127a-b and/or via bearing 124 in the opening 125.

In step 1006, the door 110 is closed and pressed to the fully closed position for pushing the tubing 130 into sensor slots 121a-c. Optionally step 1006 also includes locking the door 110 via optional lock 115.

In step 1008, tubing 130 is inserted to pump mechanism 140 for transporting fluid.

In step 1010, the pump 101 and sensors 120a-c are turned on so that the sensors 120a-c may measure and/or detect fluid properties in the tubing 130.

In step 1012, the pump 101 and sensors 120a-c are turned off after use.

In step 1014, tubing 130 is removed from the pump mechanism. Alternatively, tubing 130 may be removed from the sensor slots 121a-c before removing tubing 130 from the pump mechanism.

In step 1016, optional lock 115 is released and the door 110 is opened.

In step 1018, tubing 130 is removed from the sensor slots 121a-c, optionally by pulling. In an alternative embodiment, guiding stubs 113a-b and 113c-d retain tubing 130 and, when the door 110 is opened, retract tubing 130 from the sensor slots 121a-c. In this embodiment, step 1018 may include removing tubing 130 from the slots in-between guiding stubs 113a-b and 113c-d.

In an embodiment, each of the steps of method 1000 is a distinct step. In another embodiment, although depicted as distinct steps in FIG. 10, step 1002-1018 may not be distinct steps. In other embodiments, method 1000 may not have all of the above steps and/or may have other steps in addition to or instead of those listed above. The steps of method 1000 may be performed in another order. Subsets of the steps listed above as part of method 1000 may be used to form their own method.

Figure 11:
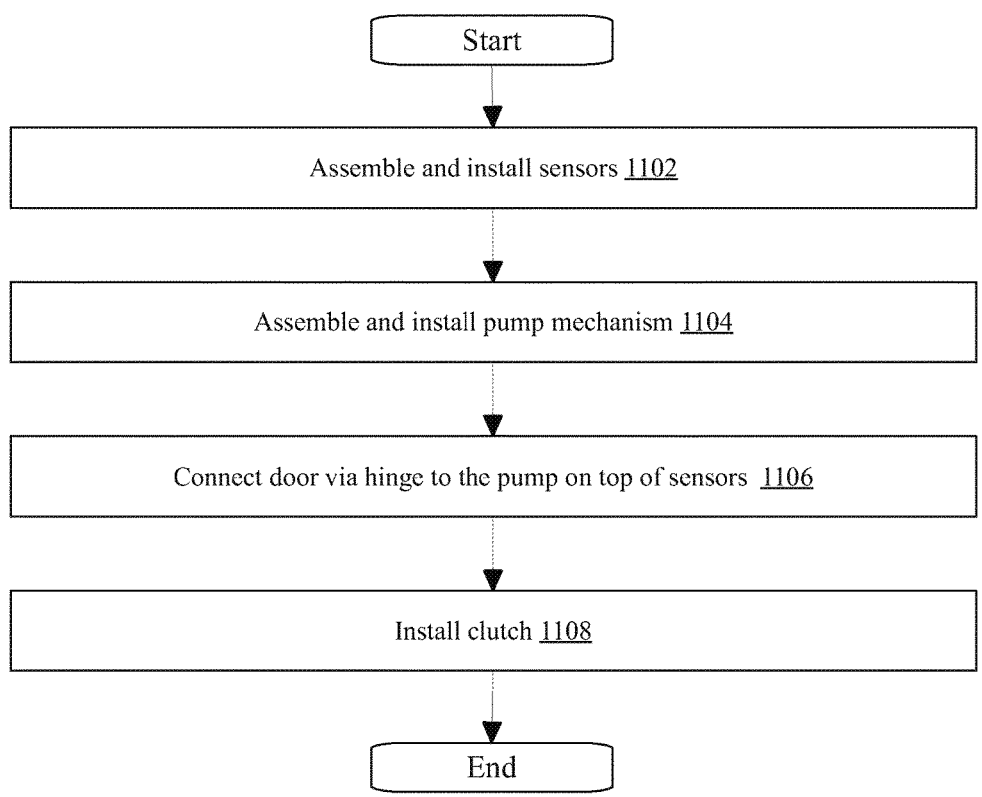
FIG. 11 shows a flowchart of an embodiment of a method of assembling the pump of FIG. 1.

FIG. 11 shows a flowchart of an embodiment of a method 1100 of assembling the device of FIG. 1.

In step 1102, sensors 120a-c are assembled and installed in a slot of the pump 101.

In step 1104, pump mechanism 140 is assembled and installed in the pump 101. An embodiment of the pump mechanism 140 was discussed in conjunction with FIG. 3A.

In step 1106, door 110 is installed and connected to the pump via hinge 114 that is on top of the sensors 120a-c.

In step 1108, optional lock 115 is installed on hinge 114 for locking the door 110.

In an embodiment, each of the steps of method 1100 is a distinct step. In another embodiment, although depicted as distinct steps in FIG. 11, step 1102-1108 may not be distinct steps. In other embodiments, method 1100 may not have all of the above steps and/or may have other steps in addition to or instead of those listed above. The steps of method 1100 may be performed in another order. Subsets of the steps listed above as part of method 1100 may be used to form their own method.

Figure 12:
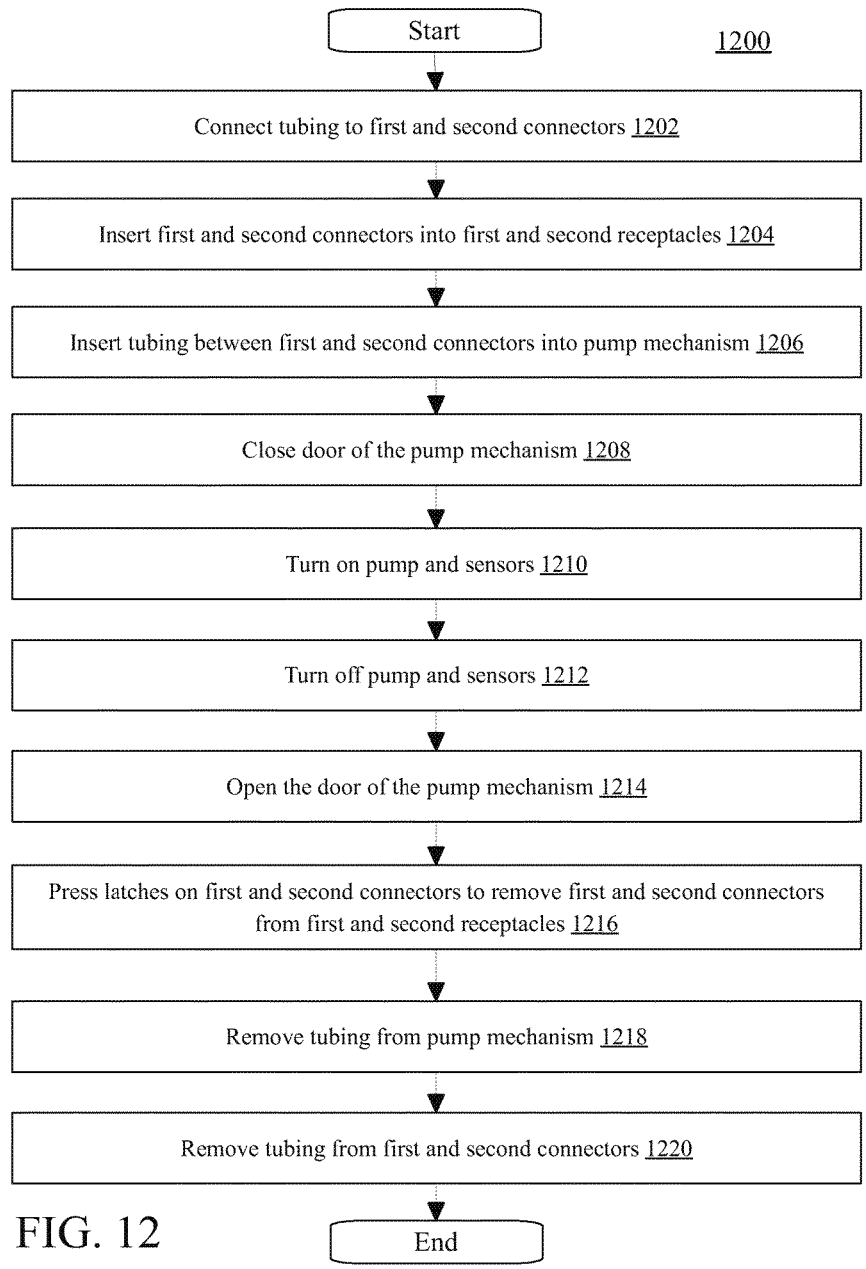
FIG. 12 shows a flowchart of an embodiment of a method of using the pump system of FIG. 3A.

FIG. 12 shows a flowchart of an embodiment of a method 1200 of using the device of FIG. 3A.

In step 1202, tubing 360 is connected to first connector 340 and second connector 350. In an alternative embodiment, tubing 360 is partially affixed to the first connector 340 and second connector 350.

In step 1204, first connector 340 and second connector 350 are inserted into first receptacle 320 and second receptacle 330, respectively.

In step 1206, middle portion 362 of the tubing 360 is placed in-between rotor 314 and bottom casing 318b of the pump mechanism 310.

In step 1208, the door 311 of pump mechanism 310 is closed to raise bottom casing 318b to a position that the middle portion 362 of tubing 360 is compressed by the rollers 316a-n against the bottom casing 318b as the rollers 316a-n pass over tubing 360.

In step 1210, pump 301 and sensors within the first receptacle 320 and second receptacle 330 are turned on for transporting fluid in tubing 360 and measuring fluid properties. The rotor of the pump 301 rotates. As the rotor rotates, rollers 316a-n pass over tubing 360, each roller forms a moving compressing section of tubing 360 that pushes the fluid through the tubing in the direction of rotation of the rotor.

In step 1212, pump 301 and sensors are turned off when finished using.

In step 1214, door 311 of the pump mechanism 310 is opened to lower the bottom casing 318b to release middle portion 362 of tubing 360 from compressed position.

In step 1216, tab 342 of first connector 340 and tab 352 of second connector 350 are pressed to release the first connector 340 and second connector 350 from the first receptacle 320 and second receptacle 330.

In step 1218, tubing 360 is removed from the pump mechanism 310.

In optional step 1220, tubing 360 is removed from first connector 340 and second connector 350. In an alternative embodiment, tubing 360 is partially affixed to the first connector 340 and second connector 350.

In an embodiment, each of the steps of method 1200 is a distinct step. In another embodiment, although depicted as distinct steps in FIG. 12, step 1202-1220 may not be distinct steps. In other embodiments, method 1200 may not have all of the above steps and/or may have other steps in addition to or instead of those listed above. The steps of method 1200 may be performed in another order. Subsets of the steps listed above as part of method 1200 may be used to form their own method.

Figure 13:
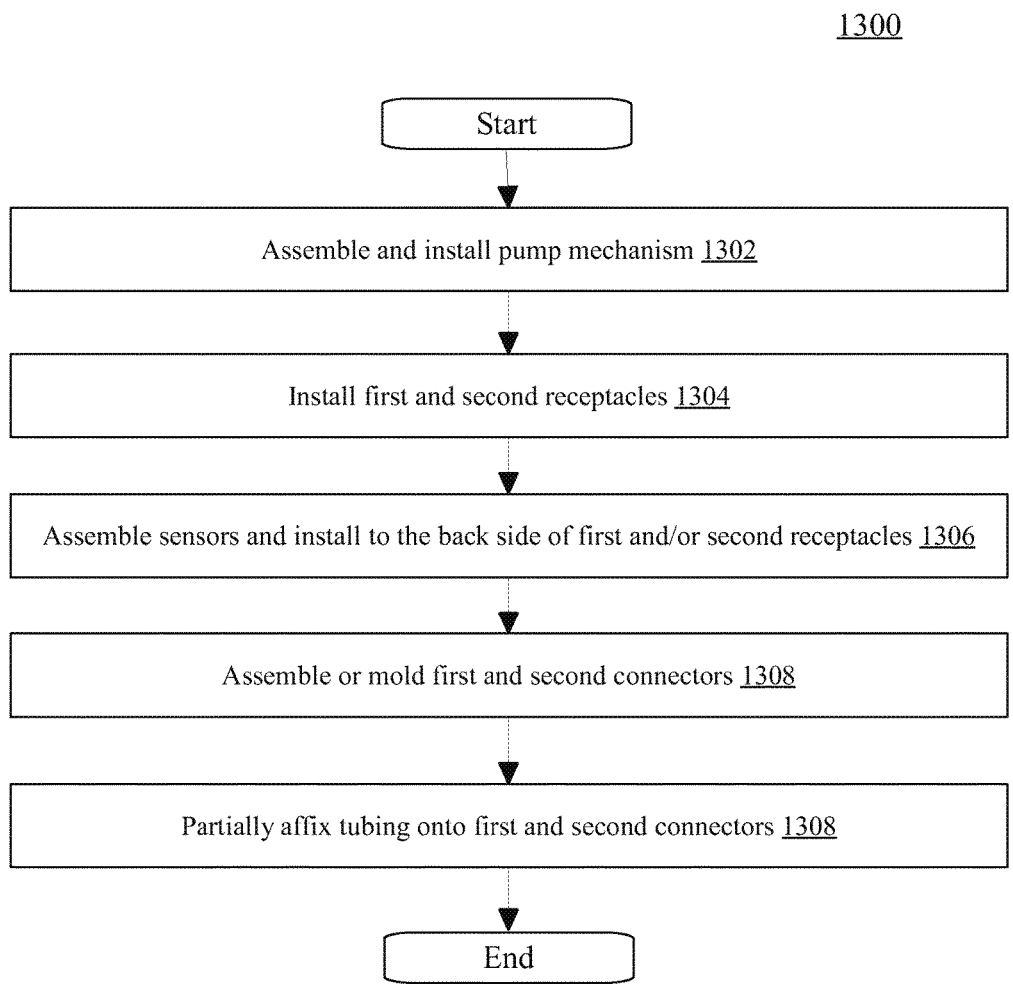
FIG. 13 shows a flowchart of an embodiment of a method of assembling the pump system of FIG. 3A.

FIG. 13 shows a flowchart of an embodiment of a method 1300 of assembling the device of FIG. 3A.

In step 1302, pump mechanism 310 is assembled and installed in pump 310.

In step 1304, first receptacle 320 and second receptacle 330 are molded and/or installed in pump 310.

In step 1306, sensors are assembled and installed to the back side of first 320 and/or second receptacle 330. An embodiment of structures for installing sensors to the receptacles was discussed in conjunction with FIGS. 9A and 9B.

In optional step 1308, tubing 360 is partially affixed to first connector 340 and second connector 350. An embodiment of the manner of partially affixing tubing 360 to the connectors was discussed in conjunction with FIGS. 7A and 7B.

In an embodiment, each of the steps of method 1300 is a distinct step. In another embodiment, although depicted as distinct steps in FIG. 12, step 1302-1308 may not be distinct steps. In other embodiments, method 1300 may not have all of the above steps and/or may have other steps in addition to or instead of those listed above. The steps of method 1300 may be performed in another order. Subsets of the steps listed above as part of method 1300 may be used to form their own method.

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A device, comprising:
a pump that transports fluid in a tubing of a particular outside diameter in a particular direction;
a slot in the pump, into which the tubing is inserted;
a door for inserting the tubing into the slot, the door being hingedly connected to the pump, wherein the door, when closed, covers the slot with two sides of the door extending beyond either side of the slot;
two panels, one at each side of the door, each panel having a notch for guiding the tubing; the notch having an opening that faces away from an underside of the door and faces towards the slot, so that during noiinal operation the tubing can be located in the slot without being located in the notch, the tubing can remain in the slot without contacting the notch as the door swings closed, and only after the door is at an angle that is closer to being closed than to being fully open, the notch contacts the tubing and pushes the tubing into the slot as the door is further closed;
a bar connecting the two panels at the sides of the door for providing pressure across a length of the tubing for pushing the tubing into the slot as the door is closed.

2. The device of claim 1, further comprising a lock for locking and releasing the door.

3. The device of claim 1, wherein the slot is slightly narrower than the outside diameter of the tubing.

4. The device of claim 1, wherein the notches formed by the panels are narrower than the outside diameter of the tubing for retaining the tubing, and as a result opening the door retracts the tubing from the slot.

5. The device of claim 1, wherein the slot is within a sensor, wherein the sensor measures properties of the fluid in the tubing in the slot.

6. The device of claim 5, wherein the sensor is a bubble detector for detecting bubbles in the tubing.

7. The device of claim 5, wherein the sensor is a pressure sensor for measuring pressure of the fluid in the tubing.

8. The device of claim 5, wherein as a result of the bar pushing the tubing into the slot, the tubing is aligned with the sensor.

9. The device of claim 1, wherein the bar includes a concave surface facing the slot, the concave surface being in contact with an arc of the tubing across a length of the tubing.

10. A device, comprising:
a pump that transports fluid in a tubing of a particular outside diameter in a particular direction, the pump having a receptacle for engaging a connector;
a door having an underside facing a peristaltic pump mechanism and covering the peristaltic pump mechanism, the receptacle being located to a side of the door that is not covered by the door, the receptacle is not covered by the door;
a slot in the pump receptacle;
the connector that engages the receptacle includes guiding and supporting structures for inserting the tubing into the slot and retaining the tubing in place, the connector being partially attached to the tubing;
wherein the connector is detachable from the receptacle, wherein detaching the connector from the receptacle results in retracting the tubing from the slot.

11. The device of claim 10, wherein the connector includes a tab that holds the connector to the receptacle and when depressed releases the connector from the receptacle.

12. The device of claim 10, wherein the guiding and supporting structures include at least two guiding members for guiding the tubing and a supporting edge with ends connected to the notches, each of at least two of the at least two guiding member forming a notch, the supporting edge having a concave surface facing the receptacle for providing pressure across a length of the tubing for pushing the tubing into the slot.

13. The device of claim 12, wherein the supporting edge is in contact with an arc of the tubing between 60 degrees and 180 degrees, the tubing having a length, the arc of the tubing being an arc that is perpendicular to the length.

14. The device of claim 12, wherein the two guiding members have partially circular grooves facing the receptacle.

15. The device of claim 12, wherein the two guiding members have channels for the tubing to go through.

16. The device of claim 12, wherein the connector being partially attached to the tubing including attachment of the tubing to the ends of the supporting edge but not along the supporting edge.

17. The device of claim 12, wherein the connector being partially attached to the tubing including attachment of the tubing to the at least two guiding members while the tubing is not attached to the supporting edge.

18. The device of claim 10, further comprising a conductor that completes a circuit which provides an indication that the tubing retained by the connector is fully and properly inserted into the slot.

19. The device of claim 10, wherein the connector being a first connector and the receptacle being a first receptacle, the device includes a second connector that engages with a second receptacle, wherein the first connector and the second connector are in different shape so that one of the first connector and the second connector is not able to engage the other's receptacle.

20. The device of claim 10, wherein the slot is in at least a sensor for measuring properties of fluid in the tubing.

21. A method comprising:
partially attaching a tubing to a connector, the connector including at least two guiding members connected via a supporting edge for providing pressure across a length of the tubing;
inserting the connector in a receptacle on a pump, the connector being detachable from the receptacle, wherein inserting the connector in the receptacle connects to the connector to the pump, wherein a slot is located within the receptacle, the slot being located in only a portion of the receptacle, wherein the tubing is inserted into the slot as a result of the connector being inserted in the receptacle; and
wherein the tubing is retained in place, by the connector as a result of being partially attached to the connector, wherein the pump, when in operation, transports fluid in the tubing in a particular direction, wherein detaching the connector from the receptacle results in retracting the tubing from the slot and results in detaching the connector from the pump.

22. A device comprising:
a connector;
a tubing that is at least partially attached to the connector, the connector including at least two guiding members connected via a supporting edge for providing pressure across a length of the tubing;
a receptacle;
a pump, the receptacle being on the pump;
the connector being inserted in the receptacle on the pump, wherein inserting the connector in the receptacle connects to the connector to the pump, the connector being detachable from the receptacle, wherein a slot is located in the receptacle, wherein the tubing is inserted into the slot as a result of the connector being inserted in the receptacle; and
wherein the tubing is retained in place by the connector as a result of being partially attached to the connector, wherein the pump, when in operation, transports fluid in the tubing in a particular direction, wherein detaching the connector from the receptacle results in retracting the tubing from the slot and results in detaching the connector from the pump.

23. The device of claim 1, the bar being straight.

24. A device comprising:
a pump that transports fluid in a tubing of a particular outside diameter in a particular direction;
a slot in the pump, into which the tubing is inserted;
a door for inserting the tubing into the slot, the door being hingedly connected to the pump, wherein the door, when closed, covers the slot with two sides of the door extending beyond either side of the slot;
the pump having a rotor, the rotor having an axis about which the rotor rotates, the rotor having a flat face that is perpendicular to the axis, the flat face faces an underside of the door, the rotor being covered by the underside of the door;
two panels, one at each side of the door, each panel forming a notch for guiding the tubing; and
a bar connecting the two panels at the sides of the door for providing pressure across a length of the tubing for pushing the tubing into the slot as the door is closed.

25. The device of claim 1, further comprising a hinge via which the door is hingedly connected to the pump, the hinge not being configured to be detachable from the door, and the hinge not being configured to be detachable from the pump.

* * * * *